(12) United States Patent
Cao et al.

(10) Patent No.: US 8,614,063 B2
(45) Date of Patent: Dec. 24, 2013

(54) METHODS FOR SCREENING FOR COMPOUNDS FOR TREATING CANCER

(75) Inventors: Liangxian Cao, Parlin, NJ (US); Thomas Davis, South Orange, NJ (US)

(73) Assignee: PTC Therapeutics, Inc., South Plainfield, NJ (US)

( * ) Notice: Subject to any disclaimer, the term of this patent is extended or adjusted under 35 U.S.C. 154(b) by 24 days.

(21) Appl. No.: 13/000,726

(22) PCT Filed: Jul. 1, 2009

(86) PCT No.: PCT/US2009/049399
§ 371 (c)(1),
(2), (4) Date: Mar. 24, 2011

(87) PCT Pub. No.: WO2010/002987
PCT Pub. Date: Jan. 7, 2010

(65) Prior Publication Data
US 2011/0165581 A1 Jul. 7, 2011

Related U.S. Application Data

(60) Provisional application No. 61/077,444, filed on Jul. 1, 2008.

(51) Int. Cl.
*C12Q 1/68* (2006.01)
(52) U.S. Cl.
USPC .......... 435/6.13; 435/6.1; 435/6.14; 435/6.18
(58) Field of Classification Search
None
See application file for complete search history.

(56) References Cited

U.S. PATENT DOCUMENTS

| | | | |
|---|---|---|---|
| 2006/0111314 A1 | 5/2006 | Nakamura et al. | |
| 2007/0111203 A1 | 5/2007 | Cao et al. | |
| 2008/0242622 A1* | 10/2008 | Lowe et al. | 514/27 |

OTHER PUBLICATIONS

Hosen et al., Bmi-1-Green Fluorescent Protein-Knock-In Mice Reveal the Dynamic Regulation of Bmi-1 Expression in Normal and Leukemic Hematopoietic Cells; Stem Cells, vol. 25, pp. 1635-1644, 2007.*
Strausberg et al., Generation and initial analysis of more than 15,000 full-length human and mouse cDNA sequences; PNAS, vol. 99, No. 26, pp. 16899-16903, 2002.*
Genbank record BC011652.2 accessed Dec. 13, 2012.*
Extended European Search Report for 09 774 437.9 dated Oct. 17, 2011.
Guo Wei-Jian et al: "Mel-18, a polycomb group protein, regulates cell proliferation and senescence via transcriptional repression of Bmi-1 and c-Myc oncoproteins", Molecular Biology of the Cell, vol. 18, No. 2, Feb. 2007, pp. 536-546.
Nowak Katrin et al: BMI1 is a target gene of E2F-1 and is strongly expressed in primary neuroblastomas, Nucleic Acids Research, vol. 34, No. 6, 2006, pp. 1745-1754.
Yang Jianchang et al: Bmi-1 is a target gene for SALL4 in hematopoietic and leukemic cells. Proceedings of the National Academy of Sciences of the United States of America, vol. 104, No. 25, Jun. 2007, pp. 10494-10499.
International Search Report for PCT/US2009/049399, dated Oct. 15, 2009.
Written Opinion for PCT/US2009/049399, dated Oct. 15, 2009.
Gunkel et al., "Localization-dependent translation requires a functional interaction between the 5' and 3' ends of oskar mRNA", Genes Dev 1998, 12(11):1652-1664; p. 1661, DNA constructs.
Kullman et al., "ELAV/Hu proteins inhibit p27 translation via an IRES element in the p27 5'UTR", Genes Dev 2002, 16 (23):3087-3099; p. 3092, left col. para 2, right col para 1: p. 3096-3097; Reporter analysis.
Godlewski et al., "Targeting of the Bmi-1 Oncogene/Stem Cell Renewal Factor by MicroRNA-128 Inhibits Glioma Proliferation and Self-Renewal". Cancer Res Nov. 15, 2008, 68(22):9125-9130.

* cited by examiner

*Primary Examiner* — Anne Gussow
*Assistant Examiner* — Addison D Ault
(74) *Attorney, Agent, or Firm* — Hoffmann & Baron, LLP

(57) ABSTRACT

The methods described herein provide nucleic acid constructs and screening methods for identifying and validating compounds for use in the treatment of cancer, wherein the compounds down-regulate the post-transcriptional expression of Bmi-1.

3 Claims, 12 Drawing Sheets

Bmi-1– 5' UTR

5' CAGCAACUAUGAAAUAAUCGUAGUAUGAGAGGCAGAGAUCGGGGCGAGACAAUGGGGAUGUGGGCGGGAGCCCC
GUUCCGGCUUAGCCAGCACCUCCCAGCCGCGAGAUAAACCGAUCGCGCCCCCGCGCCUCCCCGAGUG
CGGAGCCGGGAGGAGGAGGCCCCGAGGAGGCCCCGAGGAGGCGUUGGAGGUCCGAGGCGG
AGGCGGAGGAGGAGGAGGCGCCCGAGGCCGAGGCCCGAGCCGGAGCAGGAGCCCGAGGCGGCAUG

AGA CGA GCG CAG GCU CUC GCU AGA UGG CCG CUU GGC CUG GUU UCA CAU UCU GCU GAA CGA
CGU CUG CAG CUC CUC GCU GCU AGA UGG CCG CUU GGC CUG GUU UCA CAU UCU GCU GAA CGA
CUU UUA ACU UUC AUU GUC UUU UCC GCC CGC UUC GAU CGC CUC GCG CCG CGC GCU CUU
UCC GGG AUU UUU UAU CAA GCA GAA AUG3'

FIG. 1

Bmi-1 – 3' UTR

5' UGAGGUUGAUACCUGAGACUGUUAAGGAAAAAAUUUAAACCCCUGAUUUAUAGAUAUCUUCAUGCCAUUACA
GCUUCUAGAUGCUAAAUACAUGCUAUCGUCCAAUUGCUUUGUUAAUUGUAGUGACAUUAAAUUGGCUAUAAAAGA
UGGACUACAUGUGAUACUCCUAUGGACGUUAAUUGAAAGAUUGGAAAGAAUGGGUUUCUUGGAAGC
AGGCAAGACAUUUUCUCUGUGUAAGGAAAGAUGGGAAAGAGUUUGUAAUCUGUAACCAUUGGAUUGGAAGUACUCUGC
AGUGGACAUAAGCAUUGGGCCAUAGUUUGUUAAUCUGUAGAAAACAAGUGCUUUUAAUCCAACAUUCCCUGACGUUCUGUUA
UUACGCUGUUUUGUGAGAACCUGUAGAAAUAAGUCACCAUUUUAUCUUGAAAAUUCAACCGAAAGAAUAUGCAUAGAA
UAAUGCAUUCUAGUAGCCAUGUGUGAGAAUAACAAGUCCUUUUAUCAUAUUUAGCCAUAUUUAGCCUUUUGAUCCUGUUUGAUUUA
UACUUCUGUUUAUUUACUGACUGCAAACCGAUCAGUGUUUAAAUGAUUCGCUUUUGAAAUCAGUUAAAUCAGAAUCUGUAAAGCGGGUA
CAUAUGGGUAAUAUAGAGAUGAAUGUUAAAAUUCUCCAACUGGUUCGACCUUUGCAGAACUAAAGUCCAUAGAAUGCAUUAUGCAAUGC
UACCAGCAAAGAAUACUUUCUAAUUUCCAUUGGAUAAUAAGUUCCAUAAGUCCUGUAGAAUUGUCCAGUGAAAAAAUUGUUAACUGAGAAA
UACUUUAUAUAACUUUCUCCAGUAAUACAUGUUAAAUUACUGAAUGGAAUGAUAUAAAAUGCAUUGGAAAACCGUCUAUUAGGAGGCAUUGCUAAAGGCUAGAGUUGUACAGGUUCUUUUA
UUCUAAAACCAUUUUAAAUUUUAUAAAGUAUGAAUAUCUUCUGCUAAUAUGAAUUGAAAUAUAGA
AGCAGUAUUUAUUAGAGCUUCUACAGUAUUUUAAAGAGCAUGUUCUUGGGUCGAACCAUCACCAUUCAUGUGAACCCCACCC
AACAAUUUCAGUUAUUUGCCUUUGGUCGAACAUUCCAUCAGUAUUGGUGAGGGUUU
AUUCUAUAUGAAUAUAAGUGCUAAUGUUCAUGUGGUAUAAGCUAAACAUUUACAUAUUUUAUCUGCCCAGUCUGCAAAGAA
GCACAAUCUAUAUACGAUGCUAAACGAUGUUUAUGUCAUAUAGUCACAUAUUUUAUCAAGAGAAUACUUCUGCUUUUCU
UUAAAAAAAUAAAUACUAAAAUCUAUAUAGAAGUAAAUAUUUCAUUUGGACCUAAAUUGUACAGUCCC
AUUGUAAGAAAAAAAGAAAAUAAUAAAAAAAAAUUUCAUUUGUAAAUUGGAAAAAUCCAAUAAAAAAGGAUAU
UCAUUUAGAAAAAAAAAAAAAAAAAAAAAAAA 3'

FIG. 2

Alignment of mouse and human Bmi-1 5'UTR
(88.8% idendical)

```
Consensus  CAGCAACTATGAAATAATCGTAGTAT-A-AGGCAGAGATCGGG--GAGACAATGGGGA  58
   mbmi1   ------------ATAATCGTAGTATTAAAGGCAGAGATCGGGA-GAGACAATGGGGA  44
   hbmi1   CAGCAACTATGAAATAATCGTAGTATGAGAGGCAGAGATCGGGGCGAGACAATGGGGA  58

Consensus  -GT-GGCG-GGGAGCCCCG--C-GGCTTAGCA-CACCTCCC-GCCCCGCAGAATAA-A  116
   mbmi1   GGTTGGCGAGGGAGCCCCGCGCAGGCTTAGCAACACCTCCCGGCCCCGCAGAATAATA  102
   hbmi1   TGTGGGCGCGGGAGCCCCGTTCCGGCTTAGCAGCACCTCCCAGCCCCGCAGAATAAAA  116

Consensus  C-G-TCG-GCCCC-TC-GCGCGC--CCTCCCCGAG-GCGG---CGGGAGG-GGCGGC-  174
   mbmi1   CGGCTCG-GCCCC-TCTGCGCGC--CCTCCCCGAGCGCGGC-CGGGAGGCGGCGGCT  155
   hbmi1   CCGATCGCGCCCCCTCCGCGCGCGCCCTCCCCGAGTGCGGAGCGGGAGGAGGCGGCG  174

Consensus  GCG-CCGAGGAGGAGGAG----AGGCCCCG-AGGAGG-GGCG---GGAGG-CG-G-CGG  232
   mbmi1   GCG-CCGAGGAGGAGGAG----AGGCCCCG-AGGAGGCGGCGGCGGAGGCCGCG-CGG  206
   hbmi1   GCGGCCGAGGAGGAGGAGGAGGAGGCCCCGGAGGAGGAGGCGTTGGAGGTCGAGGCGG  232

Consensus  AGGCGGAGGAGG-------CCG-G---G---GGAGGAGGCCG--GCGC---GAGCAGGAGG-  290
   mbmi1   AGGCGGAGGAGG------CCGCGCGGGAGGAGGAGGCCGCAGCGCGCGAGCAGGAGG-  257
   hbmi1   AGGCGGAGGAGGAGGAGGCCGAGGCGCCGGAGGAGGCCGAGGCGCCGGAGCAGGAGGA  290

Consensus  --CCGGC-GG-G-GCGGCATGAG--GAGCG-GGCGGCCG-GGCTGCTC--GGCCGCGC  348
   mbmi1   --CCGGCGGGGGAGCGGCATGAGCGGAGCGCGGCGGCCGTGGCTGCTCTCGGCCGCGC  313
   hbmi1   GGCCGGCCGGAG-GCGGCATGAGACGAGCGTGGCGGCCGCGGCTGCTCGGGGCCGCGC  347

Consensus  T-G-TGCCCATTGACAGCGGCG-C-GC-GCTCGCT-CAAGATGGCCGCTTGGCTCGCA  406
   mbmi1   TCGGTGCCCATTGACAGCGGCGGCGGCGGCTCGCTCCAAGATGGCCGCTTGGCTCGCA  371
   hbmi1   TGGTTGCCCATTGACAGCGGCGTCTGCAGCTCGCTTCAAGATGGCCGCTTGGCTCGCA  405

Consensus  TTCATTTT-TGCTGAACGACTTTTAACTTTCATTGTCTTTTCCGCCCGCT--GATCGC  464
   mbmi1   TTCATTTTATGCTGAACGACTTTTAACTTTCATTGTCTTTTCCGCCCGCTCAGATCGC  429
   hbmi1   TTCATTTTCTGCTGAACGACTTTTAACTTTCATTGTCTTTTCCGCCCGCTTCGATCGC  463

Consensus  CTCGCGCCGGC-GCTCTTTCCGGGAT-TTTTATCAAGCAGAA          506
   mbmi1   CTCGCGCCGGCCGCTCTTTCCGGGATCTTTTATCAAGCAGAA          471
   hbmi1   CTCGCGCCGGCTGCTCTTTCCGGGATTTTTTATCAAGCAGAA          505
```

FIG. 4

Mouse vs Human 3'UTR Sequence Alignment

```
Consensus  GGTTGATACCT--GACTGTTAAGGAAAA-A-TTTT-AACCCC-TGATTTA----G-T  57
   hbmi-1  GGTTGATACCTGAGACTGTTAAGGAAAAAAATTTTAAACCCC-TGATTTATATAGAT  56
   mbmi-1  ---------TAGGACTGTTAAGGAAAAGATTTTTCAACCCCCTGATTTA----GTT   43

Consensus  A-CTTCAT-C-ATTACAGCTTT-TAGATGCT-AATACATGTGACT-TCGTCCA-TTT 114
   hbmi-1  ATCTTCATGCCATTACAGCTTTCTAGATGCT-AATACATGTGACTATCGTCCAATTT 112
   mbmi-1  ACCTTCATTC-ATTACAGCTTTATAGATGCTTAATACATGTGACTGTCGTCCAGTTT  99

Consensus  GCTT-CTTTTGTAGTGAC-TTAAATTTGGC-ATAAA-GATGGACTA-ATGTGATACT 171
   hbmi-1  GCTTTCTTTTGTAGTGACATTAAATTTGGCTATAAAAGATGGACTACATGTGATACT 169
   mbmi-1  GCTTCCTTTTGTAGTGACTTTAAATTTGGCCATAAATGATGGACTAGATGTGATACT 156

Consensus  -C-TATGGA-GTTAA-TG-AAAGA--GATT-TT--T-TAAAGAATTGG-TTCT-G-- 228
   hbmi-1  CC-TATGGACGTTAATTGAAAAGAAAGATTGTTGTTATAAAGAATTGGTTTCTTGGA 225
   mbmi-1  TCATATGGATGTTAAGTGGAAAGATTGATTCTTTCTAAAGAATTGGATTCT-G--   210

Consensus  -AG-AGG-A----TT-----CTGTGTTAGGAAAGATG-GAAATG-TTTCTGT-ACCA 285
   hbmi-1  AAGCAGGCAAGACTTTTTCTCTGTGTTACGAAAGATGGGAAATGGTTTCTGTAACCA 282
   mbmi-1  -AGAAGG-A----TT-----CTGTGTTAGGAAAGATGTGAAATGATTTCTGTGACCA 256

Consensus  -TGTTTGGAT-TGGAA-T--TCT-CAGTGG--A-A--CATTGGGCCATAGTTTGTTA 342
   hbmi-1  TTGTTTGGATTTGGAAGTACTCTGCAGTGGACATAAGCATTGGGCCATAGTTTGTTA 339
   mbmi-1  CTGTTTGGATCTGGAAATGTTCTACAGTGGGTAGA--CATTGGGCCATAGTTTGTTA 311

Consensus  ATCTCAA-TAA-GCCTACATTACATTCTC-TTGAT-GTTCTTGTTATTA-GCTGTT- 399
   hbmi-1  ATCTCAACTAACGCCTACATTACATTCTCCTTGATCGTTCTTGTTATTACGCTGTTT 396
   mbmi-1  ATCTCAATTAATGCCTACATTACATTCTCTTTGATTGTTCTTGTTATTATGCTGTTC 368

Consensus  TGTGAACCTGTAGAAAACAAGTGCTTTTTATCTTGAAATTCA-C-AA-GGAAAGAAT 456
   hbmi-1  TGTGAACCTGTAGAAAACAAGTGCTTTTTATCTTGAAATTCAACCAACGGAAAGAAT 453
   mbmi-1  TGTGAACCTGTAGAAAACAAGTGCTTTTTATCTTGAAATTCAGCAAATGGAAAGAAT 425

Consensus  A-GCATAGAATA-TGCATTCT-TG-AGCCA-GTCACTGTGAATAAC-ATTTCTTGCA 513
   hbmi-1  ATGCATAGAATAATGCATTCTATGTAGCCATGTCACTGTGAATAACGATTTCTTGCA 510
   mbmi-1  AAGCATAGAATACTGCATTCTGTGCAGCCACGTCACTGTGAATAACAATTTCTTGCA 482

Consensus  TATTTAGCCATTTT-ATTCCTGTTTGATTT-TACTTCTCTGTTGCTAC-CAAAA--G 570
   hbmi-1  TATTTAGCCATTTGATTCCTGTTTGATTTATACTTCTCTGTTGCTACGCAAAACCG 567
   mbmi-1  TATTTAGCCATTTTAATTCCTGTTTGATTTTTACTTCTCTGTTGCTACACAAAAT-G 538

Consensus  ATCAAAG-AAA-----CTT--GTTTTACAATCTGTATGCCTAAAA-GCGGGTACTAC 627
   hbmi-1  ATCAAAGAAAAGTGAACTTCAGTTTTACAATCTGTATGCCTAAAA-GCGGGTACTAC 623
   mbmi-1  ATCAAAGGAAA-----CTT--GTTTTACAATCTGTATGCCTAAAAAGCGGGTACTAC 588

Consensus  CGTTTATTTTACTGACTTGTT-AAATGATTC-CTTTTGTAAGAATCAGATGGCATTA 684
   hbmi-1  CGTTTATTTTACTGACTTGTTAAATGATTCGCTTTTGTAAGAATCAGATGGCATTA 680
   mbmi-1  CGTTTATTTTACTGACTTGTTGAAATGATTCACTTTTGTAAGAATCAGATGGCATTA 645

Consensus  TGCTTGTTGTACAATGCCATATTGGTATATGACATAACAGGAAACAGTATTGTATGA 741
   hbmi-1  TGCTTGTTGTACAATGCCATATTGGTATATGACATAACAGGAAACAGTATTGTATGA 737
   mbmi-1  TGCTTGTTGTACAATGCCATATTGGTATATGACATAACAGGAAACAGTATTGTATGA 702
```

FIG. 5A

```
Consensus  TATATTTATAAAT-CTAT-AA--AATATTGTGTTTCATGCATTCA-AAA---TTGT-  798
   hbmi-1  TATATTTATAAATGCTATAAAGAAATATTGTGTTTCATGCATTCAGAAATGATTGTT  794
   mbmi-1  TATATTTATAAATACTATGAA--AATATTGTGTTTCATGCATTCAAAAACAGTTGT-  756

Consensus  AAA-TTCTCC-AA--GGTTCGACCTTTGC-GATA-C-CA-T--A-CC-ATG-TGAG-  855
   hbmi-1  AAAATTCTCCCAACTGGTTCGACCTTTGCAGATACC-CA-T--AACCTATGTTGAGC  847
   mbmi-1  AAACTTCTCCAAATGGGTTCGACCTTTGCGGATATCACAGTGCACCCAATGCTGAGG  813

Consensus  CTT-C---ACCAGCA-AGAAT-T-TTTTAATGT-GATA-C-A-TT--AAA-TCT-TTC  912
   hbmi-1  CTTGCTTACCAGCAAGAATAT-TTTTAATGTGGATATCTAATTCTAAAGTCTGTTC   903
   mbmi-1  CTTACC-ACCAGCACAGAATTTGTTTTAATGTTGATAACCAGTTTCAAATTCTTTTC  869

Consensus  CA-TTAGAAGCAA-TGGCA-ATCTT-C-ATA-TT--T---CTTTTCTCCA-TAA-AC  969
   hbmi-1  CA-TTAGAAGCAATTGGCACATCTTTCTATACTTTATATACTTTTCTCCAGTAATAC  959
   mbmi-1  CACTTAGAAGCAAATGGCAGATCTT-C-ATAGTTC-TGG-CTTTTCTCCAATAAGAC  922

Consensus  -T-T--A--TTAA-A-----TTGCAGT-AAGAAAAA--TTTAAC--AG--A-AT--A-  1026
   hbmi-1  ATGTTTACTTTAAAAATTGTTGCAGTGAAGAAAAACCTTTAACTGAGAAATATGGAA  1016
   mbmi-1  TT-TCAAAATTAATA-----TTGCAGTAAAGAAAAAT-TTTAACCAAGGCAAAT--AT  971

Consensus  A--GT-TTAATTTTCCATTGG-TA--AT-GAATTAAT---GT-TTTTAAA--T-C-T  1083
   hbmi-1  ACCGTCTTAATTTTCCATTGGCTATGATGGAATTAATATTGTATTTAAAAATGCAT   1073
   mbmi-1  AGTGT-TTAATTTTCCATTGGTTAAAATAGAATTAAT---GT-TTTTAAA--TTC-T  1020

Consensus  -TT-ATCA-T---AATTCTAAAA-A--TTTT-AA-T-AACCAGC----TTGCT-AA--A  1140
   hbmi-1  ATTGATCACTATAATTCTAAAACAATTTTTAAATAAACCAGCAGGTTGCTAAAAGA   1130
   mbmi-1  GTTTATCAGTGGAATTCTAAAATAGATTTTAAAGTCAACCAGCTAATTGCTGAAGTA  1077

Consensus  A-GCATTTTATCTA-AA-TT-ATTTTA-T--A-GTGG-A-A---GTAATTT-AAATT  1197
   hbmi-1  AGGCATTTTATCTA-AAGTT-ATTTTAAT--AGGTGGTATAGCAGTAATTTTAAATT  1183
   mbmi-1  AAGCATTTTATCTACAATTTTATTTTAGTGTATGTGGCACAAGTGTAATTTCAAATT  1134

Consensus  TAAGAGTTG-TTT-A-AGTTAA-A--GGAAT-TGCCTTC-CTG--A-GTCTG-AAA-  1254
   hbmi-1  TAAGAGTTGCTTTTACAGTTAACAATGGAATATGCCTTCTCTGCTATGTCTGAAAAT  1240
   mbmi-1  TAAGAGTTGTTTTCATAGTTAA-A--GGAATCTGCCTTCACTGTAACGTCTGGAAAC  1188

Consensus  AGAA-C-ATTT-TTATGA--TTCTACAGG-ATTTTTAA-TAGAGCAA-CATGTTGAA  1311
   hbmi-1  AGAAGCTATTTATTATGAGCTTCTACAGGTATTTTTAAATAGAGCAAGCATGTTGAA  1297
   mbmi-1  AGAAACAATTTGTTATGAT-TTCTACAGGGATTTTTAA-TAGAGCAAACATGTTGAA  1243

Consensus  TTTAAAATATGAAT-ACCCC-CC----AA-T-TCAGTTT------TGCTTTGGTCGA  1368
   hbmi-1  TTTAAAATATGAATAACCCCACCCAACAATTTTCAGTTTATTTTTTGCTTTGGTCGA  1354
   mbmi-1  TTTAAAATATGAATGACCCCTCC----AAGTCTCAGTTT------TGCTTTGGTCGA  1290

Consensus  ACTT-G-GTGTGTT-ATCA-CCATCAGTTATTTGTGAGG-TGTT-ATTC--TATGAA  1425
   hbmi-1  ACTTGGTGTGTGTTCATCACCCATCAGTTATTTGTGAGGGTGTTTATTCTATATGAA  1411
   mbmi-1  ACTTAGCGTGTGTTTATCAGCCATCAGTTATTTGTGAGGATGTTAATTCCGTATGAA  1347

Consensus  TATTGTTTCATGTTTGTATGGGAAA-T-GTAGCTAA-CATTTCATTGTC--CAGTCT  1482
   hbmi-1  TATTGTTTCATGTTTGTATGGGAAATTGTAGCTAAACATTTCATTGTCCCCAGTCT   1468
   mbmi-1  TATTGTTTCATGTTTGTATGGGAAACT-GTAGCTAAGCATTTCATTGTCTGCAGTCT  1403

Consensus  GCA-AAGAAGCACAATT-TATTGCTTTGTCTTGCTT-TAG-CATTAAATCATTACTT  1539
   hbmi-1  GCAAAAGAAGCACAATTCTATTGCTTTGTCTTGCTTATAGTCATTAAATCATTACTT  1525
   mbmi-1  GCAGAAGAAGCACAATTGTATTGCTTTGTCTTGCTTGTAGCCATTAAATCATTACTT  1460
```

FIG. 5B

```
Consensus  TTACA-A-ATTGCTGTTA-CTTCTGCTTTCTTTAAA-AT-TAGTAAA---GATGTTTT  1596
   hbmi-1  TTACATATATTGCTGTTA-CTTCTGCTTTCTTTAAAAATATAGTAAAG-GATGTTTT  1580
   mbmi-1  TTACACACATTGCTGTTAACTTCTGCTTTCTTTAAAGATTTAGTAAATTGATGTTTT  1517

Consensus  ATGAAG-C-ACAAGATACATATATTTTTATTTTGACCTAAATTTGTACAGTCCCATT  1653
   hbmi-1  ATGAAGTC-ACAAGATACATATATTTTTATTTTGACCTAAATTTGTACAGTCCCATT  1636
   mbmi-1  ATGAAGGCCACAAGATACATATATTTTTATTTTGACCTAAATTTGTACAGTCCCATT  1574

Consensus  GT--GTGT-T--TTTCTAATTATAGATGTAAAAT-AAATTTCATTT-TAATTGGAAA  1710
   hbmi-1  GTAAGTGT-TG-TTTCTAATTATAGATGTAAAATGAAATTTCATTTGTAATTGGAAA  1691
   mbmi-1  GTGTGTGTGTCATTTCTAATTATAGATGTAAAATTAAATTTCATTTTTAATTGGAAA  1631

Consensus  A--T-CAATAAAAAG-ATATTCATTTAGAAAA-A--A--------AA--AAAA----  1767
   hbmi-1  AAATCCAATAAAAAGGATATTCATTTAGAAAAAAAAAAAAAAAAAAAAAAAAAAAAA  1748
   mbmi-1  A--TTCAATAAAAAG-ATATTCATTTAGAAAATACTATGCTCTTTAATTAAAATTTT  1685

Consensus  ---A--AAAA--A-A------A-AAGTTTTGGGAAACCCTGTAGTGGATTGTAAGAG  1824
   hbmi-1  AAAAAAAAAAAAAAAAAAA--AAAA--------------------------------  1771
   mbmi-1  GCTATGAAAAGCACAGTGTGCAGAAGTTTTGGGAAACCCTGTAGTGGATTGTAAGAG  1742
```

METHODS FOR SCREENING FOR COMPOUNDS FOR TREATING CANCER

CROSS-REFERENCE TO RELATED APPLICATIONS

This application is the National Stage of International Application No. PCT/US09/49399, filed Jul. 1, 2009 which claims the benefit of U.S. Provisional Application 61/077,444, filed Jul. 1, 2008, the contents of which are incorporated by reference herein.

INTRODUCTION

The methods described herein provide nucleic acid constructs and screening methods for identifying and validating compounds for use in the treatment of cancer, wherein the compounds down-regulate the post-transcriptional expression of the B-cell specific Moloney murine leukemia virus Integration site 1 gene (Bmi-1).

BACKGROUND

The B-cell specific Moloney murine leukemia virus integration site 1 (Bmi-1) gene, is a member of the Polycomb group (PcG) of transcriptional repressors, was first identified as a pro-oncogene and subsequently discovered to be a necessary regulator of hematopoietic stem cell (HSC) self-renewal (Park et al., 2003, Nature. 423:302-305; Lessard et al., 2003, Nature 423:255-260). Park and colleagues found that Bmi-1 is highly expressed in purified mouse and human HSCs and that the absence of Bmi-1, as demonstrated by Bmi-1 knockout mice, results in the progressive loss of all hematopoietic lineages (Park et al., 2003, Nature. 423:302-305). Furthermore, the transplantation of Bmi-1$^{-/-}$ day 14.5 fetal liver cells into lethally irradiated normal mice, demonstrated that the cells were unable to reconstitute myeloid cells, B cells, and T cells because Bmi-1$^{-/-}$ HSCs were unable to renew (Park et al., 2003, Nature. 423:302-305).

In addition to Bmi-1's role in HSC self renewal, it was found that Bmi-1 transgene expression induced lymphoma in mice (Haupt et al., 1993, Oncogene. 11:3161-3164). It was also discovered that Bmi-1 overexpression is found in many tumor types, including myeloid leukemia, medulloblastoma, neuroblastoma, colorectal cancer, lung cancer, and prostate cancer, and increases with malignancy (Sawa et al., 2005, Int J. Hematol. 82:42-47; Wiederschain et al., 2007, Mol Cell Biol. 27(13):4968-4967; Cui et al., 2007, Am J. Pathol. 170: 130-1378; Reinisch et al., 2006, Histol Histopathol. 21:1143-1149; Breuer et al., 2005, Lung'Cancer. 48:299-306; Kim et al., 2004, Breast. 13:383-388; Glinsky et al., 2005, J. Clin. Invest. 115:1503-1521). Loss of Bmi-1 in various cancerous human cell lines via Bmi-1 specific RNA interference (RNAi) was shown to lead to acute cell death and growth inhibition, whereas loss of Bmi-1 in various normal progenitor or stem cell types was shown to lead to only moderate growth inhibition and not significant cell death (Liu et al., 2006, Oncogene. 25:4370-4375). Thus, Bmi-1 and Bmi-1 is necessary for the survival of cancer cells but has minimal effect on the survival of normal cells.

SUMMARY

The screening assays describe herein are directed to the identification or validation of compounds that target any of the 5'-UTR (untranslated region) and 3'-UTR, or the 5'-UTR or the 3'-UTR of Bmi-1. In particular, these assays involve the use of a nucleic acid construct comprising a reporter gene operably linked to any of the 5'-UTR and 3'-UTR, or the 5'-UTR or the 3'-UTR of Bmi-1. Transcription of the reporter gene can be driven by any promoter, and need not be limited to a Bmi-1 promoter. Indeed, strong promoters, such as the CMV promoter may be used in screening assays. Accordingly, the nucleic acid construct optionally comprises one or more operably linked promoters operably linked to the reporter gene. Included within the scope of the assays described herein are the identification or validation of those compounds that specifically modulate the function of any of the 5'-UTR and 3'-UTR, or the 5'-UTR or the 3'-UTR of Bmi-1 to down-regulate or reduce post-transcriptional expression of a Bmi-1 gene or a reporter gene. Compounds that target any of the 5'-UTR and 3'-UTR, or the 5'-UTR or the 3'-UTR of Bmi-1 and post-transcriptionally down-regulate or reduce expression of Bmi-1 protein can be used to treat cancer in subjects, (e.g., human subjects) in need thereof.

The methods described herein provide for a nucleic acid construct comprising a reporter gene operably linked to (i) the 5'-UTR (untranslated region) of Bmi-1 or a fragment, mutant or post-transcriptional regulatory element thereof and the 3'-UTR of Bmi-1 or a fragment, mutant or post-transcriptional regulatory element thereof; or (ii) the 5'-UTR of Bmi-1 or a fragment, mutant or post-transcriptional regulatory element thereof; or (iii) the 3'-UTR of Bmi-1 or a fragment, mutant or post-transcriptional regulatory element thereof, wherein the 5'-UTR or fragment, mutant or post-transcriptional regulatory element thereof is upstream of the reporter gene and the 3'-UTR or fragment, mutant or post-transcriptional regulatory element thereof is downstream of the reporter gene.

In some embodiments, the nucleic acid construct comprises a reporter gene operably linked to the 5'-UTR of Bmi-1 or a fragment, mutant or post-transcriptional regulatory element thereof and an amino terminal fragment of the Bmi-1 ORF, (e.g., the first 3, 6, 9, 12, 15, 18, 21, 24, or more nucleotides from the 5'-end of the ORF of Bmi-1), wherein the reporter gene is in frame with the amino terminal fragment of the ORF of Bmi-1, and wherein the 5'-UTR of Bmi-1 or a fragment, mutant or post-transcriptional regulatory element thereof and the amino terminal fragment of the Bmi-1 ORF are upstream of the reporter gene. In certain embodiments, the reporter gene lacks an endogenous start codon. In specific embodiments, the nucleic acid construct comprises the first 21 nucleotides from the 5' end of the ORF of human Bmi-1 and the 3'-UTR of human Bmi-1 or a fragment, mutant or post-transcriptional regulatory element thereof.

In some embodiments, the nucleic acid construct comprises a reporter gene operably linked to a carboxy terminal fragment of the Bmi-1 ORF (e.g., the last 3, 6, 9, 12, 15, 18, 21, 24, or more nucleotides from the 3' end of the ORF of Bmi-1) and the 3'-UTR of Bmi-1 or a fragment, mutant or post-transcriptional regulatory element thereof, wherein the reporter gene is in frame with the carboxy terminal fragment of the Bmi-1 ORF and the 3'-UTR of Bmi-1 or a fragment, mutant or post-transcriptional regulatory element thereof and the reporter gene lacks an endogenous stop codon, and wherein the carboxy terminal fragment of the ORF of Bmi-1 and the 3'-UTR of Bmi-1 or a fragment, mutant or post-transcriptional regulatory element thereof are downstream of the reporter gene. In specific embodiments, the nucleic acid construct comprises the last 21 nucleotides from the 3' end of the ORF of human Bmi-1 and the 3'-UTR of human Bmi-1 or a fragment, mutant or post-transcriptional regulatory element thereof.

In some embodiments, the nucleic acid construct comprises a reporter gene operably linked to (i) the 5'-UTR of Bmi-1 or a fragment, mutant or post-transcriptional regulatory element thereof and an amino terminal fragment of the Bmi-1 ORF, (e.g., the first 3, 6, 9, 12, 15, 18, 21, 24, or more nucleotides from the 5' end of the ORF of Bmi-1); and (ii) a carboxy terminal fragment of the Bmi-1 ORF (e.g., the last 3, 6, 9, 12, 15, 18, 21, 24, or more nucleotides from the 3' end of the ORF of Bmi-1) and the 3'-UTR of Bmi-1 or a fragment, mutant or post-transcriptional regulatory element thereof, wherein the reporter gene is in frame with the amino terminal and carboxy terminal fragments of the ORF of Bmi-1 and the reporter gene lacks an endogenous stop codon, and wherein the 5'-UTR of Bmi-1 or a fragment, mutant or post-transcriptional regulatory element thereof and the amino terminal fragment of the Bmi-1 ORF are upstream of the reporter gene, and the carboxy terminal fragment of the ORF of Bmi-1 and the 3'-UTR or a fragment, mutant or post-transcriptional regulatory element thereof are downstream of the reporter gene. In certain embodiments, the reporter gene lacks an endogenous start codon. In a specific embodiment, the nucleic acid construct comprises the 5'-UTR of human Bmi-1 and the first 21 nucleotides of the ORF from the 5' end of the ORF of human Bmi-1. In another specific embodiment, the nucleic acid construct comprises nucleic acid residues 1 to 505 of the 5'-UTR of human Bmi-1 and the first 21 nucleotides of the ORF from the 5' end of the ORF of human Bmi-1. In a specific embodiment, the nucleic acid construct comprises the last 21 nucleotides of the ORF from the 3' end of human Bmi-1 and the 3'-UTR of human Bmi-1.

In one embodiment, the nucleic acid construct comprises a reporter gene operably linked to the 5'-UTR of Bmi-1 or a fragment, mutant, or post-transcriptional regulatory element thereof, and the 3'-UTR of Bmi-1 or a fragment, mutant, or post-transcriptional regulatory element thereof, wherein the 5'-UTR or fragment, mutant or post-transcriptional regulatory element thereof is upstream of the reporter gene and the 3'-UTR or fragment, mutant or post-transcriptional regulatory element thereof is downstream of the reporter gene.

In a particular embodiment, the reporter gene is an ORF whose expression is readily detectable in a high throughput assay, including those selected from the group consisting of a nucleotide sequence encoding or coding for firefly luciferase, renilla luciferase, click beetle luciferase, green fluorescent protein, yellow fluorescent protein, red fluorescent protein, cyan fluorescent protein, blue fluorescent protein, beta-galactosidase, beta-glucoronidase, beta-lactamase, chloramphenicol acetyltransferase and alkaline phosphatase. In a further embodiment, the nucleic acid construct described herein optionally further comprises one or more operably linked promoters.

The methods described herein provide for a host cell containing a nucleic acid construct as described herein. In one embodiment, a host cell contains a nucleic acid construct comprising a reporter gene operably linked to (i) the 5'-UTR of Bmi-1 or a fragment, mutant or post-transcriptional regulatory element thereof and the 3'-UTR of Bmi-1 or a fragment, mutant or post-transcriptional regulatory element thereof; or (ii) the 5'-UTR of Bmi-1 or a fragment, mutant or post-transcriptional regulatory element thereof; or (iii) the 3'-UTR of Bmi-1 or a fragment, mutant or post-transcriptional regulatory element thereof, wherein the 5' UTR or fragment, mutant or post-transcriptional regulatory element thereof is upstream of the reporter gene and the 3' UTR or fragment, mutant or post-transcriptional regulatory element thereof is downstream of the reporter gene.

In some embodiments, the methods described herein provide a host cell comprising a nucleic acid construct, wherein the nucleic acid construct comprises a reporter gene operably linked to the 5'-UTR of Bmi-1 or a fragment, mutant or post-transcriptional regulatory element thereof and an amino terminal fragment of the Bmi-1 ORF, (e.g., the first 3, 6, 9, 12, 15, 18, 21, 24, or more nucleotides from the 5' end of the ORF of Bmi-1), wherein the reporter gene is in frame with the amino terminal fragment of the ORF of Bmi-1, and wherein the 5'-UTR of Bmi-1 or a fragment, mutant or post-transcriptional regulatory element thereof and the amino terminal fragment of the Bmi-1 ORF are upstream of the reporter gene. In certain embodiments, the reporter gene lacks an endogenous start codon. In specific embodiments, the nucleic acid construct comprises the 5'-UTR of human Bmi-1 and the first 21 nucleotides of the ORF from the 5' end of human Bmi-1. In other specific embodiments, the nucleic acid construct comprises nucleic acid residues 1 to 505 of the 5'-UTR of human Bmi-1 and the first 21 nucleotides of the ORF from the 5' end of human Bmi-1.

In some embodiments, the methods described herein provide a host cell comprising a nucleic acid construct, wherein the nucleic acid construct comprises a reporter gene operably linked to a carboxy terminal fragment of the Bmi-1 ORF (e.g., the last 3, 6, 9, 12, 15, 18, 21, 24, or more nucleotides from the 3' end of the ORF of Bmi-1) and the 3'-UTR of Bmi-1 or a fragment, mutant or post-transcriptional regulatory element thereof, wherein the reporter gene is in frame with the carboxy terminal fragment of the Bmi-1 ORF and the reporter gene lacks an endogenous stop codon, and wherein the carboxy terminal fragment of the ORF of Bmi-1 and the 3'-UTR or fragment, mutant or post-transcriptional regulatory element thereof are downstream of the reporter gene. In specific embodiments, the nucleic acid construct comprises the last 21 nucleotides of the ORF from the 3' end of human Bmi-1 and the 3'-UTR of human Bmi-1 or a fragment, mutant or post-transcriptional regulatory element thereof.

In some embodiments, the methods described herein provide a host cell comprising a nucleic acid construct, wherein the nucleic acid construct comprises a reporter gene operably linked to (i) the 5'-UTR of Bmi-1 or a fragment, mutant or post-transcriptional regulatory element thereof and an amino terminal fragment of the Bmi-1 ORF (e.g., the first 3, 6, 9, 12, 15, 18, 21, 24, or more nucleotides from the 5' end of the ORF of Bmi-1); and (ii) a carboxy terminal fragment of the Bmi-1 ORF (e.g., the last 3, 6, 9, 12, 15, 18, 21, 24, or more nucleotides from the 3' end of the ORF of Bmi-) and the 3'-UTR of Bmi-1 or a fragment, mutant or post-transcriptional regulatory element thereof, wherein the reporter gene is in frame with the amino terminal and carboxy terminal fragments of the ORF of Bmi-1 and the reporter gene lacks an endogenous stop codon, and wherein the 5'-UTR of Bmi-1 or a fragment, mutant or post-transcriptional regulatory element thereof and the amino terminal fragment of the Bmi-1 ORF are upstream of the reporter gene, and the carboxy terminal fragment of the ORF of Bmi-1 and the 3'-UTR or fragment, mutant or post-transcriptional regulatory element thereof are downstream of the reporter gene. In certain embodiments, the reporter gene lacks an endogenous start codon. In specific embodiments, the nucleic acid construct comprises the 5'-UTR of human Bmi-1 and 21 nucleotides of the ORF from the 5' end of human Bmi-1. In another specific embodiment, the nucleic acid construct comprises nucleic acid residues 1 to 505 of the 5'-UTR of human Bmi-1 and 21 nucleotides of the ORF from the 5' end of human Bmi-1. In other specific embodiments, the nucleic acid construct comprises the last 21 nucleotides of the ORF from the 3' end of human Bmi-1 and the 3'-UTR of human Bmi-1.

The methods described herein are also directed to a vector comprising a nucleic acid construct described herein. In a particular embodiment, the vector comprises a nucleic acid construct, wherein the nucleic acid construct comprises a reporter gene operably linked to (i) the 5'-UTR of Bmi-1 or a fragment, mutant or post-transcriptional regulatory element thereof and the 3'-UTR of Bmi-1 or a fragment, mutant or post-transcriptional regulatory element thereof; or (ii) the 5'-UTR of Bmi-1 or a fragment, mutant or post-transcriptional regulatory element thereof; or (iii) the 3'-UTR of Bmi-1 or a fragment, mutant or post-transcriptional regulatory element thereof, wherein the 5' UTR or fragment, mutant or post-transcriptional regulatory element thereof is upstream of the reporter gene and the 3' UTR or fragment, mutant or post-transcriptional regulatory element thereof is downstream of the reporter gene.

The methods described herein also provide for a host cell containing a vector described herein. In one embodiment, the host cell contains a vector comprising a nucleic acid construct, wherein the nucleic acid construct comprises a reporter gene operably linked to (i) the 5'-UTR of Bmi-1 or a fragment, mutant or post-transcriptional regulatory element thereof and the 3'-UTR of Bmi-1 or a fragment, mutant or post-transcriptional regulatory element thereof; or (ii) the 5'-UTR of Bmi-1 or a fragment, mutant or post-transcriptional regulatory element thereof; or (iii) the 3'-UTR of Bmi-1 or a fragment, mutant or post-transcriptional regulatory element thereof, wherein the 5' UTR or fragment, mutant or post-transcriptional regulatory element thereof is upstream of the reporter gene and the 3' UTR or fragment, mutant or post-transcriptional regulatory element thereof is downstream of the reporter gene.

In some embodiments, a host cell contains a vector comprising a nucleic acid construct, wherein the nucleic acid construct comprises a reporter gene operably linked to the 5'-UTR of Bmi-1 or a fragment, mutant or post-transcriptional regulatory element thereof and an amino terminal fragment of the Bmi-1 ORF, (e.g., the first 3, 6, 9, 12, 15, 18, 21, 24, or more nucleotides from the 5' end of the ORF of Bmi-1), wherein the reporter gene is in frame with the amino terminal fragment of the ORF of Bmi-1, and wherein the 5'-UTR of Bmi-1 or a fragment, mutant or post-transcriptional regulatory element thereof and the amino terminal fragment of the Bmi-1 ORF are upstream of the reporter gene. In certain embodiments, the reporter gene lacks an endogenous start codon. In specific embodiments, the nucleic acid construct comprises the 5'-UTR of human Bmi-1 and the first 21 nucleotides of the ORF from the 5' end of human Bmi-1. In other specific embodiments, the nucleic acid construct comprises nucleic acid residues 1 to 505 of the 5'-UTR of human Bmi-1 and the first 21 nucleotides of the ORF from the 5' end of human Bmi-1.

In some embodiments, a host cell contains a vector comprising a nucleic acid construct, wherein the nucleic acid construct comprises a reporter gene operably linked to a carboxy terminal fragment of the Bmi-1 ORF (e.g., the last 3, 6, 9, 12, 15, 18, 21, 24, or more nucleotides from the 3' end of the ORF of Bmi-1) and the 3'-UTR of Bmi-1 or a fragment, mutant or post-transcriptional regulatory element thereof, wherein the reporter gene is in frame with the carboxy terminal fragment of the Bmi-1 ORF and the reporter gene lacks an endogenous stop codon, and wherein the carboxy terminal fragment of the ORF of Bmi-1 are downstream of the reporter gene and the 3'-UTR of Bmi-1 or a fragment, mutant or post-transcriptional regulatory element thereof. In specific embodiments, the nucleic acid construct comprises the last 21 nucleotides of the ORF from the 3' end of human Bmi-1 and the 3'-UTR of Bmi-1 or a fragment, mutant or post-transcriptional regulatory element thereof.

In some embodiments, a host cell contains a vector comprising a nucleic acid construct, wherein the nucleic acid construct comprises a reporter gene operably linked to (i) the 5'-UTR of Bmi-1 or a fragment, mutant or post-transcriptional regulatory element thereof and an amino terminal fragment of the Bmi-1 ORF, (e.g., the first 3, 6, 9, 12, 15, 18, 21, 24, or more nucleotides from the 5' end of the ORF of Bmi-1); and (ii) a carboxy terminal fragment of the Bmi-1 ORF (e.g., the last 3, 6, 9, 12, 15, 18, 21, 24, or more nucleotides from the 3' end of the ORF of Bmi-) and the 3'-UTR of Bmi-1 or a fragment, mutant or post-transcriptional regulatory element thereof, wherein the reporter gene is in frame with the amino terminal and carboxy terminal fragments of the ORF of Bmi-1 and the reporter gene lacks an endogenous stop codon, and wherein the 5'-UTR of Bmi-1 or a fragment, mutant or post-transcriptional regulatory element thereof and the amino terminal fragment of the Bmi-1 ORF are upstream of the reporter gene, and the carboxy terminal fragment of the ORF of Bmi-1 and the 3'-UTR of Bmi-1 or a fragment, mutant or post-transcriptional regulatory element thereof are downstream of the reporter gene. In certain embodiments, the reporter gene lacks an endogenous start codon. In specific embodiments, the nucleic acid construct comprises nucleic acid residues 1 to 505 of the 5'-UTR of human Bmi-1 and the first 21 nucleotides of the ORF from the 5' end of human Bmi-1. In other specific embodiments, the nucleic acid construct comprises the last 21 nucleotides of the ORF from the 3' end of human Bmi-1 and the 3'-UTR of Bmi-1 or a fragment, mutant or post-transcriptional regulatory element thereof.

The methods described herein also encompass a cell-free extract containing a mRNA transcribed from the nucleic acid construct described herein, wherein the nucleic acid construct is DNA. In a specific embodiment, the cell-free extract contains a mRNA transcribed from a DNA nucleic acid construct comprising a reporter gene operably linked to (i) the 5'-UTR of Bmi-1 or a fragment, mutant or post-transcriptional regulatory element thereof and the 3'-UTR of Bmi-1 or a fragment, mutant or post-transcriptional regulatory element thereof; or (ii) the 5'-UTR of Bmi-1 or a fragment, mutant or post-transcriptional regulatory element thereof; or (iii) the 3'-UTR of Bmi-1 or a fragment, mutant or post-transcriptional regulatory element thereof, wherein the 5' UTR or fragment, mutant or post-transcriptional regulatory element thereof is upstream of the reporter gene and the 3' UTR or fragment, mutant or post-transcriptional regulatory element thereof is downstream of the reporter gene.

In one embodiment, the methods described herein provide a method for identifying or validating a compound that modulates UTR-dependent expression of Bmi-1 comprising the steps of: (a) contacting a compound with a host cell containing a nucleic acid construct comprising a reporter gene operably linked to (i) the 5'-UTR of the Bmi-1 gene or a fragment, mutant or post-transcriptional regulatory element thereof and the 3'-UTR of the Bmi-1 gene or a fragment, mutant or post-transcriptional regulatory element thereof; or (ii) the 5'-UTR of the Bmi-1 gene or a fragment, mutant or post-transcriptional regulatory element thereof; or (iii) the 3'-UTR of the Bmi-1 gene or a fragment, mutant or post-transcriptional regulatory element thereof, wherein the 5'-UTR or fragment, mutant or post-transcriptional regulatory element thereof is upstream of the reporter gene and the 3'-UTR or fragment, mutant or post-transcriptional regulatory element thereof is downstream of the reporter gene; and (b) detecting the amount or activity of a reporter protein translated from a mRNA transcript transcribed from said reporter gene, wherein a compound that modulates UTR-dependent expression of Bmi-1 is identified or validated if the amount or activity of said reporter protein detected in the presence of the compound is altered relative to a previously determined reference range, or relative to the amount or activity of said reporter protein detected in the absence of said compound or the presence of a negative control.

In another embodiment, the methods described herein provides a method for identifying or validating a compound that modulates UTR-dependent expression of Bmi-1 comprising the steps of (a) contacting a compound with a host cell containing a nucleic acid construct comprising a reporter gene operably linked to the 5'-UTR of Bmi-1 or a fragment, mutant or post-transcriptional regulatory element thereof and an amino terminal fragment of the Bmi-1 ORF, (e.g., the first 3, 6, 9, 12, 15, 18, 21, 24, or more nucleotides from the 5' end of the ORF of Bmi-1), wherein the reporter gene is in frame with the amino terminal fragment of the ORF of Bmi-1, and wherein the 5'-UTR of Bmi-1 or a fragment, mutant or post-transcriptional regulatory element thereof and the amino terminal fragment of the Bmi-1 ORF are upstream of the reporter gene; and (b) detecting the amount or activity of a reporter protein translated from a mRNA transcript transcribed from said reporter gene, wherein a compound that modulates UTR-dependent expression of Bmi-1 is identified or validated if the amount or activity of said reporter protein detected in the presence of the compound is altered relative to a previously determined reference range, or relative to the amount or activity of said reporter protein detected in the absence of said compound or the presence of a negative control. In one embodiment, a compound that down-regulates UTR-dependent expression of Bmi-1 is identified or validated if the amount or activity of said reporter protein detected in the presence of the compound is down-regulated or reduced relative to a previously determined reference range, or relative to the amount or activity of said reporter protein detected in the absence of said compound or the presence of a negative control. In certain embodiments, the reporter gene lacks an endogenous start codon. In specific embodiments, the nucleic acid construct comprises the 5'-UTR of human Bmi-1 and the first 21 nucleotides of the ORF from the 5' end of human Bmi-1. In another specific embodiment, the nucleic acid construct comprises nucleic acid residues 1 to 505 of the 5'-UTR of human Bmi-1 and the first 21 nucleotides of the ORF from the 5' end of human Bmi-1.

In another embodiment, the methods described herein provide a method for identifying or validating a compound that modulates UTR-dependent expression of Bmi-1 comprising the steps of: (a) contacting a compound with a host cell containing a nucleic acid construct comprising a reporter gene operably linked to a carboxy terminal fragment of the Bmi-1 ORF (e.g., the last 3, 6, 9, 12, 15, 18, 21, 24, or more nucleotides from the 3' end of the ORF of Bmi-1) and the 3'-UTR of Bmi-1 or a fragment, mutant or post-transcriptional regulatory element thereof, wherein the reporter gene is in frame with the carboxy terminal fragment of the Bmi-1 ORF and the reporter gene lacks an endogenous stop codon, and wherein the carboxy terminal fragment of the ORF of Bmi-1 and the 3'-UTR of Bmi-1 or a fragment, mutant or post-transcriptional regulatory element thereof are downstream of the reporter gene; and (b) detecting the amount or activity of a reporter protein translated from a mRNA transcript transcribed from said reporter gene, wherein a compound that modulates UTR-dependent expression of Bmi-1 is identified or validated if the amount or activity of said reporter protein detected in the presence of the compound is altered relative to a previously determined reference range, or relative to the amount or activity of said reporter protein detected in the absence of said compound or the presence of a negative control. In one embodiment, a compound that down-regulates UTR-dependent expression of Bmi-1 is identified or validated if the amount or activity of said reporter protein detected in the presence of the compound is down-regulated or reduced relative to a previously determined reference range, or relative to the amount or activity of said reporter protein detected in the absence of said compound or the presence of a negative control.

In another embodiment, the methods described herein provide a method for identifying or validating a compound that modulates UTR-dependent expression of Bmi-1 comprising the steps of: (a) contacting a compound with a host cell containing a nucleic acid construct comprising a reporter gene operably linked to (i) the 5'-UTR of Bmi-1 or a fragment, mutant or post-transcriptional regulatory element thereof and an amino terminal fragment of the Bmi-1 ORF, (e.g., the first 3, 6, 9, 12, 15, 18, 21, 24, or more nucleotides from the 5' end of the ORF of Bmi-1); and (ii) a carboxy terminal fragment of the Bmi-1 ORF (e.g., the last 3, 6, 9, 12, 15, 18, 21, 24, or more nucleotides from the 3' end of the ORF of Bmi-1) and the 3'-UTR or fragment, mutant or post-transcriptional regulatory element thereof, wherein the reporter gene is in frame with the amino terminal and carboxy terminal fragments of the ORF of Bmi-1 and the reporter gene lacks an endogenous stop codon, and wherein the 5'-UTR of Bmi-1 or a fragment, mutant or post-transcriptional regulatory element thereof and the amino terminal fragment of the Bmi-1 ORF are upstream of the reporter gene, and the carboxy terminal fragment of the ORF of Bmi-1 and the 3'-UTR or fragment, mutant or post-transcriptional regulatory element thereof are downstream of the reporter gene; and (b) detecting the amount or activity of a reporter protein translated from a mRNA transcript transcribed from said reporter gene, wherein a compound that modulates UTR-dependent expression of Bmi-1 is identified or validated if the amount or activity of said reporter protein detected in the presence of the compound is altered relative to a previously determined reference range, or relative to the amount or activity of said reporter protein detected in the absence of said compound or the presence of a negative control. In one embodiment, a compound that down-regulates UTR-dependent expression of Bmi-1 is identified or validated if the amount or activity of said reporter protein detected in the presence of the compound is down-regulated or reduced relative to a previously determined reference range, or relative to the amount or activity of said reporter protein detected in the absence of said compound or the presence of a negative control. In certain embodiments, the reporter gene lacks an endogenous start codon. In specific embodiments, the nucleic acid construct comprises the 5'-UTR of human Bmi-1 and the first 21 nucleotides of the ORF from the 5' end of human Bmi-1. In another specific embodiment, the nucleic acid construct comprises nucleic acid residues 1 to 505 of the 5'-UTR of human Bmi-1 and the first 21 nucleotides of the ORF from the 5' end of human Bmi-1. In other specific embodiments, the nucleic acid construct comprises the last 21 nucleotides of the ORF from the 3' end of human Bmi-1 and the 3'-UTR of Bmi-1 or a fragment, mutant or post-transcriptional regulatory element thereof.

In a particular embodiment, the methods described herein relate to a method for identifying or validating a compound that down-regulates or reduces UTR-dependent expression of Bmi-1, comprising the steps of: (a) contacting a compound with the host cell containing a nucleic acid construct comprising a reporter gene operably linked to (i) the 5'-UTR of the Bmi-1 gene or a fragment, mutant or post-transcriptional regulatory element thereof and the 3'-UTR of the Bmi-1 gene or a fragment, mutant or post-transcriptional regulatory element thereof; or (ii) the 5'-UTR of the Bmi-1 gene or a fragment, mutant or post-transcriptional regulatory element thereof; or (iii) the 3'-UTR of the Bmi-1 gene or a fragment, mutant or post-transcriptional regulatory element thereof, wherein the 5'-UTR or fragment, mutant or post-transcriptional regulatory element thereof is upstream of the reporter gene and the 3'-UTR or fragment, mutant or post-transcriptional regulatory element thereof is downstream of the reporter gene; and (b) detecting the amount or activity of a reporter protein translated from a mRNA transcript transcribed from said reporter gene, and wherein a compound that modulates UTR-dependent expression of Bmi-1 is identified or validated if the amount or activity of said reporter protein detected in the presence of the compound is down-regulated or reduced relative to a previously determined reference range, or relative to the amount or activity of said reporter protein detected in the absence of said compound or the presence of a negative control. In a specific embodiment, the previously determined reference range is the amount or activity of the reporter protein detected in the presence of a negative control (e.g., PBS or DMSO).

In some embodiments, the methods described herein relate to a method for identifying or validating a compound that modulates UTR dependent expression of Bmi-1 comprising the steps of: (a) contacting a compound with a cell-free extract containing a mRNA transcribed from a DNA nucleic acid construct comprising a reporter gene operably linked to (i) the 5'-UTR of the Bmi-1 gene or a fragment, mutant or post-transcriptional regulatory element thereof and the 3'-UTR of the Bmi-1 gene or a fragment, mutant or post-transcriptional regulatory element thereof; or (ii) the 5'-UTR of Bmi-1 or a fragment, mutant or post-transcriptional regulatory element thereof; or (iii) the 3'-UTR of Bmi-1 or a fragment, mutant or post-transcriptional regulatory element thereof, wherein the 5'-UTR or fragment, mutant or post-transcriptional regulatory element thereof is upstream of the reporter gene and the 3'-UTR or fragment, mutant or post-transcriptional regulatory element thereof is downstream of the reporter gene; and (b) detecting the amount or activity of a reporter protein translated from said mRNA, wherein a compound that modulates UTR-dependent expression of Bmi-1 is identified or validated if the amount or activity of the reporter protein detected in the presence of the compound is altered relative to a previously determined reference range or relative to the amount or activity of the reporter protein detected in the absence of the compound or the presence of a negative control.

In a specific embodiment, the methods described herein relate to a method for identifying or validating a compound that down-regulates or reduces UTR dependent expression of Bmi-1 comprising the steps of: (a) contacting a compound with a cell-free extract containing a mRNA transcribed from a DNA nucleic acid construct comprising a reporter gene operably linked to (i) the 5'-UTR of the Bmi-1 gene or a fragment, mutant or post-transcriptional regulatory element thereof and the 3'-UTR of the Bmi-1 gene or a fragment, mutant or post-transcriptional regulatory element thereof; or (ii) the 5'-UTR of Bmi-1 or a fragment, mutant or post-transcriptional regulatory element thereof; or (iii) the 3'-UTR of Bmi-1 or a fragment, mutant or post-transcriptional regulatory element thereof, wherein the 5'-UTR or fragment, mutant or post-transcriptional regulatory element thereof is upstream of the reporter gene and the 3'-UTR or fragment, mutant or post-transcriptional regulatory element thereof is downstream of the reporter gene; and (b) detecting the amount or activity of a reporter protein translated from said mRNA, wherein a compound that down-regulates or reduces UTR-dependent expression of Bmi-1 is identified or validated if the amount or activity of said reporter protein detected in the presence of the compound is down-regulated or reduced relative to a previously determined reference range or relative to the amount or activity of said reporter protein detected in the absence of said compound or the presence of a negative control. In a specific embodiment, the previously determined reference range is the amount or activity of the reporter protein detected in the presence of a negative control (e.g., PBS or DMSO).

In some embodiments, the methods described herein relate to a method for identifying or validating a compound that modulates UTR dependent expression of Bmi-1 comprising the steps of: (a) contacting a compound with a cell-free extract containing a mRNA transcribed from a DNA nucleic acid construct comprising a reporter gene operably linked to the 5'-UTR of Bmi-1 or a fragment, mutant or post-transcriptional regulatory element thereof and an amino terminal fragment of the Bmi-1 ORF, (e.g., the first 3, 6, 9, 12, 15, 18, 21, 24, or more nucleotides from the 5' end of the ORF of Bmi-1), wherein the reporter gene is in frame with the amino terminal fragment of the ORF of Bmi-1, and wherein the 5'-UTR of Bmi-1 or a fragment, mutant or post-transcriptional regulatory element thereof and the amino terminal fragment of the Bmi-1 ORF are upstream of the reporter gene; and (b) detecting the amount or activity of a reporter protein translated from said mRNA, wherein a compound that modulates UTR-dependent expression of Bmi-1 is identified or validated if the amount or activity of said reporter protein detected in the presence of the compound is altered relative to a previously determined reference range or relative to the amount or activity of said reporter protein detected in the absence of said compound or the presence of a negative control. In one embodiment, a compound that down-regulates UTR-dependent expression of Bmi-1 is identified or validated if the amount or activity of said reporter protein detected in the presence of the compound is down-regulated or reduced relative to a previously determined reference range, or relative to the amount or activity of said reporter protein detected in the absence of said compound or the presence of a negative control. In certain embodiments, the reporter gene lacks an endogenous start codon. In specific embodiments, the nucleic acid construct comprises the 5'-UTR of human Bmi-1 and the first 21 nucleotides of the ORF from the 5' end of human Bmi-1. In specific embodiments, the nucleic acid construct comprises nucleic acid residues 1 to 505 of the 5'-UTR of human Bmi-1 and the first 21 nucleotides of the ORF from the 5' end of human Bmi-1.

In some embodiments, the methods described herein relate to a method for identifying or validating a compound that modulates UTR dependent expression of Bmi-1 comprising the steps of: (a) contacting a compound with a cell-free extract containing a mRNA transcribed from a DNA nucleic acid construct comprising a reporter gene operably linked to a carboxy terminal fragment of the Bmi-1 ORF (e.g., the last 3, 6, 9, 12, 15, 18, 21, 24, or more nucleotides from the 3' end of the ORF of Bmi-1) and the 3'-UTR of Bmi-1 or a fragment, mutant or post-transcriptional regulatory element thereof, wherein the reporter gene is in frame with the carboxy terminal fragment of the Bmi-1 ORF and the reporter gene lacks an endogenous stop codon, and wherein the carboxy terminal fragment of the ORF of Bmi-1 and the 3'-UTR of Bmi-1 or a fragment, mutant or post-transcriptional regulatory element thereof are downstream of the reporter gene; and (b) detecting the amount or activity of a reporter protein translated from said mRNA, wherein a compound that modulates UTR-dependent expression of Bmi-1 is identified or validated if the amount or activity of said reporter protein detected in the presence of the compound is altered relative to a previously determined reference range or relative to the amount or activity of said reporter protein detected in the absence of said compound or the presence of a negative control. In one embodiment, a compound that down-regulates UTR-dependent expression of Bmi-1 is identified or validated if the amount or activity of said reporter protein detected in the presence of the compound is down-regulated or reduced relative to a previously determined reference range, or relative to the amount or activity of said reporter protein detected in the absence of said compound or the presence of a negative control.

In some embodiments, the methods described herein relate to a method for identifying or validating a compound that modulates UTR dependent expression of Bmi-1 comprising the steps of: (a) contacting a compound with a cell-free extract containing a mRNA transcribed from a DNA nucleic acid construct comprising a reporter gene operably linked to (i) the 5'-UTR of Bmi-1 or a fragment, mutant or post-transcriptional regulatory element thereof and an amino terminal fragment of the Bmi-1 ORF, (e.g., the first 3, 6, 9, 12, 15, 18, 21, 24, or more nucleotides from the 5' end of the ORF of Bmi-1); and (ii) a carboxy terminal fragment of the Bmi-1 ORF (e.g., the last 3, 6, 9, 12, 15, 18, 21, 24, or more nucleotides from the 3' end of the ORF of Bmi-1) and the 3'-UTR of Bmi-1 or a fragment, mutant or post-transcriptional regulatory element thereof, wherein the reporter gene is in frame with the amino terminal and carboxy terminal fragments of the ORF of Bmi-1 and the reporter gene lacks an endogenous stop codon, and wherein the 5'-UTR of Bmi-1 or a fragment, mutant or post-transcriptional regulatory element thereof and the amino terminal fragment of the Bmi-1 ORF are upstream of the reporter gene, and the carboxy terminal fragment of the ORF of Bmi-1 and the 3'-UTR of Bmi-1 or a fragment, mutant or post-transcriptional regulatory element thereof are downstream of the reporter gene; and (b) detecting the amount or activity of a reporter protein translated from said mRNA, wherein a compound that modulates UTR-dependent expression of Bmi-1 is identified or validated if the amount or activity of said reporter protein detected in the presence of the compound is altered relative to a previously determined reference range or relative to the amount or activity of said reporter protein detected in the absence of said compound or the presence of a negative control. In one embodiment, a compound that down-regulates UTR-dependent expression of Bmi-1 is identified or validated if the amount or activity of said reporter protein detected in the presence of the compound is down-regulated or reduced relative to a previously determined reference range, or relative to the amount or activity of said reporter protein detected in the absence of said compound or the presence of a negative control. In certain embodiments, the reporter gene lacks an endogenous start codon. In specific embodiments, the nucleic acid construct comprises the 5'-UTR of human Bmi-1 and the first 21 nucleotides of the ORF from the 5' end of human Bmi-1. In another specific embodiment, the nucleic acid construct comprises nucleic acid residues 1 to 505 of the 5'-UTR of human Bmi-1 and the first 21 nucleotides of the ORF from the 5' end of human Bmi-1. In other specific embodiments, the nucleic acid construct comprises the last 21 nucleotides of the ORF from the 3' end of human Bmi-1 and the 3'-UTR of Bmi-1 or a fragment, mutant or post-transcriptional regulatory element thereof.

In certain embodiments, compounds identified or validated using the high throughput screening methods described herein stabilize or enhance the activity of either inhibitory cis-elements, or trans-regulatory complexes bind to such inhibitory cis-elements in any of the Bmi-1 5'-UTR and 3'-UTR, or the Bmi-1 5'-UTR or the Bmi-1 3'-UTR and decrease or down-regulate post-transcriptional expression of Bmi-1. In certain embodiments, compounds identified or validated using the high throughput screening methods described herein destabilize or decrease or down-regulate the activity of enhancer cis-elements, or trans-regulatory complexes that bind to such enhancer cis-elements in any of the Bmi-1 5'-UTR and 3'-UTR, or the Bmi-1 5'-UTR or the Bmi-1 3'-UTR and decrease or down-regulate post-transcriptional expression of Bmi-1.

In one embodiment, the methods described herein provide for a bicistronic nucleic acid construct comprising in the following 5' to 3' order, a cap, a promoter, a first reporter gene encoding or coding for a first reporter protein mRNA transcript, a 5'-UTR of Bmi-1 or a fragment, mutant or post-transcriptional regulatory element thereof, comprising the IRES sequence of the 5'-UTR of Bmi-1, and a second reporter gene encoding or coding for a second reporter protein mRNA transcript, wherein the translation of the first reporter protein mRNA transcript encoded by the first reporter gene is CAP-dependent/initiated and the translation of the second reporter protein mRNA transcript encoded by the second reporter gene is IRES-dependent/initiated.

In one embodiment, the methods described herein provide for a bicistronic nucleic acid construct comprising in the following 5' to 3' order, a cap, a promoter, a first reporter gene encoding or coding for a first reporter protein mRNA transcript, a 5'-UTR of Bmi-1 or a fragment, mutant or post-transcriptional regulatory element thereof, comprising the IRES sequence of the 5'-UTR of Bmi-1, an amino terminal fragment of the Bmi-1 ORF (e.g., the first 3, 6, 9, 12, 15, 18, 21, 24, or more nucleotides of the from the 5' of the ORF of Bmi-1) and a second reporter gene encoding or coding for a second reporter protein mRNA transcript, wherein the amino terminal fragment of the Bmi-1 ORF is in frame with the second reporter gene and wherein the translation of the first reporter protein mRNA transcript encoded by the first reporter gene is CAP-dependent/initiated and the translation of the second reporter protein mRNA transcript encoded by the second reporter gene is IRES-dependent/initiated.

In one embodiment, the methods described herein provide for a bicistronic nucleic acid construct comprising in the following 5' to 3' order, a cap, a promoter, a first reporter gene encoding or coding for a first reporter protein mRNA transcript, a 5'-UTR of Bmi-1 or a fragment, mutant or post-transcriptional regulatory element thereof, comprising the IRES sequence of the 5'-UTR of Bmi-1, a second reporter gene encoding or coding for a second reporter protein mRNA transcript, and optionally, a 3'-UTR that is different from the 3-UTR of Bmi-1 or a fragment, mutant or post-transcriptional regulatory element thereof, wherein the translation of the first reporter protein mRNA transcript encoded by the first reporter gene is CAP-dependent/initiated and the translation of the second reporter protein mRNA transcript encoded by the second reporter gene is IRES-dependent/initiated.

In some embodiments, the methods described herein provide a bicistronic nucleic acid construct comprising in the following 5' to 3' order: a cap, a promoter, a first reporter gene encoding or coding for a first reporter protein mRNA transcript, a 5'-UTR of Bmi-1 or a fragment thereof comprising the IRES sequence of the 5'-UTR of Bmi-1, an amino terminal fragment of the Bmi-1 ORF (e.g., the first 3, 6, 9, 12, 15, 18, 21, 24, or more nucleotides of the from the 5' of the ORF of Bmi-1), a second reporter gene encoding or coding for a second reporter protein mRNA transcript, and optionally, a 3'-UTR that is different from the 3'-UTR of Bmi-1 or a fragment, mutant or post-transcriptional regulatory element thereof, wherein the amino terminal fragment of the Bmi-1 ORF is in frame with the second reporter gene and wherein the translation of the first reporter protein mRNA transcript encoded by the first reporter gene is CAP-dependent/initiated and the translation of the second reporter protein mRNA transcript encoded by the second reporter gene is IRES-dependent/initiated.

In some embodiments, the methods described herein relate to a method for identifying or validating a compound that modulates IRES-dependent translation activity of Bmi-1 while leaving CAP-dependent translation activity of Bmi-1 unaffected, said method comprising: (a) contacting a compound with a host cell containing a bicistronic nucleic acid construct expressing a first reporter protein and a second reporter protein, wherein said bicistronic nucleic acid construct comprises, in the following 5' to 3' order, a cap, a promoter, a first reporter gene encoding or coding for a first reporter protein mRNA transcript, a 5'-UTR of Bmi-1 or a fragment thereof comprising the IRES sequence of the 5'-UTR of Bmi-1, and a second reporter gene encoding or coding for a second reporter protein mRNA transcript, and wherein the translation of the first reporter protein mRNA transcript encoded by the first reporter gene is CAP-dependent/initiated and the translation of the second reporter protein mRNA transcript encoded by the second reporter gene is IRES-dependent/initiated; and (b) detecting the amount or activity of the first and second reporter proteins, wherein a compound that modulates IRES-dependent translation activity of Bmi-1 while leaving CAP-dependent translation activity of Bmi-1 unaffected is identified or validated if (i) the amount or activity of the first reporter protein detected in the presence of the compound is not altered or not significantly altered relative to the amount or activity of the first reporter protein detected in the absence of the compound or the presence of a negative control, or relative to a previously determined reference range, and (ii) the amount or activity of the second reporter protein detected in the presence of the compound is significantly altered relative to the amount or activity of the second reporter protein detected in the absence of the compound or the presence of a negative control, or relative to a previously determined reference range. In a specific embodiment, the previously determined reference range is the amount or activity of the reporter protein detected in the presence of a negative control (e.g., PBS or DMSO).

In some embodiments, the methods described herein relate to a method for identifying or validating a compound that modulates IRES-dependent translation activity of Bmi-1 while leaving CAP-dependent translation activity of Bmi-1 unaffected, said method comprising: (a) contacting a compound with a host cell containing a bicistronic nucleic acid construct expressing a first reporter protein and a second reporter protein, wherein said bicistronic nucleic acid construct comprises, in the following 5' to 3' order, a cap, a promoter, a first reporter gene encoding or coding for a first reporter protein mRNA transcript, a 5'-UTR of Bmi-1 or a fragment thereof comprising the IRES sequence of the 5'-UTR of Bmi-1, an amino terminal fragment of the Bmi-1 ORF (e.g., the first 3, 6, 9, 12, 15, 18, 21, 24, or more nucleotides from the 5' end of the ORF of Bmi-1), and a second reporter gene encoding or coding for a second reporter protein mRNA transcript, wherein the amino terminal fragment of the Bmi-1 ORF is in frame with the second reporter gene, and wherein the translation of the first reporter protein mRNA transcript encoded by the first reporter gene is CAP-dependent/initiated and the translation of the second reporter protein mRNA transcript encoded by the second reporter gene is IRES-dependent/initiated; and (b) detecting the amount or activity of the first and second reporter proteins, wherein a compound that modulates IRES-dependent translation activity of Bmi-1 while leaving CAP-dependent translation activity of Bmi-1 unaffected is identified or validated if (i) the amount or activity of the first reporter protein detected in the presence of the compound is not altered or not significantly altered relative to the amount or activity of the first reporter protein detected in the absence of the compound or the presence of a negative control, or relative to a previously determined reference range, and (ii) the amount or activity of the second reporter protein detected in the presence of the compound is significantly altered relative to the amount or activity of the second reporter protein detected in the absence of the compound or the presence of a negative control, or relative to a previously determined reference range. In a specific embodiment, the previously determined reference range is the amount or activity of the reporter protein detected in the presence of a negative control (e.g., PBS or DMSO). In certain embodiments, the reporter gene lacks an endogenous start codon. In specific embodiments, the nucleic acid construct comprises the 5'-UTR of human Bmi-1 and the first 21 nucleotides of the ORF from the 5' end of human Bmi-1. In another specific embodiment, the nucleic acid construct comprises nucleic acid residues 1 to 505 of the 5'-UTR of human Bmi-1 and the first 21 nucleotides of the ORF from the 5' end of human Bmi-1.

In some embodiments, the methods described herein relate to a method for identifying or validating a compound that modulates IRES-dependent translation activity of Bmi-1 while leaving CAP-dependent translation activity of Bmi-1 unaffected, said method comprising: (a) contacting a compound with a cell-free extract and a bicistronic nucleic acid construct expressing a first reporter protein and a second reporter protein, wherein said bicistronic nucleic acid construct comprises, in the following 5' to 3' order, a cap, a promoter, a first reporter gene encoding or coding for a first reporter protein mRNA transcript, a 5'-UTR of Bmi-1 or a fragment thereof comprising the IRES sequence of the 5'-UTR of Bmi-1, and a second reporter gene encoding or coding for a second reporter protein mRNA transcript, and wherein the translation of the first reporter protein mRNA transcript encoded by the first reporter gene is CAP-dependent/initiated and the translation of the second reporter protein mRNA transcript encoded by the second reporter gene is IRES-dependent/initiated; and (b) detecting the amount or activity of the first and second reporter proteins translated from the first and second reporter genes, respectively, wherein a compound that modulates IRES-dependent translation activity of Bmi-1 while leaving CAP-dependent translation activity of Bmi-1 unaffected is identified or validated if: (i) the amount or activity of the first reporter protein detected in the presence of the compound is not altered or not significantly altered relative to the amount or activity of the first reporter protein detected in the absence of the compound or the presence of a negative control, or relative to a previously determined reference range, and (ii) the amount or activity of the second reporter protein detected in the presence of the compound is significantly altered relative to the amount or activity of the second reporter protein detected in the absence of the compound or the presence of a negative control, or relative to a previously determined reference range. In a specific embodiment, the previously determined reference range is the amount or activity of the reporter protein detected in the presence of a negative control (e.g., PBS or DMSO).

In some embodiments, the methods described herein relate to a method for identifying or validating a compound that modulates IRES-dependent translation activity of Bmi-1 while leaving CAP-dependent translation activity of Bmi-1 unaffected, said method comprising: (a) contacting a compound with a cell-free extract and a bicistronic nucleic acid construct expressing a first reporter protein and a second reporter protein, wherein said bicistronic nucleic acid construct comprises, in the following 5' to 3' order, a cap, a promoter, a first reporter gene encoding or coding for a first reporter protein mRNA transcript, a 5'-UTR of Bmi-1 or a fragment thereof comprising the IRES sequence of the 5'-UTR of Bmi-1, an amino terminal fragment of the Bmi-1 ORF, (e.g., the first 3, 6, 9, 12, 15, 18, 21, 24, or more nucleotides from the 5' end of the ORF of Bmi-1), and a second reporter gene encoding or coding for a second reporter protein mRNA transcript, wherein the amino terminal fragment of the Bmi-1 ORF is in frame with the second reporter gene, and wherein the translation of the first reporter protein mRNA transcript encoded by the first reporter gene is CAP-dependent/initiated and the translation of the second reporter protein mRNA transcript encoded by the second reporter gene is IRES-dependent/initiated; and (b) detecting the amount or activity of the first and second reporter proteins translated from the first and second reporter genes, respectively, wherein a compound that modulates IRES-dependent translation activity of Bmi-1 while leaving CAP-dependent translation activity of Bmi-1 unaffected is identified or validated if: (i) the amount or activity of the first reporter protein detected in the presence of the compound is not altered or not significantly altered relative to the amount or activity of the first reporter protein detected in the absence of the compound or the presence of a negative control, or relative to a previously determined reference range, and (ii) the amount or activity of the second reporter protein detected in the presence of the compound is significantly altered relative to the amount or activity of the second reporter protein detected in the absence of the compound or the presence of a negative control, or relative to a previously determined reference range. In a specific embodiment, the previously determined reference range is the amount or activity of the reporter protein detected in the presence of a negative control (e.g., PBS or DMSO). In certain embodiments, the reporter gene lacks an endogenous start codon. In specific embodiments, the nucleic acid construct comprises the 5'-UTR of human Bmi-1 and the first 21 nucleotides of the ORF from the 5' end of human Bmi-1. In another specific embodiment, the nucleic acid construct comprises nucleic acid residues 1 to 505 of the 5'-UTR of human Bmi-1 and the first 21 nucleotides of the ORF from the 5' end of human Bmi-1.

The methods described herein are based, in part, on the Applicants' discovery that the 3'-UTR of Bmi-1 mRNA stimulates post-transcriptional expression of Bmi-1, whereas the 5'-UTR of Bmi-1 mRNA suppresses the stimulating effect of the 3'-UTR of Bmi-1. Alternative translation initiation is operative in the 5'-UTR of Bmi-1 due to the presence of an internal ribosomal entry site (IRES) in the 5'-UTR of Bmi-1. Compounds that down-regulate or reduce the activity of the Bmi-1 3'-UTR are expected to decrease or down-regulate the expression of Bmi-1 protein post-transcriptionally. Compounds that stabilize the structure and down-regulate or decrease the activity of the Bmi-1 5'-UTR are expected to decrease or down-regulate the expression of Bmi-1 protein post-transcriptionally. Compounds that simultaneously down-regulate the activity of the Bmi-1 3'-UTR and down-regulate the activity of the Bmi-1 5'-UTR are expected to decrease or down-regulate the expression of Bmi-1 protein post-transcriptionally. Without being bound by theory, the interaction of the compound with the 5'-UTR and 3'-UTR, or the 5'-UTR or the 3'-UTR of Bmi-1 disrupts the interaction between and the function of the 5'-UTR and 3'-UTR, or the 5'-UTR or the 3'-UTR of Bmi-1.

The UTR targeted approach of the methods described herein has several advantages. In particular, the sequences of the 5'-UTR and 3'-UTR appear to be unique to the Bmi-1 transcripts. Therefore, compounds that are highly specific for these UTRs can be used to selectively down-regulate post-transcriptional expression of Bmi-1 by disrupting the interaction between the 5'-UTR and 3'-UTR, or the function of the 5'-UTR or the function of the 3'-UTR of Bmi-1. Further, down-regulating the post-transcriptional expression of the Bmi-1 gene selectively targets only cells that contain the Bmi-1 transcript. The use of such compounds in the methods described herein should, therefore, have reduced side effects to non-specific targets and cells. Moreover, the UTR targeted approach of the methods described herein may further exploit the endogenous regulatory elements of Bmi-1 expression, thus, avoiding many technical, safety, and efficacy issues involved with other therapeutic approaches envisioned for the treatment cancer, e.g., genetic approaches to deliver DNA encoding therapeutic genes or to modify endogenous mutated genes. Thus, the methods of the present assay offer several advantages, in terms of increased specificity and efficacy and reduced side effects.

Without being bound by any particular theory, the compounds that modulate or disrupt the function of the Bmi-1 5'-UTR and 3'-UTR, or the Bmi-1 5'-UTR, or the Bmi-1 3'-UTR or post-transcriptional regulatory elements thereof, when used therapeutically may decrease Bmi-1 in cancer patients. Thus, certain embodiments of the methods described herein are directed to a method for decreasing or down-regulating the expression of Bmi-1 protein in a subject in need thereof, comprising administering an effective amount of a compound to the subject, which compound has demonstrated activity for decreasing in vitro or in cultured cells the post-transcriptional expression of a nucleic acid construct comprising a reporter gene operably linked to any of the 5'-UTR and 3'-UTR, or the 5'-UTR or the 3'-UTR of Bmi-1, wherein the 5'-UTR is upstream of the reporter gene and the 3'-UTR is downstream of the reporter gene.

Accordingly, embodiments of the methods described herein are directed to a method for down-regulating the expression of Bmi-1 protein in a subject in need thereof, comprising administering to the subject an effective amount of a compound that down-regulates the expression of Bmi-1 protein post-transcriptionally. Other embodiments of the methods described herein are further directed to a method for treating cancer in a subject in need thereof, comprising administering to the human subject an effective amount of a compound that down-regulates the expression of Bmi-1 protein post-transcriptionally, wherein said compound decreases or down-regulates in vitro or in cultured cells the post-transcriptional expression of a nucleic acid construct comprising a reporter gene operably linked to any of the 5'-UTR and 3'-UTR, or the 5'-UTR or the 3'-UTR of Bmi-1, wherein the 5' UTR is upstream of the reporter gene and the 3' UTR is downstream of the reporter gene.

In one embodiment, a method for down-regulating the expression of Bmi-1 protein in a subject in need thereof, comprises administering to the subject an effective amount of a compound that down-regulates in vitro or in cultured cells the post-transcriptional expression of a nucleic acid construct comprising a reporter gene operably linked to (i) the 5'-UTR of Bmi-1, or (ii) the 3'-UTR of Bmi-1, or (iii) the 5'-UTR and 3'-UTR of Bmi-1, and wherein the 5'-UTR is upstream of the reporter gene and the 3'-UTR is downstream of the reporter gene.

In one embodiment, a method for treating cancer in a subject in need thereof; comprises administering to the subject an effective amount of a compound that down-regulates in vitro or in cultured cells the post-transcriptional expression of a nucleic acid construct comprising a reporter gene operably linked to (i) the 5'-UTR of Bmi-1, or (ii) the 3'-UTR of Bmi-1, or (iii) the 5'-UTR and 3'-UTR of Bmi-1, wherein the 5'-UTR is upstream of the reporter gene and the 3'-UTR is downstream of the reporter gene. In another embodiment, the method further comprises administering to the subject one or more additional agents. In a specific embodiment, the additional agents are agents that down-regulate the expression of Bmi-1 protein transcriptionally.

An embodiment of one or more uses of the methods described herein is directed to a method for identifying or validating a compound that down-regulates post-transcriptional expression of Bmi-1.

Compounds described herein can be prepared by those skilled in the art using known methods, including a free acid, free base, salt, ester, hydrate, solvate, polymorph, clathrate, geometric isomer, stereoisomer, racemate, enantiomer or tautomer thereof, as set forth in copending U.S. Provisional Patent Application Ser. No. 61/077,367 filed Jul. 1, 2008, entitled "BMI-1 Protein Expression Modulators," which is incorporated herein by reference in its entirety and for all purposes, wherein the compound described herein may be selected from the group consisting of:

| Compound | Structure | Name |
|---|---|---|
| 1 | 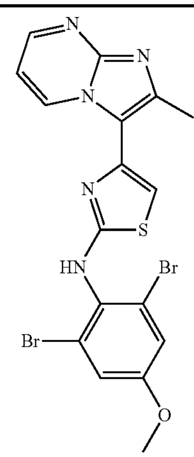 | N-(2,6-dibromo-4-methoxyphenyl)-4-(2-methylimidazo[1,2-a]pyrimidin-3-yl)thiazol-2-amine |
| 2 | 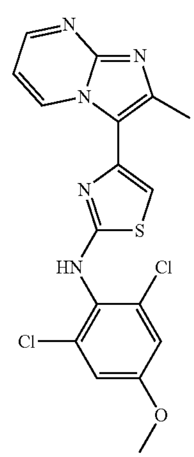 [SMILES: COc1cc(Cl)c(Nc2nc(-c3c(C)nc4ncccn34)cs2)c(Cl)c1] | N-(2,6-dichloro-4-methoxyphenyl)-4-(2-methylimidazo[1,2-a]pyrimidin-3-yl)thiazol-2-amine |

-continued

| Compound | Structure | Name |
|---|---|---|
| 3 | 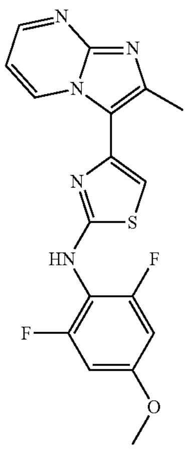 [SMILES: COc1cc(F)c(Nc2nc(-c3c(C)nc4ncccn34)cs2)c(F)c1] | N-(2,6-difluoro-4-methoxyphenyl)-4-(2-methylimidazo[1,2-a]pyrimidin-3-yl)thiazol-2-amine |
| 4 | 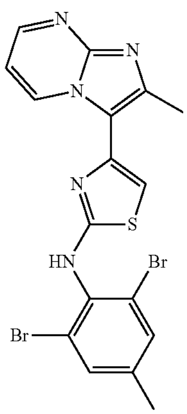 [SMILES: Cc1cc(Br)c(Nc2nc(-c3c(C)nc4ncccn34)cs2)c(Br)c1] | N-(2,6-dibromo-4-methylphenyl)-4-(2-methylimidazo[1,2-a]pyrimidin-3-yl)thiazol-2-amine |
| 5 | 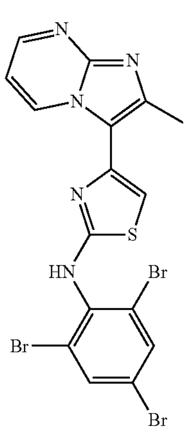 [SMILES: Cc1nc2ncccn2c1-c1csc(Nc2c(Br)cc(Br)cc2Br)n1] | 4-(2-methylimidazo[1,2-a]pyrimidin-3-yl)-N-(2,4,6-tribromophenyl)thiazol-2-amine |

-continued

| Compound | Structure | Name |
|---|---|---|
| 6 | 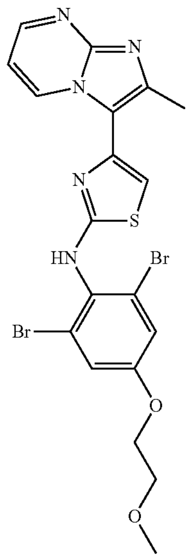 [SMILES: COCCOc1cc(Br)c(Nc2nc(-c3c(C)nc4ncccn34)cs2)c(Br)c1] | N-(2,6-dibromo-4-(2-methoxyethoxy)phenyl)-4-(2-methylimidazo[1,2-a]pyrimidin-3-yl)thiazol-2-amine |
| 7 | 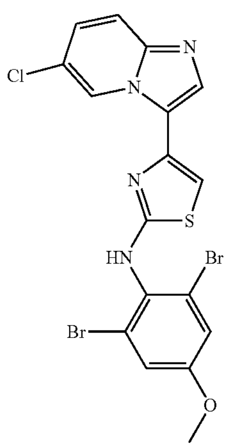 [SMILES: COc1cc(Br)c(Nc2nc(-c3cnc4ccc(Cl)cn34)cs2)c(Br)c1] | 4-(6-chloroimidazo[1,2-a]pyridine-3-yl)-N-(2,6-dibromo-4-methoxyphenyl)thiazol-2-amine |
| 8 | 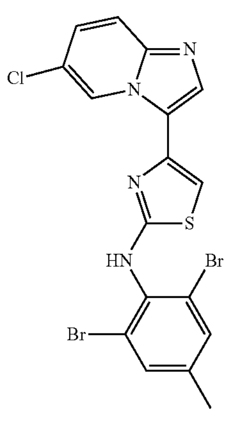 [SMILES: Cc1cc(Br)c(Nc2nc(-c3cnc4ccc(Cl)cn34)cs2)c(Br)c1] | 4-(6-chloroimidazo[1,2-a]pyridine-3-yl)-N-(2,6-dibromo-4-methylphenyl)thiazol-2-amine |

| Compound | Structure | Name |
|---|---|---|
| 9 | 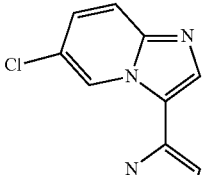 | 4-(6-chloroimidazo[1,2-a]pyridine-3-yl)-N-(2,6-dichloro-4-methoxyphenyl)thiazol-2-amine |

Compound names used herein were obtained using ACD Labs Index Name software Version 10.0, provided by ACD Labs; and/or, were provided using ChemDraw Ultra 10.0.4, provided by CambridgeSoft. When the compound name disclosed herein conflicts with the structure depicted, the structure shown will supercede the use of the name to define the compound intended.

In a specific embodiment, the methods described herein provide methods for down-regulating the expression of Bmi-1 protein in a human or non-human animal subject in need thereof, comprising administering to the subject an effective amount of a compound, wherein the compound is: N-(2,6-dibromo-4-methoxyphenyl)-4-(2-methylimidazo[1,2-a]pyrimidin-3-yl)thiazol-2-amine; N-(2,6-dichloro-4-methoxyphenyl)-4-(2-methylimidazo[1,2-a]pyrimidin-3-yl)thiazol-2-amine; N-(2,6-difluoro-4-methoxyphenyl)-4-(2-methylimidazo[1,2-a]pyrimidin-3-yl)thiazol-2-amine; N-(2,6-dibromo-4-methylphenyl)-4-(2-methylimidazo[1,2-a]pyrimidin-3-yl)thiazol-2-amine; 4-(2-methylimidazo[1,2-a]pyrimidin-3-yl)-N-(2,4,6-tribromophenyl)thiazol-2-amine; N-(2,6-dibromo-4-(2-methoxyethoxy)phenyl)-4-(2-methylimidazo[1,2-a]pyrimidin-3-yl)thiazol-2-amine; 4-(6-chloroimidazo[1,2-a]pyridine-3-yl)-N-(2,6-dibromo-4-methoxyphenyl)thiazol-2-amine; 4-(6-chloroimidazo[1,2-a]pyridine-3-yl)-N-(2,6-dibromo-4-methylphenyl)thiazol-2-amine; or 4-(6-chloroimidazo[1,2-a]pyridine-3-yl)-N-(2,6-dichloro-4-methoxyphenyl)thiazol-2-amine, or a free acid, free base, salt, ester, hydrate, solvate, polymorph, clathrate, geometric isomer, stereoisomer, racemate, enantiomer or tautomer thereof. In certain embodiments, the form of the compound is pharmaceutically acceptable.

In another embodiment, the methods described herein provide methods for treating cancer in a human or non-human animal subject in need thereof, comprising administering to the subject an effective amount of a compound that down-regulates in vitro or in cultured cells the post-transcriptional expression of a nucleic acid construct comprising a reporter gene operably linked to (i) the 5'-UTR of Bmi-1, or (ii) the 3'-UTR of Bmi-1, or (iii) the 5'-UTR and 3'-UTR of Bmi-1, and wherein the 5'-UTR is upstream of the reporter gene and the 3'-UTR is downstream of the reporter gene. In a specific embodiment, the compound is: N-(2,6-dibromo-4-methoxyphenyl)-4-(2-methylimidazo[1,2-a]pyrimidin-3-yl)thiazol-2-amine; N-(2,6-dichloro-4-methoxyphenyl)-4-(2-methylimidazo[1,2-a]pyrimidin-3-yl)thiazol-2-amine; N-(2,6-difluoro-4-methoxyphenyl)-4-(2-methylimidazo[1,2-a]pyrimidin-3-yl)thiazol-2-amine; N-(2,6-dibromo-4-methylphenyl)-4-(2-methylimidazo[1,2-a]pyrimidin-3-yl)thiazol-2-amine; 4-(2-methylimidazo[1,2-a]pyrimidin-3-yl)-N-(2,4,6-tribromophenyl)thiazol-2-amine; N-(2,6-dibromo-4-(2-methoxyethoxy)phenyl)-4-(2-methylimidazo[1,2-a]pyrimidin-3-yl)thiazol-2-amine; 4-(6-chloroimidazo[1,2-a]pyridine-3-yl)-N-(2,6-dibromo-4-methoxyphenyl)thiazol-2-amine; 4-(6-chloroimidazo[1,2-a]pyridine-3-yl)-N-(2,6-dibromo-4-methylphenyl)thiazol-2-amine; or 4-(6-chloroimidazo[1,2-a]pyridine-3-yl)-N-(2,6-dichloro-4-methoxyphenyl)thiazol-2-amine, or a free acid, free base, salt, ester, hydrate, solvate, polymorph, clathrate, geometric isomer, stereoisomer, racemate, enantiomer or tautomer thereof. In certain embodiments, the form of the compound is pharmaceutically acceptable.

In yet another embodiment, the methods described herein provide methods for treating cancer in a human or non-human animal subject in need thereof, comprises administering to the subject an effective amount of a pharmaceutical composition comprising: N-(2,6-dibromo-4-methoxyphenyl)-4-(2-methylimidazo[1,2-a]pyrimidin-3-yl)thiazol-2-amine; N-(2,6-dichloro-4-methoxyphenyl)-4-(2-methylimidazo[1,2-a]pyrimidin-3-yl)thiazol-2-amine; N-(2,6-difluoro-4-methoxyphenyl)-4-(2-methylimidazo[1,2-a]pyrimidin-3-yl)thiazol-2-amine; N-(2,6-dibromo-4-methylphenyl)-4-(2-methylimidazo[1,2-a]pyrimidin-3-yl)thiazol-2-amine; 4-(2-methylimidazo[1,2-a]pyrimidin-3-yl)-N-(2,4,6-tribromophenyl)thiazol-2-amine; N-(2,6-dibromo-4-(2-methoxyethoxy)phenyl)-4-(2-methylimidazo[1,2-a]pyrimidin-3-yl)thiazol-2-amine; 4-(6-chloroimidazo[1,2-a]pyridine-3-yl)-N-(2,6-dibromo-4-methoxyphenyl)thiazol-2-amine; 4-(6-chloroimidazo[1,2-a]pyridine-3-yl)-N-(2,6-dibromo-4-methylphenyl)thiazol-2-amine; or 4-(6-chloroimidazo[1,2-a]pyridine-3-yl)-N-(2,6-dichloro-4-methoxyphenyl)thiazol-2-amine, or a free acid, free base, salt, ester, hydrate, solvate, polymorph, clathrate, geometric isomer, stereoisomer, racemate, enantiomer or tautomer thereof. In certain embodiments, the form of the compound is pharmaceutically acceptable.

Terminology

As used herein, the italicized term "Bmi-1," unless otherwise specified or clear from the context of the specification, refers to a Bmi-1 nucleic acid sequence. The nucleic acid sequence may be DNA, RNA or messenger RNA (mRNA).

As used herein, the non-italicized term "Bmi-1," unless otherwise specified or clear from the context of the specification, refers to a protein expressed from a Bmi-1 nucleic acid sequence.

As used herein, the term "CAP," "cap" or "5' cap" refers to a methylated guanine cap, e.g., a 7 methylguanosine (5'-5') RNA triphosphate that is added to the 5' end of a pre-mRNA.

As used herein, the term "about" or "approximately" when used in conjunction with a number refers to any number within 0.25%, 0.5%, 1%, 5% or 10% of the referenced number.

As used herein, the term "AU rich" element refers to a region in the Bmi-1 3'-UTR mRNA rich in adenosine and uridine.

As used herein, the term "compound," unless otherwise specified or clear from the context in the specification, refers to any agent that is being tested for its ability to modulate post-transcriptional expression of Bmi-1 or has been identified or validated as modulating the post-transcriptional expression of the Bmi-1 gene. In a specific embodiment a compound is any agent that is tested for its ability to modulate untranslated region-dependent expression of Bmi-1, or has been identified or validated as modulating the expression of Bmi-1. In one embodiment, a compound is a purified cancer molecule including, but not limited to, peptides, peptidomimetics, amino acids, amino acid analogs, polynucleotides, polynucleotide analogs, nucleotides, nucleotide analogs, other organic and inorganic compounds (i.e., including heteroorganic and organometallic compounds) having a molecular weight less than about 10,000 grams per mole, or a molecular weight less than about 5,000 grams per mole, or a molecular weight less than about 1,000 grams per mole, or a molecular weight less than about 500 grams per mole, or a molecular weight less than about 100 grams per mole, and salts, esters, and other pharmaceutically acceptable forms thereof.

As used herein, the term "effective amount" in the context of administering a compound to a subject refers to the amount of a compound which is sufficient to achieve at least one or more of the following effects: (i) the reduction or amelioration of the severity of cancer and/or a symptom associated therewith; (ii) the reduction in the duration of a symptom associated with cancer; (iii) the prevention in the recurrence of a symptom associated with cancer; (iv) the regression of cancer and/or a symptom associated therewith; (v) the reduction in hospitalization of a subject; (vi) the reduction in hospitalization length; (vii) the increase in the survival of a subject; (viii) the inhibition of the progression of cancer and/or a symptom associated therewith; (ix) the enhancement or improvement the therapeutic effect of another therapy; (x) a reduction or elimination in the cancer cell population; (xi) a reduction in the growth of a tumor or neoplasm; (xii) a decrease in tumor size; (xiii) a reduction in the formation of a tumor; (xiv) eradication, removal, or control of primary, regional and/or metastatic cancer; (xv) a decrease in the number or size of metastases; (xvi) a reduction in mortality; (xvii) an increase in cancer-free survival rate of patients; (xviii) an increase in relapse free survival; (xix) an increase in the number of patients in remission; (xx) a decrease in hospitalization rate; (xxi) the size of the tumor is maintained and does not increase or increases by less of the tumor after administration of a standard therapy as measured by conventional methods available to one of skill in the art, such as MRI, X-ray, and CAT Scan; (xxii) the prevention of the development or onset of cancer or a symptom associated therewith; (xxiii) an increase in the length of remission in patients; (xxiv) the reduction in the number of symptoms associated with cancer; and/or (xxv) an increase in symptom-free survival of cancer patients.

As used herein, the term "elderly human" refers to a human 65 years or older.

As used herein, the term "form" in the context of a compound refers to a compound isolated for use as a free acid, free base, salt, ester, hydrate, solvate, polymorph, clathrate, geometric isomer, stereoisomer, racemate, enantiomer or tautomer thereof. In certain embodiments, such a form may be pharmaceutically acceptable.

As used herein, the term "fragment" in the context of nucleotide sequences refers to a nucleotide sequence comprising a nucleic acid sequence of at least 5 contiguous nucleic acid residues, at least 10 contiguous nucleic acid residues, at least 15 contiguous nucleic acid residues, at least 20 contiguous nucleic acid residues, at least 25 contiguous nucleic acid residues, at least 40 contiguous nucleic acid residues, at least 50 contiguous nucleic acid residues, at least 60 contiguous nucleic acid residues, at least 70 contiguous nucleic acid residues, at least 80 contiguous nucleic acid residues, at least 90 contiguous nucleic acid residues, at least 100 contiguous nucleic acid residues, at least 125 contiguous nucleic acid residues, at least 150 contiguous nucleic acid residues, at least 175 contiguous nucleic acid residues, at least 200 contiguous nucleic acid residues, or at least 250 contiguous nucleic acid residues of the nucleotide sequence of the gene of interest, e.g., Bmi-1. The nucleic acid may be RNA, DNA, or a chemically modified variant thereof. In a specific embodiment, the fragment is a fragment of a UTR of Bmi-1. In a specific embodiment, a fragment of the UTR region of the Bmi-1 mRNA transcripts retains at least one element of the UTR (e.g., an IRES). In a specific embodiment, a fragment of the 5' untranslated region of human Bmi-1 is composed of less than the 505 nucleic acid residues of the 5'-UTR of human Bmi-1 (SEQ ID NO: 1). In another embodiment, a fragment of the 5' untranslated region of murine Bmi-1 is composed of less than 471 nucleic acid residues of the 5'-UTR of murine Bmi-1 (SEQ ID NO: 7).

As used herein, the term "fragment" in the context of amino acid sequences refers to an amino acid sequence comprising an amino acid sequence of at least 5 amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino acid residues, at least 70 amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, or at least contiguous 250 amino acid residues of the amino acid sequence of the Bmi-1 protein.

As used herein, the term "GC-rich region" refers to a region of the Bmi-1 5'-UTR mRNA rich in guanine and cytosine.

As used herein, the term "heterologous nucleotide sequence" refers to a nucleotide sequence that either does not occur in the native or wild-type gene or which is present, but has been moved out of its native or wild-type position.

As used herein, the term "heterologous amino acid sequence" refers to an amino acid sequence that either does not occur in the native or wild-type protein or which is present, but has been moved out of its native or wild-type position.

As used herein, the term "host cell" includes a particular subject cell transformed or transfected with a nucleic acid construct as described herein and the progeny or potential progeny of such a cell. Progeny of such a cell may not be identical to the parent cell transfected with the nucleic acid construct due to mutations or environmental influences that may occur in succeeding generations or integration of the nucleic acid construct into the host cell genome. In one embodiment, a host cell includes a particular subject cell stably transformed or transfected with the nucleic acid construct described herein and the progeny or potential progeny of such a cell.

As used herein, the term "hydrate" refers to a compound which further includes a stoichiometric or non-stoichiometric amount of water bound by non-covalent intermolecular forces.

As used herein, the term "human adult" refers to a human that is 18 years or older.

As used herein, the term "human child" refers to a human that is 1 year to 18 years old.

As used herein, the term "human infant" refers to a newborn to 1 year old year human.

As used herein, the term "human toddler" refers to a human that is 1 year to 3 years old.

As used herein, the term "in combination," refers, in the context of the administration of a compound described herein, to the administration of one or more compounds described herein that down-regulate the expression of Bmi-1 protein post-transcriptionally alone or in combination with one or more additional agents for use in treating cancer. The use of the term "in combination" does not restrict the order in which one or more compounds described herein or another agent are administered to a human subject having cancer.

As used herein, the term "IRES" refers to an internal ribosome entry site in the 5'-UTR of a mRNA.

An "isolated" nucleic acid sequence, nucleotide sequence, or polynucleotide sequence is one which is separated from other nucleic acid molecules which are present in a natural source of the nucleic acid sequence or nucleotide sequence. Moreover, an "isolated" nucleic acid sequence, or nucleotide sequence, or polynucleotide sequence, such as a cDNA or RNA molecules, can be substantially free of other cellular material or culture medium when produced by recombinant techniques, or substantially free of chemical precursors when chemically synthesized. In a specific embodiment, an "isolated" nucleic acid sequence, or nucleotide sequence, or polynucleotide sequence is substantially free when the "isolated" nucleic acid sequence, or nucleotide sequence, or polynucleotide sequence is 60%, 65%, 75%, 80%, 85%, 90%, 95%, or 99% free of other cellular material. In certain embodiments, an "isolated" nucleic acid sequence, nucleotide sequence, or polynucleotide sequence is a nucleic acid sequence, nucleotide sequence, or polynucleotide sequence that is recombinantly expressed in a heterologous cell. In a specific embodiment, a nucleic acid construct described herein is isolated.

As used herein, the term "not significantly altered" means that the compound alters the expression of the reporter gene or Bmi-1 by less than 40%, less than 35%, less than 30%, less than 25%, less than 20%, less than 15%, less than 10%, less than 5%, or less than 2% relative to a negative control such as PBS or DMSO. In some embodiments, the term "not significantly altered" means that the compound alters the expression of the reporter gene or Bmi-1 by less than 1 fold, less than 0.5 fold, less than 0.2 fold, or less than 0.1 fold relative to a negative control such as PBS or DMSO.

As used herein, the term "significantly altered" means that the compound alters the expression of the reporter gene or Bmi-1 by more than 40%, more than 45%, more than 50%, more than 55%, more than 60%, more than 65%, more than 70%, more than 75%, or more than 80% relative to a negative control such as PBS or DMSO. In some embodiments, the term "significantly altered" means that the compound alters the expression of the reporter gene or Bmi-1 by more than 1 fold, more than 1.5 fold, more than 2 fold, or more than 2.5 fold relative to a negative control such as PBS or DMSO.

As used herein, the terms "significantly decreased" or "significantly down-regulated" mean that the compound decreases or down-regulates the expression of the reporter gene or Bmi-1 by more than 40%, more than 45%, more than 50%, more than 55%, more than 60%, more than 65%, more than 70%, more than 75%, or more than 80% relative to a negative control such as PBS or DMSO. In some embodiments, the terms "significantly decreased" or "significantly down-regulated" mean that the compound decreases or down-regulates the expression of the reporter gene or Bmi-1 by more than 1 fold, more than 1.5 fold, more than 2 fold, or more than 2.5 fold relative to a negative control such as PBS or DMSO.

In some embodiments, the terms "nucleic acid," "nucleotide" and "polynucleotide" refer to deoxyribonucleotides, deoxyribonucleic acids, ribonucleotides, and ribonucleic acids, and polymeric forms thereof, and include either single- or double-stranded forms. In certain embodiments, such terms include known analogues of natural nucleotides, for example, peptide nucleic acids ("PNA"s), that have similar binding properties as the reference nucleic acid. In some embodiments, such terms refer to deoxyribonucleic acids (e.g., cDNA or DNA). In other embodiments, such terms refer to ribonucleic acids (e.g., mRNA or RNA).

As used herein, the term "ORF" refers to the open reading frame of a mRNA, i.e., the region of the mRNA that is translated into protein.

As used herein, the term "pharmaceutically acceptable" refers to a component that is, within the scope of sound medical judgment, suitable for use in contact with the tissues of humans and other mammals without undue toxicity, irritation, allergic response and the like, and are commensurate with a reasonable benefit/risk ratio.

As used herein, the term "pharmaceutically acceptable salt" refers to any non-toxic salt that, upon administration to a recipient, is capable of providing, either directly or indirectly, a compound as described herein. Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, hydrochloride, bromide, hydrobromide, iodide, hydroiodide, acetate, trifluoroacetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In a specific embodiment, pharmaceutically acceptable acid addition salts include those formed with mineral acids such as hydrochloric acid and hydrobromic acid, and especially those formed with organic acids such as maleic acid or trifluoroacetic acid.

As used herein, the term "previously determined reference range" refers to a reference range for the expression of a reporter gene expressed either by an instant nucleic acid construct or the Bmi-1 gene from a particular cell or in a particular cell-free extract. Ideally, each laboratory will establish its own reference range for each assay, each cell type and each cell-free extract. In one embodiment, at least one positive control or at least one negative control are included for use in the assay. In a specific embodiment, the previously determined reference range is the amount or activity of the reporter protein detected in the presence of a negative control (e.g., PBS or DMSO).

As used herein, the term "purified," in the context of a compound, refers to a compound that is substantially free of chemical precursors, intermediate compounds or other chemicals (such as reagents, solvents and the like) after being separated from the synthetic reaction mixture. In a specific embodiment, the compound is 60%, preferably 65%, 70%, 75%, 80%, 85%, 90%, or 99% free of such other, different chemicals or compounds. In a specific embodiment, a compound described herein is purified.

As used herein, the terms "reporter gene expression," "expression of a reporter gene," "expression of the reporter gene," "expression of a nucleic acid construct comprising a reporter gene" and the like are used coextensively and refer to the amount or activity of the reporter protein detected in the methods described herein.

As used herein and unless otherwise indicated, the term "solvate" means a compound, or a salt thereof, that further includes a stoichiometric or non-stoichiometric amount of a solvent (e.g., water) bound by non-covalent intermolecular forces.

As used herein, the terms "subject" and "patient" are used interchangeably and refer to an animal, preferably a mammal including a non-primate (e.g., a camel, donkey, zebra, cow, pig, horse, goat, sheep, cat, dog, rat, and mouse) and a primate (e.g., a monkey, chimpanzee, and a human), and most preferably a human.

As used herein, the term "synergistic," refers to the effect of the administration of a combination product as described herein which is more effective than the additive effects of any two or more single agents. In a specific embodiment, a synergistic effect of a combination product permits the use of lower dosages of one or more agents and/or less frequent administration of said agents to a subject with cancer. In certain embodiments, the ability to utilize lower dosages of an agent and/or to administer said agents less frequently reduces the toxicity associated with the administration of said agents to a subject without reducing the efficacy of said agents in the prevention or treatment of cancer. In some embodiments, a synergistic effect results in improved efficacy of each of the agents in treating cancer. In some embodiments, a synergistic effect of a combination of agents avoids or reduces adverse or unwanted side effects associated with the use of any single agent. The combination of agents in such a product can be administered to a subject in the same pharmaceutical composition. Alternatively, the agents can be administered concurrently to a subject in separate pharmaceutical compositions.

The agents may also be administered to a subject by the same or different routes of administration. In a specific embodiment, at least one of the agents is a compound.

As used herein, the term "target RNA," unless otherwise defined herein, refers to the mRNA transcribed from the Bmi-1 gene.

As used herein, the term "treat" refers to treatment from which a subject receives a beneficial effect such as the reduction, decrease, attenuation, diminishment, stabilization, remission, suppression, inhibition or arrest of the development or progression of cancer, or a symptom thereof. In certain embodiments, the treatment that a subject receives results in at least one or more of the following effects: (i) the reduction or amelioration of the severity of cancer and/or a symptom associated therewith; (ii) the reduction in the duration of a symptom associated with cancer; (iii) the prevention in the recurrence of a symptom associated with cancer; (iv) the regression of cancer and/or a symptom associated therewith; (v) the reduction in hospitalization of a subject; (vi) reduction in hospitalization length; (vii) the increase in the survival of a subject; (viii) the inhibition of the progression of cancer and/or a symptom associated therewith; (ix) the enhancement or improvement the therapeutic effect of another therapy; (x) a reduction or elimination in the cancer cell population; (xi) a reduction in the growth of a tumor or neoplasm; (xii) a decrease in tumor size; (xiii) a reduction in the formation of a tumor; (xiv) eradication, removal, or control of primary, regional and/or metastatic cancer; (xv) a decrease in the number or size of metastases; (xvi) a reduction in mortality; (xvii) an increase in cancer-free survival rate of patients; (xviii) an increase in relapse free survival; (xix) an increase in the number of patients in remission; (xx) a decrease in hospitalization rate; (xxi) the size of the tumor is maintained and does not increase or increases by less of the tumor after administration of a standard therapy as measured by conventional methods available to one of skill in the art, such as MRI, X-ray, and CAT Scan; (xxii) the prevention of the development or onset of cancer or a symptom associated therewith; (xxiii) an increase in the length of remission in patients; (xxiv) the reduction in the number of symptoms associated with cancer; and/or (xxv) an increase in symptom-free survival of cancer patients. In some embodiments, the treatment that a subject receives does not cure cancer, but prevents the progression or worsening of the disease.

As used herein, the term "UTR" refers to an "untranslated region" of a nucleotide sequence of a mRNA or DNA sequence or chemical analog thereof that is transcribed into a mRNA in which the nucleotides corresponding to the open reading frame ("ORF") are not present. In some embodiments, the UTR is the region of a mRNA that is not translated into protein. In one embodiment, the UTR is either or both a 5'-UTR, i.e., upstream of the ORF coding region, or a 3'-UTR, i.e., downstream of the ORF coding region.

As used herein, the term, "untranslated region-independent" or "UTR-independent" refers to the regulation of gene expression independent of the untranslated regions at the level of post-transcriptional mechanisms.

As used herein, the term "uORF" refers to an upstream open reading frame that is in the 5'-UTR of the main open reading frame, i.e., that encodes a functional protein, of a mRNA.

As used herein, the term "untranslated region-dependent expression" or "UTR-dependent expression" refers to the regulation of gene expression through the untranslated region's regulatory elements at the level of mRNA function, utilization or protein translation, i.e., during or after transcription of the gene from the DNA has begun. In one embodiment, the term "untranslated region-dependent expression" or "UTR-dependent expression" refers to the regulation of mRNA translation.

DESCRIPTION OF THE DRAWINGS

FIG. 1: Human Bmi-1 5'-UTR: Nucleotide sequence corresponding to the 5'-UTR of human Bmi-1 (SEQ ID NO: 1) and the start codon (AUG). The 5'-UTR of human Bmi-1 is 505 nucleotides in length, is 66.3% GC rich, contains 3 uORFs (indicated by underline), and an in-frame alternative translation initiation site (indicated as bolded nucleotides).

FIG. 2: Human Bmi-1 3'-UTR: Nucleotide sequence corresponding to the stop codon (UGA) and 3'-UTR of human Bmi-1 (SEQ ID NO: 2). The 3'-UTR of human Bmi-1 is 1771 nucleotides in length, comprises 8 AU-rich elements (AREs; indicated by underline), and 2 polyA signals (indicated as bolded nucleotides).

FIG. 4: Alignment of Murine and Human Bmi-1 5'-UTRs: Alignment of murine Bmi-1 5'-UTR (mbmi-1; SEQ ID NO: 7) and human Bmi-1 5'-UTR (hbmi-1; SEQ ID NO: 1) shows 88.8% pairwise identity.

FIG. 5A-5C: Alignment of Murine and Human Bmi-1 3'-UTRs: Alignment of murine Bmi-1 3'-UTR (mbmi-1; SEQ ID NO: 8) and human Bmi-1 3'-UTR (hbmi-1; SEQ ID NO: 2) shows 82% pairwise identity.

DETAILED DESCRIPTION

Figure 3:
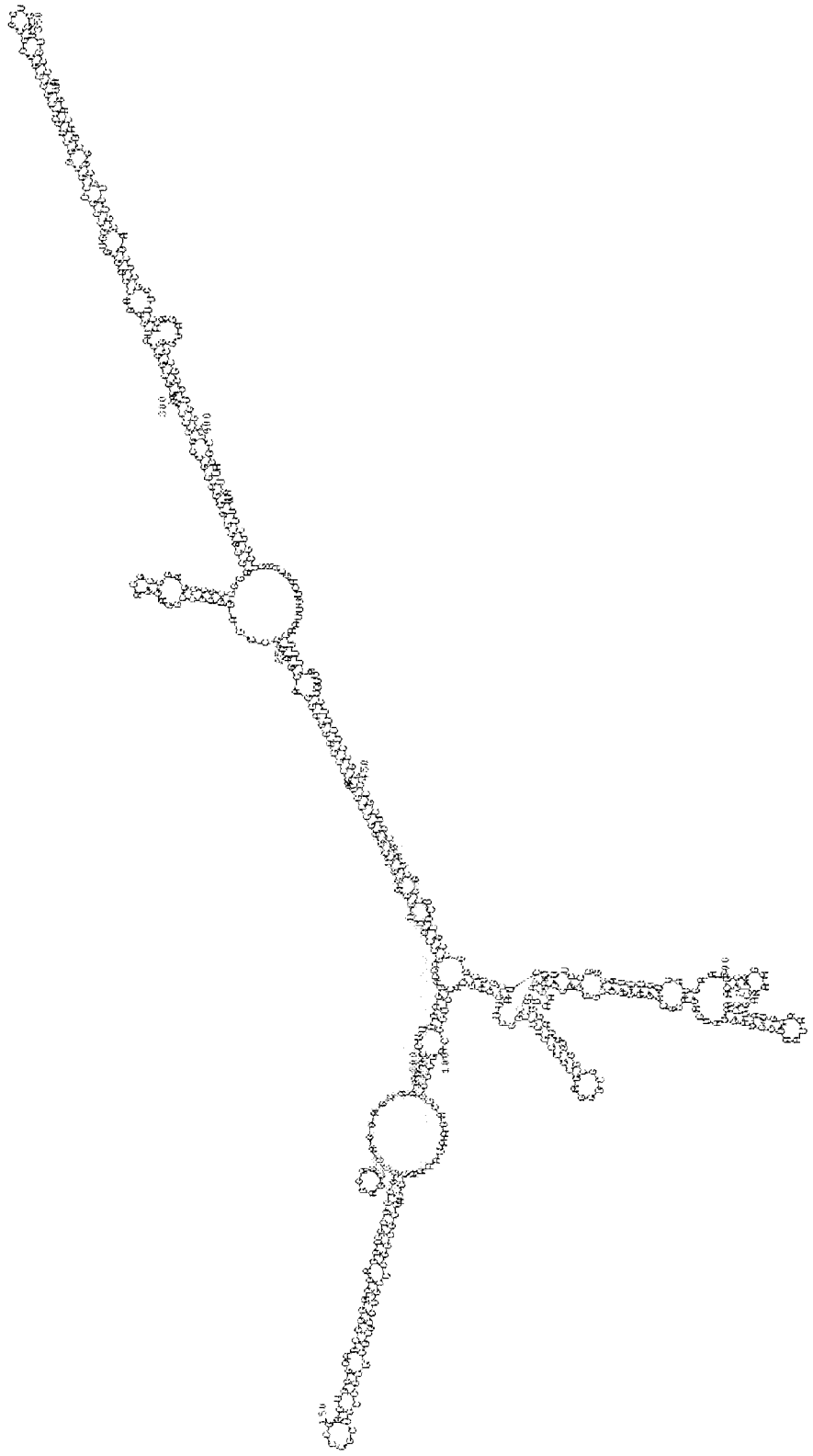
FIG. 3: Bmi-1 5'-UTR Secondary Structure: Schematic representation of the secondary structure of the entire human Bmi-1 5'-UTR predicted by mFold software.

The compounds described herein are useful in the treatment of cancer. In particular, the method for the treatment of cancer in a human subject in need thereof, comprises administering an effective amount of a compound to the human subject, in which said compound decreases or down-regulates the post-transcriptional expression in vitro or in cultured cells of a nucleic acid construct comprising a reporter gene operably linked to any of the 5'-UTR and 3'-UTR, or the 5'-UTR or the 3'-UTR of Bmi-1, wherein the 5'-UTR is upstream of the reporter gene and the 3'-UTR is downstream of the reporter gene.

Without being bound by any particular theory, the compounds target any of the 5'-UTR and 3'-UTR of Bmi-1, or the 5'-UTR or the 3'-UTR of Bmi-1 and decrease or down-regulate the expression of Bmi-1 in cancer patients, which provides a therapeutic benefit. In a specific embodiment, the compounds bind directly to any of the 5'-UTR and 3'-UTR, or the 5'-UTR or the 3'-UTR of Bmi-1 RNA and decrease or down-regulate expression of Bmi-1 protein in cancer patients, which provides a therapeutic benefit. In another embodiment, the compounds bind to proteins and/or molecules that bind and/or associate with any of the 5'-UTR and 3'-UTR, or the 5'-UTR or the 3'-UTR of Bmi-1. In another embodiment, the compounds bind to nucleotide regulatory sequences of genes that encode proteins that bind and/or associate with any of the 5'-UTR and 3'-UTR, or the 5'-UTR or the 3'-UTR of Bmi-1.

The screening methods described herein provide for the identification or validation of compounds that target any of the 5'-UTR and 3'-UTR, or the 5'-UTR or the 3'-UTR of Bmi-1 mRNA transcripts. These screening methods involve the use of a nucleic acid construct comprising a reporter gene operably linked to any of the 5'-UTR and 3'-UTR, or the 5'-UTR or the 3'-UTR of Bmi-1, wherein the 5'-UTR is upstream of the reporter gene and the 3'-UTR is downstream of the reporter gene. Compounds that specifically decrease or down-regulate the post transcriptional activity of any of the 5'-UTR and 3'-UTR, or the 5'-UTR or the 3'-UTR of Bmi-1 and decrease or down-regulate expression of the reporter gene are expected to provide a therapeutic benefit.

Compounds selected for use in the screening methods described herein include those compounds that bind directly to any of the 5'-UTR and 3'-UTR, or the 5'-UTR or the 3'-UTR of Bmi-1. Compounds described herein also include those that bind to proteins and/or molecules that bind and/or associate with any of the 5'-UTR and 3'-UTR, or the 5'-UTR or the 3'-UTR of Bmi-1. Compounds described herein also include those that bind to nucleotide regulatory sequences of genes that encode proteins that bind and/or associate with any of the 5'-UTR and 3'-UTR, or the 5'-UTR or the 3'-UTR of Bmi-1.

The subsections below describe in more detail the type of compounds that decrease or down-regulate the post-transcriptional expression of a nucleic acid construct comprising a reporter gene operably linked to any of the 5'-UTR and 3'-UTR, or the 5'-UTR or the 3'-UTR of Bmi-1, screening methods for identifying or validating compounds that decrease or down-regulate the expression of Bmi-1 protein post-transcriptionally, methods for characterizing compounds, and methods of using the compounds to treat cancer.

Compounds

Compounds identified and validated using the in vitro and cultured host cell screening methods described herein have demonstrated activity for decreasing the post-transcriptional expression of a nucleic acid construct comprising a reporter gene operably linked to any of the 5'-UTR and 3'-UTR, or the 5'-UTR or the 3'-UTR of Bmi-1 and, thus post-transcriptionally decrease or down-regulate expression of Bmi-1 protein. In an embodiment, the compounds are specific for any of the 5'-UTR and 3'-UTR, or the 5'-UTR or the 3'-UTR of Bmi-1 target mRNA transcripts and thus may post-transcriptionally decrease or down-regulate expression of Bmi-1 protein by destabilizing the mRNA transcripts of Bmi-1 protein. In another embodiment, the compounds are specific for any of the 5'-UTR and 3'-UTR, or the 5'-UTR or the 3'-UTR of Bmi-1 target mRNA transcripts and thus may post-transcriptionally decrease or down-regulate expression of Bmi-1 protein by disrupting an interaction with or between any one of the 5'-UTR and 3'-UTR, or the 5'-UTR or the 3'-UTR of the Bmi-1 target mRNA transcripts.

Accordingly, the methods described herein are directed to a compound or a free acid, free base, salt, ester, hydrate, solvate, polymorph, clathrate, geometric isomer, stereoisomer, racemate, enantiomer or tautomer thereof for use in modulating UTR-dependent expression of Bmi-1, wherein the compound is selected from the group consisting of: N-(2,6-dibromo-4-methoxyphenyl)-4-(2-methylimidazo[1,2-a]pyrimidin-3-yl)thiazol-2-amine; N-(2,6-dichloro-4-methoxyphenyl)-4-(2-methylimidazo[1,2-a]pyrimidin-3-yl)thiazol-2-amine; N-(2,6-difluoro-4-methoxyphenyl)-4-(2-methylimidazo[1,2-a]pyrimidin-3-yl)thiazol-2-amine; N-(2,6-dibromo-4-methylphenyl)-4-(2-methylimidazo[1,2-a]pyrimidin-3-yl)thiazol-2-amine; 4-(2-methylimidazo[1,2-a]pyrimidin-3-yl)-N-(2,4,6-tribromophenyl)thiazol-2-amine; N-(2,6-dibromo-4-(2-methoxyethoxy)phenyl)-4-(2-methylimidazo[1,2-a]pyrimidin-3-yl)thiazol-2-amine; 4-(6-chloroimidazo[1,2-a]pyridine-3-yl)-N-(2,6-dibromo-4-methoxyphenyl)thiazol-2-amine; and 4-(6-chloroimidazo[1,2-a]pyridine-3-yl)-N-(2,6-dichloro-4-methoxyphenyl)thiazol-2-amine.

Regulatory Regions of Bmi-1

Presented herein are isolated nucleic acid sequences comprising the 5'-UTR of Bmi-1 or a fragment thereof. A specific embodiment includes a nucleic acid sequence (in certain embodiments, an isolated nucleic acid sequence) comprising the 5'-UTR of Bmi-1 or a fragment thereof, wherein the 5'-UTR or fragment thereof is not operably linked to the coding sequence of Bmi-1. Another embodiment includes a nucleic acid sequence (in certain embodiments, an isolated nucleic acid sequence) comprising the 5'-UTR of Bmi-1 or a fragment thereof operably linked to a heterologous nucleotide sequence. Some embodiments herein include a nucleic acid sequence (in certain embodiments, an isolated nucleic acid sequence) comprising the 5'-UTR of Bmi-1 or a fragment thereof and an amino terminal fragment of the ORF of Bmi-1 (e.g., the first 3, 6, 9, 12, 18, 21, 24, or more nucleotides from the 5' end of the Bmi-1 ORF) operably linked to a heterologous nucleotide sequence, wherein the amino-terminal fragment of the Bmi-1 ORF and the heterologous nucleotide sequence are in frame. In a specific embodiment, the fragment of the 5'-UTR of Bmi-1 retains at least one element of the 5'-UTR, such as e.g., the GC rich region or IRES. In one embodiment, the 5'-UTR or fragment thereof is the human 5'-UTR of Bmi-1 or a fragment thereof. In another embodiment, the 5'-UTR or fragment thereof is the murine Bmi-1 or a fragment thereof. The sequences of human and murine Bmi-1 can be found e.g., in GenBank at Accession Nos. NM_005180 and NM_007552, respectively.

A specific embodiment presented herein is a nucleic acid (in certain embodiments, an isolated nucleic acid sequence) comprising nucleotides 1 to 505 of the 5'-UTR of human Bmi-1 (SEQ ID NO: 1), wherein the nucleotide sequence is not operably linked to the coding sequence of human Bmi-1. In another embodiment, presented herein is a nucleic acid sequence (in certain embodiments, an isolated nucleic acid sequence) comprising nucleotides 1 to 505 of the 5'-UTR of human Bmi-1 (SEQ ID NO: 1) operably linked to a heterologous sequence. In some embodiments, presented herein is a nucleic acid sequence (in certain embodiments, an isolated nucleic acid sequence) comprising the 5'-UTR from the 5' end of human Bmi-1 or a fragment thereof and an amino terminal fragment of the ORF of Bmi-1 (e.g., the first 3, 6, 9, 12, 18, 21, 24, or more nucleotides of the human Bmi-1 ORF) operably linked to a heterologous nucleotide sequence, wherein the amino-terminal fragment of the human Bmi-1 ORF and the heterologous nucleotide sequence are in frame.

In a specific embodiment presented herein is a nucleic acid (in certain embodiments, an isolated nucleic acid sequence) comprising nucleotides 1 to 471 of the 5'-UTR of murine Bmi-1 (SEQ ID NO: 1), wherein the nucleotide sequence is not operably linked to the coding sequence of murine Bmi-1. In another embodiment, presented herein is a nucleic acid sequence (in certain embodiments, an isolated nucleic acid sequence) comprising nucleotides 1 to 471 of the 5'-UTR of murine Bmi-1 (SEQ ID NO: 7) operably linked to a heterologous nucleotide sequence.

In another embodiment, presented herein are isolated nucleic acid sequences comprising the 3'-UTR of Bmi-1 or a fragment thereof. In a specific embodiment, presented herein is a nucleic acid sequence (in some embodiments, an isolated nucleic acid sequence) comprising the 3'-UTR of Bmi-1 or a fragment thereof, wherein the 3'-UTR of Bmi-1 or a fragment thereof is not operably linked to the coding sequence of Bmi-1. In another embodiment presented herein is a nucleic acid sequence (in some, embodiment, an isolated nuclei acid sequence) comprising the 3' UTR of Bmi-1 or a fragment thereof operably linked to a heterologous nucleotide sequence. In some embodiments, presented herein is a nucleic acid sequence (in certain embodiments, an isolated nucleic acid sequence) comprising a carboxy terminal fragment of the Bmi-1 ORF (e.g., the last 3, 6, 9, 12, 15, 18, 21, 24, or more nucleotides from the 3' end of the ORF of Bmi-1) and the 3'-UTR of Bmi-1 or a fragment, mutant or post-transcriptional regulatory element thereof operably linked to a heterologous nucleotide sequence, wherein the carboxy terminal fragment of the Bmi-1 ORF and the heterologous nucleotide sequence are in frame and the reporter gene lacks an endogenous stop codon. In one embodiment, the 3'-UTR or fragment thereof is human 3'-UTR of Bmi-1 or a fragment thereof. In another embodiment, the 3'-UTR or fragment thereof is murine 3'-UTR or a fragment thereof.

Nucleic acid sequences comprising the 5'-UTR of Bmi-1 or a fragment thereof, or the 3'-UTR of Bmi-1 or a fragment thereof, can be used to regulate the post-transcriptional expression of a protein translated from a mRNA transcript other than a Bmi-1 mRNA transcript. In a specific embodiment, nucleic acid sequences comprising nucleotides 1 to 505 of the 5'-UTR of human Bmi-1 (SEQ ID NO: 1), can be used to regulate the post-transcriptional expression of a protein translated from a mRNA transcript other than a Bmi-1 mRNA transcript. In another embodiment, nucleic acid sequences comprising nucleotides 1 to 471 of the 5'-UTR of murine Bmi-1 (SEQ ID NO: 7), can be used to regulate the post-transcriptional expression of a protein translated from a mRNA transcript other than a Bmi-1 mRNA transcript.

Nucleic Acid Constructs

The methods described herein provide for nucleic acid constructs comprising a reporter gene operably linked to any of the 5'-UTR and 3'-UTR of Bmi-1, or the 5'-UTR of Bmi-1 or the 3'-UTR of Bmi-1, or a fragment, mutant or a post-transcriptional regulatory element thereof, wherein the 5'-UTR is 5' (upstream) of the reporter gene and the 3'-UTR is 3' (downstream) of the reporter gene. Any of the 5'-UTR of Bmi-1, or a fragment, mutant or a post-transcriptional regulatory element thereof and the 3'-UTR of Bmi-1 or a fragment, mutant or a post-transcriptional regulatory element thereof, or the 5'-UTR of Bmi-1, or a fragment, mutant or a post-transcriptional regulatory element thereof, or the 3'-UTR of Bmi-1 or a fragment, mutant or a post-transcriptional regulatory element thereof, can be from or derived from any species. In certain embodiments, the 5'-UTR of Bmi-1 or a fragment, mutant or a post-transcriptional regulatory element thereof, is from or derived from human Bmi-1. In a certain embodiments, the 3'-UTR of Bmi-1 or a fragment, mutant or a post-transcriptional regulatory element thereof, is from or derived from human Bmi-1.

In one embodiment, the nucleic acid construct comprises the 5'-UTR of human Bmi-1 or a fragment thereof and the 3'-UTR of human Bmi-1 or a fragment thereof. In another embodiment, the nucleic acid construct comprises the 5'-UTR of human Bmi-1 or a fragment thereof or the 3'-UTR of human Bmi-1 or a fragment thereof. The nucleic acid constructs described herein may be used in the screening methods described herein, to identify or validate compounds that post-transcriptionally decrease or down-regulate the expression of a protein translated from a Bmi-1 mRNA transcript.

An embodiment of the nucleic acid construct described herein comprises the 5'-UTR of Bmi-1 or a fragment, mutant or a post-transcriptional regulatory element thereof and a reporter gene, wherein the 5'-UTR or a fragment, mutant or a post-transcriptional regulatory element thereof is operably linked to the reporter gene and the 5'-UTR or a fragment, mutant or a post-transcriptional regulatory element thereof is 5' (upstream) of the reporter gene. In a specific embodiment, the nucleic acid construct comprises the 5'-UTR of human Bmi-1 (see, e.g., FIG. 1; SEQ ID NO: 1) or a fragment, mutant or a post-transcriptional regulatory element thereof.

An embodiment of the nucleic acid construct described herein comprises the 3'-UTR of Bmi-1 or a fragment, mutant or a post-transcriptional regulatory element thereof, wherein the 3'-UTR or a fragment, mutant or a post-transcriptional regulatory element thereof is operably linked to the reporter gene and the 3'-UTR or a fragment, mutant or a post-transcriptional regulatory element thereof is 3' (downstream) of the reporter gene. In a specific embodiment, the nucleic acid construct comprises the 3'-UTR of human Bmi-1 (see, e.g., FIG. 2; SEQ ID NO: 2) or a fragment, mutant or a post-transcriptional regulatory element thereof.

Another embodiment of the nucleic acid construct described herein comprises the 5'-UTR of Bmi-1 or a fragment, mutant or a post-transcriptional regulatory element thereof, a reporter gene, and the 3'-UTR of Bmi-1 or a fragment, mutant or a post-transcriptional regulatory element thereof, wherein the 5'-UTR or a fragment, mutant or a post-transcriptional regulatory element thereof and 3'-UTR or a fragment, mutant or a post-transcriptional regulatory element thereof are operably linked to the reporter gene, and wherein the 5'-UTR or a fragment, mutant or a post-transcriptional regulatory element thereof is 5'(upstream) of the reporter gene and the 3'-UTR or a fragment, mutant or a post-transcriptional regulatory element thereof is 3' (downstream) of the reporter gene. In a specific embodiment, the nucleic acid construct comprises the 5'-UTR of human Bmi-1 (see, e.g., FIG. 1; SEQ ID NO: 1) or a fragment, mutant or a post-transcriptional regulatory element thereof, a reporter gene, and the 3'-UTR of human Bmi-1 (see, e.g., FIG. 2; SEQ ID NO: 2) or a fragment, mutant or a post-transcriptional regulatory element thereof.

In some embodiments, the nucleic acid construct comprises a reporter gene operably linked to the 5'-UTR of Bmi-1 or a fragment, mutant or post-transcriptional regulatory element thereof and an amino terminal fragment of the Bmi-1 ORF, (e.g., the first 3, 6, 9, 12, 15, 18, 21, 24, or more nucleotides of the ORF of Bmi-1), wherein the reporter gene is in frame with the amino terminal fragment of the ORF of Bmi-1, and wherein the 5'-UTR of Bmi-1 or a fragment, mutant or post-transcriptional regulatory element thereof and the amino terminal fragment of the Bmi-1 ORF are upstream of the reporter gene. In certain embodiments, the reporter gene lacks an endogenous start codon. In specific embodiments, the nucleic acid construct comprises the 3'-UTR of human Bmi-1 or a fragment, mutant or post-transcriptional regulatory element thereof, the reporter gene lacks an endogenous stop codon and the first 21 nucleotides of the ORF from the 5' end of human Bmi-1.

In some embodiments, the nucleic acid construct comprises a reporter gene operably linked to a carboxy terminal fragment of the Bmi-1 ORF (e.g., the last 3, 6, 9, 12, 15, 18, 21, 24, or more nucleotides from the 3' end of the ORF of Bmi-1) and the 3'-UTR of Bmi-1 or a fragment, mutant or post-transcriptional regulatory element thereof, wherein the reporter gene is in frame with the carboxy terminal fragment of the Bmi-1 ORF and the reporter gene lacks an endogenous stop codon, and wherein the carboxy terminal fragment of the ORF of Bmi-1 and the 3'-UTR or fragment, mutant or post-transcriptional regulatory element thereof are downstream of the reporter gene. In specific embodiments, the nucleic acid construct comprises the 3'-UTR of human Bmi-1 and the last 21 nucleotides of the ORF from the 3' end of human Bmi-1.

In some embodiments, the nucleic acid construct comprises a reporter gene operably linked to (i) the 5'-UTR of Bmi-1 or a fragment, mutant or post-transcriptional regulatory element thereof and an amino terminal fragment of the Bmi-1 ORF, (e.g., the first 3, 6, 9, 12, 15, 18, 21, 24, or more nucleotides of the ORF of Bmi-1); and (ii) a carboxy terminal fragment of the Bmi-1 ORF (e.g., the last 3, 6, 9, 12, 15, 18, 21, 24, or more nucleotides of the ORF of Bmi-1) and the 3'-UTR of Bmi-1 or a fragment, mutant or post-transcriptional regulatory element thereof, wherein the reporter gene is in frame with the amino terminal and carboxy terminal fragments of the ORF of Bmi-1 and the reporter gene lacks an endogenous stop codon, and wherein the 5'-UTR of Bmi-1 or a fragment, mutant or post-transcriptional regulatory element thereof and the amino terminal fragment of the Bmi-1 ORF are upstream of the reporter gene, and the carboxy terminal fragment of the ORF of Bmi-1 and the 3'-UTR of Bmi-1 or a fragment, mutant or post-transcriptional regulatory element thereof are downstream of the reporter gene. In certain embodiments, the reporter gene lacks an endogenous start codon. In specific embodiments, the nucleic acid construct comprises the 5'-UTR of human Bmi-1 and the first 21 nucleotides of the ORF from the 5' end of human Bmi-1. In another specific embodiment, the nucleic acid construct comprises nucleic acid residues 1 to 505 of the 5'-UTR of human Bmi-1 and the first 21 nucleotides of the ORF from the 5' end of human Bmi-1. In other specific embodiments, the nucleic acid construct comprises the last 21 nucleotides of the ORF from the 3' end of human Bmi-1 and the 3'-UTR of Bmi-1 or a fragment, mutant or post-transcriptional regulatory element thereof.

The nucleic acid constructs described herein comprise a reporter gene and a nucleotide sequence comprising a mutated form of the 5'-UTR of Bmi-1 or a fragment thereof, wherein the nucleotide sequence is operably linked to the reporter gene and the nucleotide sequence is upstream of the reporter gene. The nucleic acid constructs described herein comprise a reporter gene and a nucleotide sequence comprising a mutated form of the 3'-UTR of Bmi-1 or fragment thereof, wherein the nucleotide sequence is operably linked to the reporter gene and the nucleotide sequence is downstream of the reporter gene. The nucleic acid constructs described herein comprise a reporter gene, a first nucleotide sequence comprising a mutated form of the 5'-UTR of Bmi-1 or a fragment thereof, and a second nucleotide sequence comprising a mutated form of the 3'-UTR of Bmi-1 or a fragment thereof, wherein the first nucleotide sequence and the second nucleotide sequence are operably linked to the reporter gene, and wherein the first nucleotide sequence is upstream of the reporter gene and the second nucleotide sequence is downstream of the reporter gene. In an embodiment, either or both the mutated form of the 5'-UTR of Bmi-1 or a fragment thereof or the 3'-UTR of Bmi-1 or a fragment thereof is from human Bmi-1. In another embodiment, the mutated form of the 5'-UTR of Bmi-1 comprises an IRES sequence.

The nucleic acid constructs described herein comprise a reporter gene, a first nucleotide sequence comprising a mutated form of the 5'-UTR of Bmi-1 or a fragment thereof, and a second nucleotide sequence comprising a wild-type form of the 3'-UTR of Bmi-1 or a fragment thereof, wherein the first nucleotide sequence and the second nucleotide sequence are operably linked to the reporter gene, and wherein the first nucleotide sequence is upstream of the reporter gene and the second nucleotide sequence is downstream of the reporter gene. The nucleic acid constructs described herein also may comprise a reporter gene, a first nucleotide sequence comprising a wild-type form of the 5'-UTR of Bmi-1 or a fragment thereof, and a second nucleotide sequence comprising a mutant form of the 3'-UTR of Bmi-1 or a fragment thereof, wherein the first nucleotide sequence and the second nucleotide sequence are operably linked to the reporter gene, and wherein the first nucleotide sequence is 5'(upstream) of the reporter gene and the second nucleotide sequence is 3'(downstream) of the reporter gene. The nucleic acid constructs described herein may comprise a reporter gene, a first nucleotide sequence comprising a mutated form of the 5'-UTR of Bmi-1 or a fragment thereof, and a second nucleotide sequence comprising a mutated form of the 3'-UTR of Bmi-1 or a fragment thereof, wherein the first nucleotide sequence and the second nucleotide sequence are operably linked to the reporter gene, and wherein the first nucleotide sequence is upstream of the reporter gene and the second nucleotide sequence is downstream of the reporter gene. As used herein, the term "wild-type" refers to a naturally occurring UTR of Bmi-1.

In certain embodiments, a mutated form of the 5'-UTR of Bmi-1 or a fragment thereof contains 1, 2, 3, 4, 5, 6, 7, 8, 9, 10 or more mutations. Alternatively, the mutated form of the 5'-UTR of Bmi-1 or a fragment thereof contains an amount of mutations in a range of from about one to about five mutations, from about two to about eight mutations or from about five to about ten mutations. In certain embodiments, a mutated form of the 3' UTR of Bmi-1 or a fragment thereof contains 1, 2, 3, 4, 5, 6, 7, 8, 9, 10 or more mutations. Alternatively, the mutated form of the 3'-UTR of Bmi-1 or a fragment thereof contains an amount of mutations in a range of from about one to about five mutations, from about two to about eight mutations or from about five to about ten mutations. In either case, such mutations may include, but are not limited to, insertions, deletions, and/or substitutions.

In certain embodiments, a nucleotide sequence comprising a mutated form of the 5'-UTR of Bmi-1 is 65%, 75%, 80%, 85%, 90%, 95%, 98% or 99% identical to the nucleotide sequence of the 5'-UTR of Bmi-1 (e.g., the 5'-UTR of Bmi-1 is from human Bmi-1, see FIG. 1; SEQ ID NO: 1). In some embodiments, a nucleotide sequence comprising a mutated form of the 3'-UTR of Bmi-1 (e.g., the 3'-UTR of Bmi-1 is from human Bmi-1, see FIG. 2; SEQ ID NO: 2) is 65%, 75%, 80%, 85%, 90%, 95%, 98% or 99% identical to the nucleotide sequence of the 3'-UTR of Bmi-1 (e.g., the 3'-UTR of Bmi-1 is from human Bmi-1, see FIG. 2; SEQ ID NO: 2). Percent identity can be determined using any method known to one of skill in the art. In a specific embodiment, the percent identity is determined using the "Best Fit" or "Gap" program of the Sequence Analysis Software Package™ (Version 10; Genetics Computer Group, Inc., University of Wisconsin Biotechnology Center, Madison, Wis.). See, e.g., U.S. Patent Application Publication No. US 2005/0048549, paragraph 74, for information regarding these programs.

In certain embodiments, a nucleotide sequence comprising a mutated form of the 5'-UTR of Bmi-1 hybridizes to the nucleotide of the 5'-UTR of Bmi-1 (e.g., the 5'-UTR of Bmi-1 is from human Bmi-1, see FIG. 1; SEQ ID NO: 1). In certain embodiments, a nucleotide sequence comprising a mutated form of the 3'-UTR of Bmi-1 hybridizes to the nucleotide of the 3'-UTR of Bmi-1 (e.g., the 3'-UTR of Bmi-1 is from human Bmi-1, see FIG. 2; SEQ ID NO: 2).

In specific embodiments, a nucleotide sequence comprising a mutated form of the 5'-UTR of Bmi-1 hybridizes under stringent conditions to a nucleotide sequence of the 5'-UTR of Bmi-1 (e.g., the 5'-UTR of Bmi-1 is from human Bmi-1, see FIG. 1; SEQ ID NO: 1) of at least 20 nucleic acids, at least 30 nucleic acids, at least 40 nucleic acids, at least 50 nucleic acids, at least 100 nucleic acids, or at least 150 nucleic acids. In a specific embodiment, a nucleotide sequence comprising a mutated form of the 5'-UTR of Bmi-1 hybridizes under high stringency, intermediate or lower stringency hybridization conditions to a nucleotide sequence of the 5'-UTR of Bmi-1 or a fragment thereof. In specific embodiments, a nucleotide sequence comprising a mutated form of the 3'-UTR of Bmi-1 hybridizes under stringent conditions to a nucleotide sequence of the 3'-UTR of Bmi-1 (e.g., the 3'-UTR of Bmi-1 is from human Bmi-1, see FIG. 2; SEQ ID NO: 2) of at least 20 nucleic acids, at least 30 nucleic acids, at least 40 nucleic acids, at least 50 nucleic acids, at least 100 nucleic acids, or at least 150 nucleic acids. In a specific embodiment, a nucleotide sequence comprising a mutated form of the 3'-UTR of Bmi-1 hybridizes under high stringency, intermediate or lower stringency hybridization conditions to a nucleotide sequence of the 3'-UTR of Bmi-1 or a fragment thereof. Hybridization conditions are well known in the art and are described in e.g., U.S. Patent Application Publication No. US 2005/0048549 (e.g., paragraphs 72 and 73), which is herein incorporated by reference in its entirety.

In one embodiment, if only the 5'-UTR of Bmi-1 is used in a nucleic acid construct described herein, then the construct may further comprise a different UTR (unrelated to Bmi-1) as the 3'-UTR. In another embodiment, if only the 3'-UTR of Bmi-1 is used in a nucleic acid construct described herein, then the construct may further comprise a different UTR (unrelated to Bmi-1) as the 5'-UTR. In one embodiment, the different UTR may encompass the UTR of any gene that is not Bmi-1 or a UTR not found in nature.

The nucleic acid constructs described herein may comprise a reporter gene and a nucleotide sequence comprising a post-transcriptional regulatory element in any of the 5'-UTR and 3'-UTR, or the 5'-UTR or the 3'-UTR of Bmi-1. FIGS. 1 and 2 identify post-transcriptional regulatory elements in the 5'-UTR of human Bmi-1 (FIG. 1) and the 3'-UTR of human Bmi-1 (FIG. 2). In one embodiment, the post-transcriptional regulatory element comprises less than 505 nucleotides of the 5'-UTR of human Bmi-1. In one embodiment, the nucleic acid constructs may comprise a reporter gene and a nucleotide sequence comprising two, three, four or more post-transcriptional regulatory elements in any of the 5'-UTR and 3'-UTR, or the 5'-UTR or the 3'-UTR of Bmi-1.

In some embodiments, either or both the 5'-UTR of Bmi-1 and the 3'-UTR of Bmi-1 may be mutated to reduce the secondary or tertiary structure of the UTR. One skilled in the art would know how and be able to identify those regions of the 5'-UTR or 3'-UTR that contribute to the secondary or tertiary structure of the UTR using techniques known to one of skill in the art. Once those regions contributing to the secondary or tertiary structure of the 5'-UTR or 3'-UTR have been identified, one of skill in the art would be able to identify which nucleotides to mutate to reduce the secondary or tertiary structure of the UTR and be able to make such mutations using techniques known to one of skill in the art. By way of example, the MFOLD program can be used to determine the affect different mutations would have on the secondary structure of the Bmi-1 mRNA transcripts (see, *MFOLD*: Prediction of RNA secondary structure (M. Zuker) http://bioweb.pasteur.fr/seqanal/interfaces/mfold-simple.html).

In some embodiments, the nucleic acid construct may further comprise a stable hairpin secondary structure inserted into a UTR of Bmi-1. In some embodiments, an intron is inserted into a UTR (e.g., the 5'-UTR) or at the 5' end of an ORF of Bmi-1. In some embodiments, both a stable hairpin secondary structure and an intron are added to the nucleic acid construct. Such insertions and other techniques known to one of skill in the art can be used to obtain a nucleic acid construct suitable for the methods described herein.

The reporter gene in the nucleic acid constructs can be positioned such that the translation of that reporter gene is dependent upon the mode of translation initiation, such as, but not limited to, cap-dependent translation or cap-independent translation (i.e., translation via an internal ribosome entry site).

In addition to any of the 5'-UTR and 3'-UTR, or the 5'-UTR or the 3'-UTR of Bmi-1 and the reporter gene, the nucleic acid construct may further comprise one or more transcriptional regulatory element(s). The transcriptional regulatory elements are typically located upstream of the 5'-UTR of Bmi-1 and direct the transcription of the reporter gene. In some embodiments, one or more of the transcriptional regulatory elements that are endogenous to the Bmi-1 transcriptional regulatory elements are used to control the transcription of a reporter gene. In other embodiments, one or more transcriptional regulatory elements that are heterologous to Bmi-1 are used to control the transcription of a reporter gene. Any transcriptional regulatory element(s) known to one of skill in the art may be used to control the transcription of the reporter gene. Non-limiting examples of the types of transcriptional regulatory element(s) include a constitutive promoter, a tissue-specific promoter, and an inducible promoter. In a specific embodiment, the transcription of the reporter gene is controlled, at least in part, by a mammalian (in some embodiments, human) transcriptional regulatory element(s). In one embodiment, the nucleic acid construct described herein may optionally comprise one or more promoters operably linked to the reporter gene. In a more specific embodiment, the transcription of the reporter gene is controlled, at least in part, by a strong promoter, such as CMV.

Specific examples of promoters which may be used to control the transcription of the reporter gene include, but are not limited to, the SV40 early promoter region, the promoter contained in the 3' long terminal repeat of Rous sarcoma virus, the herpes thymidine kinase promoter, the regulatory sequences of the metallothionein gene adenovirus (ADV), cytomegalovirus (CMV), bovine papilloma virus (BPV), parovirus B19p6 promoter, prokaryotic expression vectors such as the .beta.-lactamase promoter, or the tac promoter, plant expression vectors comprising the nopaline synthetase promoter region or the cauliflower mosaic virus 35S RNA promoter, and the promoter of the photosynthetic enzyme ribulose biphosphate carboxylase, promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells, insulin gene control region which is active in pancreatic beta cells, immunoglobulin gene control region which is active in lymphoid cells, mouse mammary tumor virus control region which is active in testicular, breast, lymphoid and mast cells, albumin gene control region which is active in liver, alpha-fetoprotein gene control region which is active in liver, alpha 1-antitrypsin gene control region which is active in the liver, beta-globin gene control region which is active in myeloid cells, myelin basic protein gene control region which is active in oligodendrocyte cells in the brain, myosin light chain-2 gene control region which is active in skeletal muscle, and gonadotropic releasing hormone gene control region which is active in the hypothalamus.

The nucleic acid constructs may be part of or otherwise contained in a vector that provides transcriptional regulatory elements and optionally, translational regulatory elements. The vector chosen will depend upon a variety of factors, including, without limitation, the strength of the transcriptional regulatory elements and the host cell or cell-free translation extract to be used to express the reporter gene. Non-limiting examples of host cell-vector systems that may be used to express the reporter gene include mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA; and stable cell lines generated by transformation using a selectable marker.

In one embodiment, vectors may comprise a nucleic acid construct as described herein. In a certain embodiment, a vector comprises a nucleic acid construct, wherein the nucleic acid construct comprises a reporter gene operably linked to (i) the 5'-UTR (untranslated region) of Bmi-1 or a fragment, mutant or post-transcriptional regulatory element thereof and the 3'-UTR of Bmi-1 or a fragment, mutant or post-transcriptional regulatory element thereof, (ii) the 5'-UTR of Bmi-1 or a fragment, mutant or post-transcriptional regulatory element thereof; or (iii) the 3'-UTR of Bmi-1 or a fragment, mutant or post-transcriptional regulatory element thereof, wherein the 5'-UTR or fragment, mutant or post-transcriptional regulatory element thereof is upstream of the reporter gene and the 3'-UTR or fragment, mutant or post-transcriptional regulatory element thereof is downstream of the reporter gene.

In a specific embodiment, a nucleic acid construct comprises a promoter operably linked to a reporter gene flanked by one or both UTRs of Bmi-1, origins of replication from one or more species, and optionally, one or more selectable markers (e.g., an antibiotic resistance gene). In one embodiment, the nucleic acid construct is a vector a CMV vector, such as pcDNA™3.1/Hygro (Invitrogen Corp., Carlsbad, Calif.). In other embodiments, the nucleic acid construct is a vector a T7 vector, a lac vector, pCEP4 vector or 5.0/FRT vector.

The nucleic acid constructs can be monocistronic or multicistronic. A multicistronic nucleic acid construct may encode 2, 3, 4, 5, 6, 7, 8, 9, 10 or more, or in the range of 2-5, 5-10 or 10-20 reporter genes. For example, a bicistronic nucleic acid construct may comprise in the following order a promoter, a first reporter gene, a 5'-UTR of Bmi-1, a second reporter gene and optionally, a 3'-UTR of Bmi-1. In such a nucleic acid construct, the transcription of both reporter genes is driven by the promoter, whereas the translation of the first reporter protein mRNA from the first reporter gene is by a cap-dependent scanning mechanism and the translation of the second reporter protein mRNA from the second reporter gene is by a cap-independent mechanism via an IRES. The IRES-dependent translation of the second reporter protein mRNA by the second reporter gene can be normalized against cap-dependent translation.

For example, a bicistronic construct can be made comprising, in the following order, a cap, a promoter, a first heterologous nucleotide sequence (e.g., a first reporter gene), the 5' UTR of a Bmi-1 gene or a fragment thereof, a second heterologous nucleotide sequence (e.g., second reporter gene), and optionally, the 3' UTR of a Bmi-1 gene or a fragment thereof. In such a reporter construct, the transcription of both reporter genes is capable of being driven by the promoter. The translation of the reporter protein mRNA from the first reporter gene is by a cap-dependent scanning mechanism and the translation of the reporter protein mRNA from the second reporter gene is by a cap-independent mechanism via an IRES. The IRES-dependent translation of the mRNA of the second reporter gene can be normalized against cap-dependent translation.

In some embodiments, a bicistronic construct comprises in the following 5' to 3' order, a cap, a promoter, a first heterologous nucleotide sequence, a 5'-UTR of Bmi-1 or a fragment thereof comprising the IRES sequence of the 5'-UTR of Bmi-1, a second heterologous nucleotide sequence and optionally, the 3'-UTR of Bmi-1 or a fragment, mutant or post-transcriptional regulatory element thereof, or a 3'-UTR that is different from the 3-UTR of Bmi-1 or a fragment, mutant or post-transcriptional regulatory element thereof. In some embodiments, a bicistronic construct comprises in the following 5' to 3' order: a cap, a promoter, a first heterologous nucleotide sequence, a 5'-UTR of human Bmi-1 or a fragment thereof comprising the IRES sequence of the 5'-UTR of human Bmi-1, a second heterologous nucleotide sequence and optionally, the 3'-UTR of human Bmi-1 or a fragment, mutant or post-transcriptional regulatory element thereof, or a 3'-UTR that is different from the 3-UTR of human Bmi-1 or a fragment, mutant or post-transcriptional regulatory element thereof. In some embodiments, a bicistronic construct comprises in the following 5' to 3' order, a cap, a promoter, a first heterologous nucleotide sequence, a 5'-UTR of murine Bmi-1 or a fragment thereof comprising the IRES sequence of the 5'-UTR of murine Bmi-1, a second heterologous nucleotide sequence and optionally, the 3'-UTR of murine Bmi-1 or a fragment, mutant or post-transcriptional regulatory element thereof, or a 3'-UTR that is different from the 3-UTR of murine Bmi-1 or a fragment, mutant or post-transcriptional regulatory element thereof.

In some embodiments, a bicistronic construct comprises in the following 5' to 3' order: a cap, a promoter, a first heterologous nucleotide sequence, a 5'-UTR of human Bmi-1 or a fragment thereof comprising the IRES sequence of the 5'-UTR of human Bmi-1, an amino terminal fragment of the human Bmi-1 ORF, (e.g., the first 3, 6, 9, 12, 15, 18, 21, 24, or more nucleotides of the ORF of Bmi-1), a second heterologous nucleotide sequence and optionally, the 3'-UTR of human Bmi-1 or a fragment, mutant or post-transcriptional regulatory element thereof, or a 3'-UTR that is different from the 3-UTR of human Bmi-1 or a fragment, mutant or post-transcriptional regulatory element thereof wherein the reporter gene is in frame with the second reporter gene. In a specific embodiment, the Bmi-1 is human Bmi-1. In certain embodiments, the second reporter gene lacks a start codon.

In specific embodiment, the first and second heterologous nucleotide sequences are reporter genes. In another specific embodiment, the first and second heterologous nucleotide sequences are different from each other (e.g., they are different reporter genes). In certain embodiments, the bicistronic construct is used in the methods described herein to identify compounds that modulate the post-transcriptional expression of Bmi-1. In other embodiments, the bicistronic construct is used to regulate the expression of a heterologous nucleotide sequence.

Expression vectors containing the nucleic acid construct described herein can be identified by four general approaches: (a) nucleic acid sequencing, (b) nucleic acid hybridization, (c) presence or absence of "marker" nucleic acid functions, and (d) expression of inserted sequences. In the first approach, the presence of the UTRs and/or the reporter gene inserted in an expression vector can be detected by sequencing. In the second approach, the presence of the UTRs and/or the reporter gene inserted in an expression vector can be detected by nucleic acid hybridization using probes comprising sequences that are homologous to the inserted UTRs and/or reporter gene. In the third approach, the recombinant vector/host system can be identified and selected based upon the presence or absence of certain "marker" nucleic acid functions (e.g., thymidine kinase activity, resistance to antibiotics, transformation phenotype, occlusion body formation in baculovirus, etc.) caused by the insertion of the nucleic acid of interest, i.e., the nucleic acid construct, in the vector. For example, if the nucleic acid of interest is inserted within the marker nucleic acid sequence of the vector, recombinants containing the insert can be identified by the absence of the marker nucleic acid function. In the fourth approach, recombinant expression vectors can be identified by assaying the reporter gene product expressed by the recombinant. Such assays can be based, for example, on the physical or functional properties of the particular reporter gene.

Techniques for practicing aspects of the methods described herein will employ, unless otherwise indicated, conventional techniques of molecular biology, microbiology, and recombinant DNA manipulation and production, which are routinely practiced by one of skill in the art.

Reporter Genes

Any reporter gene well-known to one of skill in the art may be used in the nucleic acid constructs to ascertain the effect of a compound on post-transcriptional expression of Bmi-1. Reporter genes refer to a nucleotide sequence encoding or coding for a protein that is readily detectable, when expressed, either by its presence, amount or activity. A reporter gene can encode or code for a fusion protein. In one embodiment, the fusion protein is encoded or coded by a nucleic acid sequence comprising a nucleotide sequence heterologous to Bmi-1 that is readily detectable and operably linked to the ORF of Bmi-1. In a specific embodiment, the fusion protein comprises Bmi-1 encoded or coded by a nucleotide sequence without a stop codon and a protein encoded by a heterologous nucleotide sequence without the start codon that has readily detectable protein expression, such as luciferase. In a specific embodiment, a reporter gene comprises a first nucleotide sequence encoding or coding for a protein that is readily detectable and is operably linked to a second nucleotide sequence encoding a peptide or protein, wherein the first and second nucleotide sequences not found in nature to be linked to each other (e.g., a second nucleotide sequence that is heterologous to the first nucleotide sequence).

Reporter genes may be obtained and the nucleotide sequence of the reporter gene determined by any method well-known to one of skill in the art. The nucleotide sequence of a reporter gene can be obtained, e.g., from the literature or a database such as GenBank. Alternatively, a polynucleotide encoding a reporter gene may be generated from nucleic acid from a suitable source. If a clone containing a nucleic acid encoding a particular reporter gene is not available, but the sequence of the reporter gene is known, a nucleic acid encoding the reporter gene may be chemically synthesized or obtained from a suitable source (e.g., a cDNA library, or a cDNA library generated from, or nucleic acid, preferably poly A+ RNA, isolated from, any tissue or cells expressing a reporter protein from the reporter gene) by PCR amplification. Once the nucleotide sequence of a reporter gene is determined, the nucleotide sequence of the reporter gene may be manipulated using methods well-known in the art for the manipulation of nucleotide sequences (e.g., recombinant DNA techniques, site directed mutagenesis, PCR, etc.) to generate reporter genes having a different amino acid sequence, for example to create amino acid substitutions, deletions, and/or insertions.

Examples of reporter genes whose expression is readily detectable in a screening method include, but are not limited to, nucleotide sequences encoding or coding for luciferase (e.g., firefly luciferase, renilla luciferase, and click beetle luciferase), green fluorescent protein ("GFP") (e.g., green fluorescent protein, yellow fluorescent protein, red fluorescent protein, cyan fluorescent protein, and blue fluorescent protein), beta-galactosidase ("b-gal"), beta-glucoronidase, beta-lactamase, chloramphenicol acetyltransferase ("CAT"), and alkaline phosphatase ("AP"). The characteristics and methods for using the aforementioned reporter genes are known to one of skill in the art. In one embodiment, a reporter gene utilized in the nucleic acid constructs is easily detected and has an activity which is not normally found in the cell or organism of interest. In another embodiment, a reporter gene utilized in the nucleic acid constructs is not Bmi-1, or a nucleotide sequence encoding or coding for the Bmi-1 protein. In another embodiment, a reporter gene utilizes an ORF other than luciferase, GFP, beta-galactosidase, CAT or AP.

Cells and Transfection Techniques

A host cell may be transformed or transfected with the nucleic acid construct described herein. In certain embodiments, the use of stable transformants is preferred. In one embodiment, the host cell is a mammalian cell. In another embodiment, the host cell is a human cell. In another embodiment, the host cells are primary cells isolated from a tissue or other biological sample of interest. Host cells that can be used in the methods described herein include, but are not limited to, hybridomas, pre-B cells, 293 cells, 293T cells, 293H cells, HeLa cells, HepG2 cells, 3T3 cells, MCF7 cells, SkBr3 cells, BT474 cells, a rhabdomyosarcoma cell line; a fibrosarcoma cell line such as HT1080; a myeloid leukemia cell line such as K562 or KG1; a glioblastoma cell line such as U87-MG or T98G; or a neuroblastoma cell line such as MC-IXC, SK-N-MC, SK-N-MC, SK-N-DZ, SH-SY5Y, and BE(2)-C. In one embodiment, the host cells are immortalized cell lines derived from a source, e.g., a tissue, specific to Bmi-1. In another embodiment, the host cells are fetal/embryonic cells. In yet another embodiment, the host cells are from an adult. In another embodiment, the host cells are stem cells. In a specific embodiment, the host cells are embryonic stem cells. Other host cells that can be used as described herein include, but are not limited to, bacterial cells, yeast cells, virally-infected cells, or plant cells.

Transformation may be by any known method for introducing polynucleotides into a host cell, for example by packaging the polynucleotide in a virus and transducing a host cell with the virus, and by direct uptake of the polynucleotide. The transformation procedure used depends upon the host to be transformed. Such methods are well-known to one of skill in the art.

In one embodiment, stable cell lines expressing a reporter protein via a nucleic acid construct of interest are generated for high throughput screening. Such stable cell lines may be generated by introducing a nucleic acid construct further comprising a selectable marker, allowing the cells to grow for 1-2 days in an enriched medium, and then growing the cells on a selective medium. The selectable marker in the recombinant plasmid confers resistance to the selection and allows cells to stably integrate the plasmid into their chromosomes and grow to form foci which in turn can be cloned and expanded into cell lines.

In some embodiments, a host cell contains a vector comprising a nucleic acid construct described herein. For example, in one embodiment, a host cell contains a vector comprising a nucleic acid construct, wherein the nucleic acid construct comprises a reporter gene operably linked to (i) the 5'-UTR of Bmi-1 or a fragment, mutant or post-transcriptional regulatory element thereof and a 3'-UTR of Bmi-1 or a fragment, mutant or post-transcriptional regulatory element thereof; (ii) the 5'-UTR of Bmi-1 or a fragment, mutant or post-transcriptional regulatory element thereof; or (iii) the 3'-UTR of Bmi-1 or a fragment, mutant or post-transcriptional regulatory element thereof, and wherein the 5'-UTR is 5' (upstream) of the reporter gene and the 3'-UTR is 3' (downstream) of the reporter gene.

Cell Free Extracts

The nucleic acid constructs may be translated in a cell-free system as described herein. Techniques for practicing this specific aspect will employ, unless otherwise indicated, conventional techniques of molecular biology, microbiology, and recombinant DNA manipulation and production, which are routinely practiced by one of skill in the art. Any technique well-known to one of skill in the art may be used to generate cell-free extracts for translation in vitro (otherwise referred to herein as a cell-free extract). For example, the cell-free extracts for in vitro translation reactions can be generated by centrifuging cells and clarifying the supernatant. In one embodiment, the cell-free extract contains a coupled transcription/translation system (e.g., Promega TNT®). In one embodiment, the cell-free extract contains a nucleic acid construct described herein.

The cell-free extract may be isolated from cells of any species origin. For example, the cell-free extract may be isolated from human cells (e.g., HeLA cells), 293 cells, Vero cells, yeast, mouse cells (e.g., cultured mouse cells), rat cells (e.g., cultured rat cells), Chinese hamster ovary (CHO) cells, *Xenopus oocytes*, rabbit reticulocytes, primary cells, cancer cells (e.g., undifferentiated cancer cells), cell lines, wheat germ, rye embryo, or bacterial cell extract. In a specific embodiment, the cells from which the cell-free extract is obtained do not endogenously express Bmi-1. In another embodiment, the cell-free extract is an extract isolated from human cells. In a further embodiment, the human cells that can be used in the methods described herein include, but are not limited to HeLa, 293, 293T, 293H, HeLa, HepG2, 3T3, MCF7, SkBr3, BT474, a rhabdomyosarcoma cell line; a fibrosarcoma cell line such as HT1080; a myeloid leukemia cell line such as K562 or KG1; a glioblastoma cell line such as U87-MG or T98G; or a neuroblastoma cell line such as MC-IXC, SK-N-MC, SK-N-MC, SK-N-DZ, SH-SY5Y or BE(2)C.

Screening Methods
Cell-Based Assays

Host cells transformed or transfected with the nucleic acid construct described herein may be used to screen, identify or validate compounds that modulate post-transcriptional or UTR-dependent expression of Bmi-1. In a specific embodiment, the method for identifying or validating a compound that modulates the post-transcriptional or UTR-dependent expression of Bmi-1 comprises the steps of: (a) contacting a compound with a host cell engineered to express a reporter protein via a nucleic acid construct described herein; and (b) detecting the amount or activity of the reporter protein translated from a mRNA transcript transcribed from the reporter gene, wherein a compound that modulates the post-transcriptional or UTR-dependent expression of Bmi-1 is identified or validated if the amount or activity of the reporter protein detected in the presence of the compound is altered relative to a previously determined reference range, or relative to the amount or activity of the reporter protein detected in the absence of the compound or the presence of a negative control.

In one embodiment, the host cell is stably transfected with a nucleic acid construct. In another embodiment, the host cell is engineered to stably express a reporter protein via the nucleic acid construct reporter gene encoding or coding for a reporter protein. In one embodiment, the host cell is transiently transfected with a nucleic acid construct. In another embodiment, the host cell is engineered to transiently express a reporter protein via the nucleic acid construct reporter gene encoding or coding for a reporter protein.

In one embodiment, the method for identifying or validating compounds that modulate the post-transcriptional expression of Bmi-1 may be conducted by: (a) contacting a compound with a host cell engineered to express a reporter protein via a nucleic acid construct comprising a reporter gene encoding or coding for a reporter protein operably linked to any of the 5'-UTR and 3'-UTR, or the 5'-UTR or the 3'-UTR of Bmi-1, or a fragment, mutant or post-transcriptional regulatory element thereof, wherein the 5'-UTR or fragment, mutant or post-transcriptional regulatory element thereof is upstream of the reporter gene and the 3'-UTR or a fragment, mutant or post-transcriptional regulatory element thereof is downstream of the reporter gene; and (b) measuring the expression of said reporter protein.

In one embodiment, the method for identifying or validating compounds that modulate the post-transcriptional expression of Bmi-1 may be conducted by: (a) contacting a compound with a host cell engineered to stably express a reporter protein via a nucleic acid construct comprising a reporter gene encoding or coding for a reporter protein operably linked to any of the 5'-UTR and 3'-UTR, or the 5'-UTR or the 3'-UTR of Bmi-1, or a fragment, mutant or post-transcriptional regulatory element thereof, wherein the 5'-UTR or fragment, mutant or post-transcriptional regulatory element thereof is upstream of the reporter gene and the 3'-UTR or a fragment, mutant or post-transcriptional regulatory element thereof is downstream of the reporter gene; and (b) measuring the expression of said reporter protein.

In one embodiment, the method for identifying or validating compounds that modulate the post-transcriptional expression of Bmi-1 may be conducted by: (a) contacting a compound with a host cell engineered to transiently express a reporter protein via a nucleic acid construct comprising a reporter gene encoding or coding for a reporter protein operably linked to any of the 5'-UTR and 3'-UTR, or the 5'-UTR or the 3'-UTR of Bmi-1, or a fragment, mutant or post-transcriptional regulatory element thereof, wherein the 5'-UTR or fragment, mutant or post-transcriptional regulatory element thereof is upstream of the reporter gene and the 3'-UTR or a fragment, mutant or post-transcriptional regulatory element thereof is downstream of the reporter gene; and (b) measuring the expression of said reporter protein.

In some embodiments, the nucleic acid construct comprises a reporter gene operably linked to the 5'-UTR of Bmi-1 or fragment, mutant or post-transcriptional regulatory element thereof and a 3'-UTR unrelated to Bmi-1, wherein the 5'-UTR of Bmi-1 or fragment, mutant or post-transcriptional regulatory element thereof is upstream of the reporter gene and the 3'-UTR is downstream of the reporter gene. In some embodiments, the nucleic acid construct comprises a reporter gene operably linked to a 5'-UTR unrelated to Bmi-1 and the 3'-UTR of Bmi-1 or fragment, mutant or post-transcriptional regulatory element thereof, wherein the 5'-UTR is upstream of the reporter gene and the 3'-UTR of Bmi-1 or fragment, mutant or post-transcriptional regulatory element thereof is downstream of the reporter gene. In one embodiment, any of the 5'-UTR and the 3'-UTR, or the 5'-UTR or the 3'-UTR of Bmi-1 are from human Bmi-1.

An alteration in the amount or activity of a reporter protein detected in the presence of a compound relative to a previously determined reference range, or relative to the amount or activity of the reporter protein detected in the absence of the compound or the presence of a negative control in such screening methods indicate that a particular compound modulates UTR-dependent expression of the reporter gene, and thus may modulate UTR-dependent expression of the Bmi-1 gene. In one embodiment, a negative control (e.g., PBS, DMSO or another agent that is known to have no effect on the expression of the reporter gene) and a positive control (e.g., an agent that is known to have an effect on the expression of the reporter gene, preferably an agent that affects untranslated region-dependent expression) are included in the cell-based screening methods described herein.

In a specific embodiment, the method for identifying or validating a compound that modulates UTR-dependent expression of Bmi-1 comprises: (a) contacting a compound with a host cell containing a nucleic acid construct comprising a reporter gene operably linked to any of the 5'-UTR and 3'-UTR, or the 5'-UTR or the 3'-UTR of Bmi-1, or a fragment, mutant or post-transcriptional regulatory element thereof, wherein the 5'-UTR or fragment, mutant or post-transcriptional regulatory element thereof is upstream of the reporter gene and the 3'-UTR of Bmi-1 or fragment, mutant or post-transcriptional regulatory element thereof is downstream of the reporter gene; and (b) detecting the amount or activity of a reporter protein translated from a mRNA transcript transcribed from said reporter gene, wherein a compound that modulates UTR-dependent expression of Bmi-1 is identified or validated if the amount or activity of said reporter protein detected in the presence of the compound is altered relative to a previously determined reference range, or relative to the amount or relative to activity of said reporter protein detected in the absence of said compound or the presence of a negative control. In a specific embodiment, a compound that modulates UTR-dependent expression of Bmi-1 is identified or validated if the amount or activity of said reporter protein detected in the presence of the compound is down-regulated relative to a previously determined reference range, or relative to the amount or activity of said reporter protein detected in the absence of said compound or the presence of a negative control. In a specific embodiment, the previously determined reference range is the amount or activity of said reporter protein detected in the presence of a negative control (e.g., PBS or DMSO).

The step of contacting a compound with a host cell expressing or genetically engineered to express a reporter protein via a nucleic acid construct comprising a reporter gene encoding or coding for said reporter protein operably linked to any of the 5'-UTR and 3'-UTR, or the 5'-UTR or the 3'-UTR of Bmi-1, or a fragment, mutant or post-transcriptional regulatory element thereof may be conducted under physiologic conditions. In a specific embodiment, a compound is contacted with the host cells in the presence of an aqueous solution. In accordance with this embodiment, the aqueous solution may comprise a buffer and a combination of salts, preferably approximating or mimicking physiologic conditions. Alternatively, the aqueous solution may comprise a buffer, a combination of salts, and a detergent or a surfactant. Examples of salts which may be used in the aqueous solution include, but not limited to, KCl, NaCl, and/or $MgCl_2$. The optimal concentration of each salt used in the aqueous solution is dependent on the host cells and compounds used and can be determined using routine experimentation.

In one embodiment, the method for identifying or validating a compound that modulates UTR-dependent expression of Bmi-1 provides for contacting a compound with a host cell expressing or genetically engineered to stably or transiently express a reporter protein via a nucleic acid construct comprising a reporter gene encoding or coding for said reporter protein operably linked to any of the 5'-UTR and 3'-UTR, or the 5'-UTR or the 3'-UTR of Bmi-1, or a fragment, mutant or post-transcriptional regulatory element thereof for a specific period of time. For example, the contacting can take place for about 1 minute, 2 minutes, 3 minutes, 4, minutes, 5, minutes, 10 minutes, 15 minutes, 20 minutes, 30 minutes, 1 hour, 2 hours, 3 hours, 4 hours, 5 hours, 10 hours, 15 hours, 20 hours, 1 day, 2 days, 3 days, 4 days, 5 days, or 1 week. In one embodiment, the contacting is about 15 hours, i.e., overnight. The contacting can take place for about 1 minute to 1 week, preferably about 5 minutes to 5 days, more preferably about 10 minutes to 2 days, and even more preferably about 1 hour to 1 day.

In one embodiment, the method for identifying or validating a compound that modulates UTR-dependent expression of Bmi-1 comprises: (a) engineering a host cell to stably or transiently express a reporter protein via a nucleic acid construct comprising a reporter gene encoding or coding for said reporter protein operably linked to the any of the 5'-UTR and 3'-UTR, or the 5'-UTR or the 3'-UTR of Bmi-1 or a fragment, mutant or post-transcriptional regulatory element thereof, wherein the 5'-UTR or fragment, mutant or post-transcriptional regulatory element thereof is upstream of the reporter gene and the 3'-UTR of Bmi-1 or fragment, mutant or post-transcriptional regulatory element thereof is downstream of the reporter gene; (b) contacting said cell with a compound; and (c) detecting the amount or activity of said reporter protein, wherein a compound that modulates UTR-dependent expression Bmi-1 is identified if the amount or activity of said reporter protein detected in the presence of the compound is altered relative to a previously determined reference range or relative to the amount or activity of said reporter protein detected in the absence of said compound or the presence of a negative control (e.g., phosphate buffered saline ("PBS") or dimethyl sulfoxide ("DMSO")). In a specific embodiment, the previously determined reference range is the amount or activity of said reporter protein detected in the presence of a negative control (e.g., PBS or DMSO).

In another embodiment, the method for identifying or validating a compound that modulates UTR-dependent expression of Bmi-1 comprises: (a) contacting a compound with a host cell expressing a reporter protein via a nucleic acid construct comprising a reporter gene encoding or coding for said reporter protein operably linked to any of the 5'-UTR and 3'-UTR, or the 5'-UTR or the 3'-UTR of Bmi-1, or a fragment, mutant or post-transcriptional regulatory element thereof, wherein the 5'-UTR of Bmi-1 or fragment, mutant or post-transcriptional regulatory element thereof is upstream of the reporter gene and the 3'-UTR of Bmi-1 or fragment, mutant or post-transcriptional regulatory element thereof is downstream of the reporter gene; and (b) detecting the amount or activity of said reporter protein, wherein a compound that modulates UTR-dependent expression of Bmi-1 is identified or validated if the amount or activity of said reporter protein detected in the presence of the compound is altered relative to a previously determined reference range or relative to the amount or activity of said reporter protein detected in the absence of said compound or the presence of a negative control (e.g., PBS or DMSO). In a specific embodiment, the previously determined reference range is the amount or activity of said reporter protein in the presence of a negative control (e.g., PBS or DMSO).

In another embodiment, the method for identifying or validating a compound that decreases or down-regulates UTR-dependent expression of Bmi-1 comprises (a) contacting a compound with a host cell expressing a reporter protein via a nucleic acid construct comprising a reporter gene encoding or coding for said reporter protein operably linked to any of the 5'-UTR and 3'-UTR, or the 5'-UTR or the 3'-UTR of Bmi-1, or a fragment, mutant or post-transcriptional regulatory element thereof, wherein the 5'-UTR of Bmi-1 or fragment, mutant or post-transcriptional regulatory element thereof is upstream of the reporter gene and the 3'-UTR of Bmi-1 or fragment, mutant or post-transcriptional regulatory element thereof is downstream of the reporter gene; and (b) detecting the amount or activity of said reporter protein, wherein a compound that decreases or down-regulates UTR-dependent expression of Bmi-1 is identified or validated if the amount or activity of said reporter protein detected in the presence of the compound is decreased relative to a previously determined reference range, or relative to the amount or activity of said reporter protein detected in the absence of the compound or the presence of a negative control (e.g., PBS or DMSO). In a specific embodiment, the previously determined reference range is the amount or activity of said reporter protein detected in the presence of a negative control (e.g., PBS or DMSO). In certain embodiments, the decrease or down-regulation in the amount or activity of said reporter protein is at least 1.5 fold, 2 fold, 3 fold, 4 fold, 5 fold, 6 fold, 7 fold, 8 fold, 9 fold, or 10 fold less than the amount of activity of said reporter protein detected in the absence of the compound or in the presence of a negative control. In a specific embodiment, the amount or activity of said reporter protein is detected by the same technique when the host cell is contacted with the compound or a control (such as a negative control). In one embodiment, the technique is an immunological technique, such as an ELISA, western blot, etc.

In another embodiment, the method for identifying or validating a compound that modulates UTR-dependent expression of Bmi-1 comprises the steps of: (a) contacting a compound with a host cell containing a nucleic acid construct comprising a reporter gene operably linked to the 5'-UTR of Bmi-1 or a fragment, mutant or post-transcriptional regulatory element thereof and an amino terminal fragment of the Bmi-1 ORF, (e.g., the first 3, 6, 9, 12, 15, 18, 21, 24, or more nucleotides of the ORF of Bmi-1), wherein the reporter gene is in frame with the amino terminal fragment of the ORF of Bmi-1, and wherein the 5'-UTR of Bmi-1 or a fragment, mutant or post-transcriptional regulatory element thereof and the amino terminal fragment of the Bmi-1 ORF are upstream of the reporter gene; and (b) detecting the amount or activity of a reporter protein translated from a mRNA transcript transcribed from said reporter gene, wherein a compound that modulates UTR-dependent expression of Bmi-1 is identified or validated if the amount or activity of said reporter protein detected in the presence of the compound is altered relative to a previously determined reference range, or relative to the amount or activity of said reporter protein detected in the absence of said compound or the presence of a negative control. In one embodiment, a compound that down-regulates UTR-dependent expression of Bmi-1 is identified or validated if the amount or activity of said reporter protein detected in the presence of the compound is down-regulated or reduced relative to a previously determined reference range, or relative to the amount or activity of said reporter protein detected in the absence of said compound or the presence of a negative control. In certain embodiments, the reporter gene lacks an endogenous start codon. In specific embodiments, the nucleic acid construct comprises the 5'-UTR of human Bmi-1 and the first 21 nucleotides of the ORF from the 5' end of human Bmi-1. In another specific embodiment, the nucleic acid construct comprises nucleic acid residues 1 to 505 of the 5'-UTR of human Bmi-1 and the first 21 nucleotides of the ORF from the 5' end of human Bmi-1.

In another embodiment, the method for identifying or validating a compound that modulates UTR-dependent expression of Bmi-1 comprises the steps of: (a) contacting a compound with a host cell containing a nucleic acid construct comprising a reporter gene operably linked to a carboxy terminal fragment of the Bmi-1 ORF (e.g., the last 3, 6, 9, 12, 15, 18, 21, 24, or more nucleotides of the ORF of Bmi-1) and the 3'-UTR of Bmi-1 or a fragment, mutant or post-transcriptional regulatory element thereof, wherein the reporter gene is in frame with the carboxy terminal fragment of the Bmi-1 ORF and the reporter gene lacks an endogenous stop codon, and wherein the carboxy terminal fragment of the ORF of Bmi-1 and the 3'-UTR of Bmi-1 or a fragment, mutant or post-transcriptional regulatory element thereof are downstream of the reporter gene; and (b) detecting the amount or activity of a reporter protein translated from a mRNA transcript transcribed from said reporter gene, wherein a compound that modulates UTR-dependent expression of Bmi-1 is identified or validated if the amount or activity of said reporter protein detected in the presence of the compound is altered relative to a previously determined reference range, or relative to the amount or activity of said reporter protein detected in the absence of said compound or the presence of a negative control. In one embodiment, a compound that down-regulates UTR-dependent expression of Bmi-1 is identified or validated if the amount or activity of said reporter protein detected in the presence of the compound is down-regulated or reduced relative to a previously determined reference range, or relative to the amount or activity of said reporter protein detected in the absence of said compound or the presence of a negative control.

In another embodiment, the method for identifying or validating a compound that modulates UTR-dependent expression of Bmi-1 comprises the steps of: (a) contacting a compound with a host cell containing a nucleic acid construct comprising a reporter gene operably linked to (i) the 5'-UTR of Bmi-1 or a fragment, mutant or post-transcriptional regulatory element thereof and an amino terminal fragment of the Bmi-1 ORF, (e.g., the first 3, 6, 9, 12, 15, 18, 21, 24, or more nucleotides of the ORF of Bmi-1); and (ii) a carboxy terminal fragment of the Bmi-1 ORF (e.g., the last 3, 6, 9, 12, 15, 18, 21, 24, or more nucleotides of the ORF of Bmi-1) and the 3'-UTR of Bmi-1 or a fragment, mutant or post-transcriptional regulatory element thereof, wherein the reporter gene is in frame with the amino terminal and carboxy terminal fragments of the ORF of Bmi-1 and the reporter gene lacks an endogenous stop codon, and wherein the 5'-UTR of Bmi-1 or a fragment, mutant or post-transcriptional regulatory element thereof and the amino terminal fragment of the Bmi-1 ORF are upstream of the reporter gene, and the 3'-UTR or fragment, mutant or post-transcriptional regulatory element thereof and the carboxy terminal fragment of the ORF of Bmi-1 are downstream of the reporter gene; and (b) detecting the amount or activity of a reporter protein translated from a mRNA transcript transcribed from said reporter gene, wherein a compound that modulates UTR-dependent expression of Bmi-1 is identified or validated if the amount or activity of said reporter protein detected in the presence of the compound is altered relative to a previously determined reference range, or relative to the amount or activity of said reporter protein detected in the absence of said compound or the presence of a negative control. In one embodiment, a compound that down-regulates UTR-dependent expression of Bmi-1 is identified or validated if the amount or activity of said reporter protein detected in the presence of the compound is down-regulated or reduced relative to a previously determined reference range, or relative to the amount or activity of said reporter protein detected in the absence of said compound or the presence of a negative control. In certain embodiments, the reporter gene lacks an endogenous start codon. In specific embodiments, the nucleic acid construct comprises the 5'-UTR of human Bmi-1 and the first 21 nucleotides of the ORF from the 5' end of human Bmi-1. In another specific embodiment, the nucleic acid construct comprises nucleic acid residues 1 to 505 of the 5'-UTR of human Bmi-1 and the first 21 nucleotides of the ORF from the 5' end of human Bmi-1. In other specific embodiments, the nucleic acid construct comprises the last 21 nucleotides of the ORF from the 3' end of human Bmi-1 and the 3'-UTR of Bmi-1 or a fragment, mutant or post-transcriptional regulatory element thereof.

In another embodiment, the methods described herein provide for identifying or validating a compound that modulates IRES-dependent translation activity of Bmi-1 while leaving CAP-dependent translation activity of Bmi-1 unaffected using bicistronic nucleic acid constructs containing the IRES of the 5'-UTR of Bmi-1. In this embodiment, the method includes (a) contacting a compound with a host cell containing a bicistronic nucleic acid construct expressing a first reporter protein and a second reporter protein, wherein said bicistronic nucleic acid construct comprises, in the following 5' to 3' order, a cap, a promoter, a first reporter gene encoding or coding for a first reporter protein mRNA transcript, a 5'-UTR of Bmi-1 or a fragment thereof comprising the IRES sequence of the 5'-UTR of Bmi-1, and a second reporter gene encoding or coding for a second reporter protein mRNA transcript, and wherein the translation of the first reporter protein mRNA transcript encoded by the first reporter gene is CAP-dependent/initiated and the translation of the second reporter protein mRNA transcript encoded by the second reporter gene is IRES-dependent/initiated; and (b) detecting the amount or activity of the first and second reporter proteins, wherein a compound that modulates IRES-dependent translation activity of Bmi-1 while leaving CAP-dependent translation activity of Bmi-1 unaffected is identified or validated if: (i) the amount or activity of the first reporter protein detected in the presence of the compound is not altered or not significantly altered relative to the amount or activity of the first reporter protein by the detected in the absence of the compound or the presence of a negative control, or relative to a previously determined reference range, and (ii) the amount or activity of the second reporter protein detected in the presence of the compound is significantly altered relative to the amount or activity of the second reporter protein detected in the absence of the compound or the presence of a negative control, or relative to a previously determined reference range. In a specific embodiment, the previously determined reference range is the amount or activity of the reporter protein detected in the presence of a negative control (e.g., PBS or DMSO).

In another embodiment, the methods described herein provide for identifying or validating a compound that decreases or down-regulates IRES-dependent translation activity of Bmi-1 while leaving CAP-dependent translation activity of Bmi-1 unaffected, said method comprising: (a) contacting a compound with a host cell containing a bicistronic nucleic acid construct expressing a first reporter protein and a second reporter protein, wherein said bicistronic nucleic acid construct comprises, in the following 5' to 3' order, a cap, a promoter, a first reporter gene encoding or coding for a first reporter protein mRNA transcript, a 5'-UTR of Bmi-1 or a fragment thereof comprising the IRES sequence of the 5'-UTR of Bmi-1, and a second reporter gene encoding or coding for a second reporter protein mRNA transcript, and wherein the translation of the first reporter protein mRNA transcript encoded by the first reporter gene is CAP-dependent/initiated and the translation of the second reporter protein mRNA transcript encoded by the second reporter gene is IRES-dependent/initiated; and (b) detecting the amount or activity of the first and second reporter proteins, wherein a compound that decreases or down-regulates IRES-dependent translation activity of Bmi-1 while leaving CAP-dependent translation activity of Bmi-1 unaffected is identified or validated if: (i) the amount or activity of the first reporter protein detected in the presence of the compound is not altered or not significantly altered relative to the amount or activity of the first reporter protein by the detected in the absence of the compound or the presence of a negative control, or relative to a previously determined reference range, and (ii) the amount or activity of the second reporter protein detected in the presence of the compound is significantly decreased or down-regulated relative to the amount or activity of the second reporter protein detected in the absence of the compound or the presence of a negative control, or relative to a previously determined reference range. In an embodiment, the ratio of the amount or activity of the first reporter protein over the amount of the second reporter protein increases if a compound affects the IRES. In a specific embodiment, the previously determined reference range is the amount or activity of the reporter protein detected in the presence of a negative control (e.g., PBS or DMSO).

In some embodiments, the methods described herein provide for identifying or validating a compound that modulates IRES-dependent translation activity of Bmi-1 while leaving CAP-dependent translation activity of Bmi-1 unaffected, said method comprising: (a) contacting a compound with a host cell containing a bicistronic nucleic acid construct expressing a first reporter protein and a second reporter protein, wherein said bicistronic nucleic acid construct comprises, in the following 5' to 3' order, a cap, a promoter, a first reporter gene encoding or coding for a first reporter protein mRNA transcript, a 5'-UTR of Bmi-1 or a fragment thereof comprising the IRES sequence of the 5'-UTR of Bmi-1, an amino terminal fragment of the Bmi-1 ORF, (e.g., the first 3, 6, 9, 12, 15, 18, 21, 24, or more nucleotides of the ORF of Bmi-1), and a second reporter gene encoding or coding for a second reporter protein mRNA transcript, wherein the amino terminal fragment is in frame with the second reporter gene, and wherein the translation of the first reporter protein mRNA transcript encoded by the first reporter gene is CAP-dependent/initiated and the translation of the second reporter protein mRNA transcript encoded by the second reporter gene is IRES-dependent/initiated; and (b) detecting the amount or activity of the first and second reporter proteins, wherein a compound that modulates IRES-dependent translation activity of Bmi-1 while leaving CAP-dependent translation activity of Bmi-1 unaffected is identified or validated if: (i) the amount or activity of the first reporter protein detected in the presence of the compound is not altered or not significantly altered relative to the amount or activity of the first reporter protein detected in the absence of the compound or the presence of a negative control, or relative to a previously determined reference range, and (ii) the amount or activity of the second reporter protein detected in the presence of the compound is significantly altered relative to the amount or activity of the second reporter protein detected in the absence of the compound or the presence of a negative control, or relative to a previously determined reference range. In a specific embodiment, the previously determined reference range is the amount or activity of the reporter protein detected in the presence of a negative control (e.g., PBS or DMSO). In certain embodiments, the reporter gene lacks an endogenous start codon. In specific embodiments, the nucleic acid construct comprises the 5'-UTR of human Bmi-1 and the first 21 nucleotides of the ORF from the 5' end of human Bmi-1. In another specific embodiment, the nucleic acid construct comprises nucleic acid residues 1 to 505 of the 5'-UTR of human Bmi-1 and the first 21 nucleotides of the ORF from the 5' end of human Bmi-1.

The cell-based screening methods described herein include identifying environmental stimuli (e.g., exposure to different concentrations of $CO_2$ and/or $O_2$, stress and different pHs) that modulate UTR-dependent expression of Bmi-1. In particular, the method described herein for identifying an environmental stimulus comprises: (a) contacting a host cell expressing a reporter protein via a nucleic acid comprising a reporter gene encoding or coding for said reporter protein operably linked to any of the 5'-UTR and 3'-UTR, or the 5'-UTR or the 3'-UTR of Bmi-1, or a fragment, mutant or post-transcriptional regulatory element thereof with an environmental stimulus, wherein the 5'-UTR of Bmi-1 or fragment, mutant or post-transcriptional regulatory element thereof is upstream of the reporter gene and the 3'-UTR of Bmi-1 or fragment, mutant or post-transcriptional regulatory element thereof is downstream of the reporter gene; and (b) detecting the amount or activity of said reporter protein, wherein a compound that modulates UTR-dependent expression of Bmi-1 is identified if the amount or activity of said reporter protein detected in the presence of an environmental stimuli is altered relative to a previously determined reference range, or relative to the amount or activity of said reporter protein detected in the absence of the compound or the presence of a negative control (e.g., PBS or DMSO). In a specific embodiment, the environmental stimuli does not include a compound.

The expression of a reporter protein in the cell-based reporter-gene screening methods may be detected by any technique well-known to one of skill in the art. Methods for detecting the expression of a reporter protein will vary with the reporter gene used. Assays for the various reporter genes are well-known to one of skill in the art. For example, as described herein, luciferase, beta-galactosidase ("β-gal"), beta-glucoronidase ("GUS"), beta-lactamase, chloramphenicol acetyltransferase ("CAT"), and alkaline phosphatase ("AP") are enzymes that can be analyzed in the presence of a substrate and could be amenable to high throughput screening. For example, the reaction products of luciferase, beta-galactosidase ("β-gal"), and alkaline phosphatase ("AP") are assayed by changes in light imaging (e.g., luciferase), spectrophotometric absorbance (e.g., b-gal), or fluorescence (e.g., AP). Assays for changes in light output, absorbance, and/or fluorescence are easily adapted for high throughput screening. For example, b-gal activity can be measured with a microplate reader. Green fluorescent protein ("GFP") activity can be measured by changes in fluorescence. For example, in the case of mutant GFPs that fluoresce at 488 nm, standard fluorescence activated cell sorting ("FACS") equipment can be used to separate cells based upon GFP activity.

Alterations in the expression of a reporter protein may be determined by comparing the amount or activity of the reporter protein to a negative control (e.g., PBS, DMSO or another agent that is known to have no effect on the expression of the reporter gene) and optionally, a positive control (e.g., an agent that is known to have an effect on the expression of the reporter gene, preferably an agent that effects untranslated region-dependent expression). Alternatively, alterations in the expression of a reporter protein may be determined by comparing the amount or activity of the reporter protein to a previously determined reference range.

Cell-Free Screening Methods

A cell-free extract and a nucleic acid construct described herein may be used to screen, identify or validate compounds that modulate UTR-dependent expression of Bmi-1. The methods described herein include a method for identifying or validating a compound that modulates UTR-dependent expression of Bmi-1 comprises (a) contacting a compound with a cell free extract and the nucleic acid construct described herein comprising a reporter gene; and (b) detecting the amount or activity of a reporter protein translated from said reporter gene, wherein a compound that modulates UTR-dependent expression of Bmi-1 is identified or validated if the amount or activity of said reporter protein detected in the presence of the compound is altered relative to a previously determined reference range, or relative to the amount or activity of said reporter protein detected in the absence of the compound or the presence of a negative control (e.g., PBS or DMSO).

In one embodiment, the screening methods to identify or validate a compound that modulates UTR-dependent expression of Bmi-1 may be conducted in a cell-free manner by contacting a compound with a cell-free extract and a nucleic acid construct comprising a reporter gene operably linked to any of the 5'-UTR and 3'-UTR, or the 5'-UTR or the 3'-UTR of Bmi-1, or a fragment, mutant or post-transcriptional regulatory element of each thereof, wherein the 5'-UTR of Bmi-1 or fragment, mutant or post-transcriptional regulatory element thereof is upstream of the reporter gene and the 3'-UTR of Bmi-1 or fragment, mutant or post-transcriptional regulatory element thereof is downstream of the reporter gene, and measuring the amount or activity of the reporter protein translated from the reporter gene. The alteration in the amount or activity of the reporter protein detected in the presence of the compound relative to a previously determined reference range, or relative to the amount or activity or a reporter protein detected in the absence of a compound or the presence of a negative control indicates that a particular compound modulates UTR-dependent expression of Bmi-1. In one embodiment, a negative control (e.g., PBS, DMSO or another agent that is known to have no effect on the expression of the reporter gene) and a positive control (e.g., an agent that is known to have an effect on the expression of the reporter gene, preferably an agent that affects UTR-dependent expression) are included in the cell-free screening methods described herein. In a specific embodiment, the previously determined reference range is the amount or activity of said reporter protein in the presence of a negative control (e.g., PBS or DMSO).

Typically, the nucleic acid construct used in the cell-free screening method is a RNA transcript (e.g., mRNA or pre-mRNA) that has been produced using, e.g., in vitro run-off transcription. For example, a RNA can be made in run-off transcription of a linearized form of a nucleic acid construct that is DNA which contains a bacteriophage promoter, a reporter gene and any of the 5'-UTR and 3'-UTR, or the 5'-UTR or the 3'-UTR of Bmi-1, wherein the 5'-UTR is upstream and the 3'-UTR is downstream, and wherein the bacteriophage promoter drives transcription of said reporter gene. Bacteriophage promoters from a T3, SP6 or T7 bacteriophage or any other suitable promoter may be used together with the respective RNA polymerase derived from the corresponding bacteriophage. The methods described herein also provide nucleic acid constructs that may be prepared by in vitro run-off transcription.

The step of contacting a compound with a cell-free extract and a nucleic acid construct comprising a reporter gene encoding or coding for said reporter protein operably linked to any of the 5'-UTR and 3'-UTR, or the 5'-UTR or the 3'-UTR of Bmi-1, or a fragment, mutant or post-transcriptional regulatory element thereof may be conducted under conditions approximating or mimicking physiologic conditions. In a specific embodiment, a compound described herein is added to the cell-free extract in the presence of an aqueous solution. In accordance with this embodiment, the aqueous solution may comprise a buffer and a combination of salts, preferably approximating or mimicking physiologic conditions. Alternatively, the aqueous solution may comprise a buffer, a combination of salts, and a detergent or a surfactant. Examples of salts which may be used in the aqueous solution include, but not limited to, KCl, NaCl, and/or $MgCl_2$. The optimal concentration of each salt used in the aqueous solution is dependent on the cell-free extract and compounds used and can be determined using routine experimentation.

The methods described herein provide a method for contacting a compound with a cell-free extract and a nucleic acid construct comprising a reporter gene encoding or coding for said reporter protein operably linked to any of the 5'-UTR and 3'-UTR, or the 5'-UTR or the 3'-UTR of Bmi-1, or a fragment, mutant or post-transcriptional regulatory element of each thereof for a specific period of time. For example, the contacting can take place for about 1 minute, 2 minutes, 3 minutes, 4, minutes, 5, minutes, 10 minutes, 15 minutes, 20 minutes, 30 minutes, 1 hour, 2 hours, 3 hours, 4 hours, 5 hours, 10 hours, 15 hours, 20 hours, 1 day, 2 days, 3 days, 4 days, 5 days, or 1 week. In one embodiment, the contacting is about 15 hours, i.e., overnight. The contacting can take place for about 1 minute to 1 week, preferably about 5 minutes to 5 days, more preferably about 10 minutes to 2 days, and even more preferably about 1 hour to 1 day.

In a specific embodiment, the methods described herein provide for identifying or validating a compound that modulates untranslated region-dependent expression of Bmi-1, said method comprising: (a) contacting a compound with a cell-free extract and a nucleic acid construct comprising a reporter gene operably linked to any of the 5'-UTR and 3'-UTR, or the 5'-UTR or the 3'-UTR of Bmi-1, or a fragment, mutant or post-transcriptional regulatory element of each thereof, wherein the 5'-UTR of Bmi-1 or fragment, mutant or post-transcriptional regulatory element thereof is upstream of the reporter gene and the 3'-UTR of Bmi-1 or fragment, mutant or post-transcriptional regulatory element thereof is downstream of the reporter gene; and (b) detecting the amount or activity of a reporter protein translated from said reporter gene, wherein a compound that modulates UTR-dependent expression of Bmi-1 is identified or validated if the amount or activity of said reporter protein detected in the presence of the compound is altered relative to a previously determined reference range, or relative to the amount or activity of said reporter protein detected in the absence of the compound or the presence of a negative control (e.g., PBS or DMSO).

In a specific embodiment, the methods described herein provide a method of decreasing or down-regulating UTR-dependent expression of Bmi-1, said method comprising (a) contacting a compound with a cell-free extract and a nucleic acid construct comprising a reporter gene operably linked to any of the 5'-UTR and 3'-UTR, or the 5'-UTR or the 3'-UTR of Bmi-1, or a fragment, mutant or post-transcriptional regulatory element of each thereof, wherein the 5'-UTR of Bmi-1 or fragment, mutant or post-transcriptional regulatory element thereof is upstream of the reporter gene and the 3'-UTR of Bmi-1 or fragment, mutant or post-transcriptional regulatory element thereof is downstream of the reporter gene; and (b) detecting the amount or activity of a reporter protein translated from said reporter gene, wherein a compound that decreases or down-regulates UTR-dependent expression of Bmi-1 is identified or validated if the amount or activity of said reporter protein detected in the presence of the compound is decreased relative to a previously determined reference range, or relative to the amount or activity of said reporter protein detected in the absence of the compound or the presence of a negative control (e.g., PBS or DMSO). In one embodiment, the nucleic acid construct is RNA. In a specific embodiment, the previously determined reference range is the amount or activity of said reporter protein in the presence of a negative control (e.g., PBS or DMSO).

In a specific embodiment, the methods described herein provide a method for identifying or validating compounds that modulates UTR-dependent expression of Bmi-1, said method comprising (a) contacting a compound with a cell-free extract and a RNA (e.g., a mRNA) comprising a reporter gene operably linked to any of the 5'-UTR and 3'-UTR, or the 5'-UTR or the 3'-UTR of Bmi-1 mRNA, or a fragment, mutant or post-transcriptional regulatory element of each thereof, wherein the 5'-UTR of Bmi-1 or fragment, mutant or post-transcriptional regulatory element thereof is upstream of the reporter gene and the 3'-UTR of Bmi-1 or fragment, mutant or post-transcriptional regulatory element thereof is downstream of the reporter gene; and (b) detecting the amount or activity of a reporter protein translated from said reporter gene, wherein a compound that modulates UTR-dependent expression of Bmi-1 is identified or validated if the amount or activity of said reporter protein detected in the presence of the compound is altered relative to a previously determined reference range, or relative to the amount or activity of said reporter protein detected in the absence of the compound or the presence of a negative control (e.g., PBS or DMSO).

In a specific embodiment, the methods described herein provide a method for identifying or validating compounds that decrease or down-regulate UTR-dependent expression of Bmi-1, said method comprising (a) contacting a compound with a cell-free extract and a RNA (e.g., a mRNA) comprising a reporter gene operably linked to any of the 5'-UTR and 3'-UTR, or the 5'-UTR or the 3'-UTR of Bmi-1 mRNA, or a fragment, mutant or post-transcriptional regulatory element of each thereof, wherein the 5'-UTR or fragment, mutant or post-transcriptional regulatory element thereof is upstream of the reporter gene and the 3'-UTR of Bmi-1 or fragment, mutant or post-transcriptional regulatory element thereof is downstream of the reporter gene; and (b) detecting the amount or activity of a reporter protein translated from said reporter gene, wherein a compound that decreases or down-regulates UTR-dependent expression of Bmi-1 is identified or validated if the amount or activity of said reporter protein detected in the presence of the compound is decreased relative to a previously determined reference range, or relative to the amount or activity of said reporter protein detected in the absence of the compound or the presence of a negative control (e.g., PBS or DMSO).

In some embodiments, the methods described herein relate to a method for identifying or validating a compound that modulates UTR dependent expression of Bmi-1 comprising the steps of: (a) contacting a compound with a cell-free extract and a nucleic acid construct comprising a reporter gene operably linked to the 5'-UTR of Bmi-1 or a fragment, mutant or post-transcriptional regulatory element thereof and an amino terminal fragment of the Bmi-1 ORF, (e.g., the first 3, 6, 9, 12, 15, 18, 21, 24, or more nucleotides of the ORF of Bmi-1), wherein the reporter gene is in frame with the amino terminal fragment of the ORF of Bmi-1, and wherein the 5'-UTR of Bmi-1 or a fragment, mutant or post-transcriptional regulatory element thereof and the amino terminal fragment of the Bmi-1 ORF are upstream of the reporter gene; and (b) detecting the amount or activity of a reporter protein translated from said reporter gene, wherein a compound that modulates UTR-dependent expression of Bmi-1 is identified or validated if the amount or activity of said reporter protein detected in the presence of the compound is altered relative to a previously determined reference range or relative to the amount or activity of said reporter protein detected in the absence of said compound or the presence of a negative control. In one embodiment, a compound that down-regulates UTR-dependent expression of Bmi-1 is identified or validated if the amount or activity of said reporter protein detected in the presence of the compound is down-regulated or reduced relative to a previously determined reference range, or relative to the amount or activity of said reporter protein detected in the absence of said compound or the presence of a negative control. In certain embodiments, the reporter gene lacks an endogenous start codon. In specific embodiments, the nucleic acid construct comprises the 5'-UTR of human Bmi-1 and the first 21 nucleotides of the ORF from the 5' end of human Bmi-1. In another specific embodiment, the nucleic acid construct comprises nucleic acid residues 1 to 505 of the 5'-UTR of human Bmi-1 and the first 21 nucleotides of the ORF from the 5' end of human Bmi-1.

In some embodiments, the methods described herein relate to a method for identifying or validating a compound that modulates UTR dependent expression of Bmi-1 comprising the steps of: (a) contacting a compound with a cell-free extract and a nucleic acid construct comprising a reporter gene operably linked to a carboxy terminal fragment of the Bmi-1 ORF (e.g., the last 3, 6, 9, 12, 15, 18, 21, 24, or more nucleotides of the ORF of Bmi-1) and the 3'-UTR of Bmi-1 or a fragment, mutant or post-transcriptional regulatory element thereof, wherein the reporter gene is in frame with the carboxy terminal fragment of the Bmi-1 ORF and the reporter gene lacks an endogenous stop codon, and wherein the carboxy terminal fragment of the ORF of Bmi-1 and the 3'-UTR of Bmi-1 or a fragment, mutant or post-transcriptional regulatory element thereof are downstream of the reporter gene; and (b) detecting the amount or activity of a reporter protein translated from said reporter gene, wherein a compound that modulates UTR-dependent expression of Bmi-1 is identified or validated if the amount or activity of said reporter protein detected in the presence of the compound is altered relative to a previously determined reference range or relative to the amount or activity of said reporter protein detected in the absence of said compound or the presence of a negative control. In one embodiment, a compound that down-regulates UTR-dependent expression of Bmi-1 is identified or validated if the amount or activity of said reporter protein detected in the presence of the compound is down-regulated or reduced relative to a previously determined reference range, or relative to the amount or activity of said reporter protein detected in the absence of said compound or the presence of a negative control.

In some embodiments, the methods described herein relate to a method for identifying or validating a compound that modulates UTR dependent expression of Bmi-1 comprising the steps of: (a) contacting a compound with a cell-free extract and a nucleic acid construct comprising a reporter gene operably linked to (i) the 5'-UTR of Bmi-1 or a fragment, mutant or post-transcriptional regulatory element thereof and an amino terminal fragment of the Bmi-1 ORF, (e.g., the first 3, 6, 9, 12, 15, 18, 21, 24, or more nucleotides of the ORF of Bmi-1); and (ii) a carboxy terminal fragment of the Bmi-1 ORF (e.g., the last 3, 6, 9, 12, 15, 18, 21, 24, or more nucleotides of the ORF of Bmi-1) and the 3'-UTR of Bmi-1 or a fragment, mutant or post-transcriptional regulatory element thereof, wherein the reporter gene is in frame with the amino terminal and carboxy terminal fragments of the ORF of Bmi-1 and the reporter gene lacks an endogenous stop codon, and wherein the 5'-UTR of Bmi-1 or a fragment, mutant or post-transcriptional regulatory element thereof and the amino terminal fragment of the Bmi-1 ORF are upstream of the reporter gene, and the carboxy terminal fragment of the ORF of Bmi-1 and the 3'-UTR or fragment, mutant or post-transcriptional regulatory element thereof are downstream of the reporter gene; and (b) detecting the amount or activity of a reporter protein translated from said reporter gene, wherein a compound that modulates UTR-dependent expression of Bmi-1 is identified or validated if the amount or activity of said reporter protein detected in the presence of the compound is altered relative to a previously determined reference range or relative to the amount or activity of said reporter protein detected in the absence of said compound or the presence of a negative control. In one embodiment, a compound that down-regulates UTR-dependent expression of Bmi-1 is identified or validated if the amount or activity of said reporter protein detected in the presence of the compound is down-regulated or reduced relative to a previously determined reference range, or relative to the amount or activity of said reporter protein detected in the absence of said compound or the presence of a negative control. In certain embodiments, the reporter gene lacks an endogenous start codon. In specific embodiments, the nucleic acid construct comprises the 5'-UTR of human Bmi-1 and the first 21 nucleotides of the ORF from the 5' end of human Bmi-1. In another specific embodiment, the nucleic acid construct comprises nucleic acid residues 1 to 505 of the 5'-UTR of human Bmi-1 and the first 21 nucleotides of the ORF from the 5' end of human Bmi-1. In other specific embodiments, the nucleic acid construct comprises the last 21 nucleotides of the ORF from the 3' end of human Bmi-1 and the 3'-UTR of Bmi-1 or a fragment, mutant or post-transcriptional regulatory element thereof.

In a specific embodiment, the method described herein provides a method for identifying or validating a compound that modulates IRES-dependent translation activity of Bmi-1 while leaving CAP-dependent translation activity of Bmi-1 unaffected, said method comprising: (a) contacting a compound with a cell-free extract and a bicistronic nucleic acid construct expressing a first reporter protein and a second reporter protein, wherein said bicistronic nucleic acid construct comprises, in the following 5' to 3' order, a cap, a promoter, a first reporter gene encoding or coding for a first reporter protein mRNA transcript, a 5'-UTR of Bmi-1 or a fragment thereof comprising the IRES sequence of the 5'-UTR of Bmi-1, and a second reporter gene encoding or coding for a second reporter protein mRNA transcript, and wherein the translation of the first reporter protein mRNA transcript encoded by the first reporter gene is CAP-dependent/initiated and the translation of the second reporter protein mRNA transcript encoded by the second reporter gene is IRES-dependent/initiated; and (b) detecting the amount or activity of the first and second reporter proteins translated from the first and second reporter genes, respectively, wherein a compound that modulates IRES-dependent translation activity of Bmi-1 while leaving CAP-dependent translation activity of Bmi-1 unaffected is identified or validated if: (i) the amount or activity of the first reporter protein detected in the presence of the compound is not altered or not significantly altered relative to the amount or activity of the first reporter protein detected in the absence of the compound or the presence of a negative control, or relative to a previously determined reference range, and (ii) the amount or activity of the second reporter protein detected in the presence of the compound is significantly altered relative to the amount or activity of the second reporter protein detected in the absence of the compound or the presence of a negative control, or relative to a previously determined reference range. In a specific embodiment, the previously determined reference range is the amount or activity of the reporter protein detected in the presence of a negative control (e.g., PBS or DMSO).

In another embodiment, the method described herein provides a method for identifying or validating a compound that decreases or down-regulates IRES-dependent translation activity of Bmi-1 while leaving CAP-dependent translation activity of Bmi-1 unaffected, said method comprising: (a) contacting a compound with a cell-free extract and a bicistronic nucleic acid construct expressing a first reporter protein and a second reporter protein, wherein said bicistronic nucleic acid construct comprises, in the following 5' to 3' order, a cap, a promoter, a first reporter gene encoding or coding for a first reporter protein mRNA transcript, a 5'-UTR of Bmi-1 or a fragment thereof comprising the IRES sequence of the 5'-UTR of Bmi-1, and a second reporter gene encoding or coding for a second reporter protein mRNA transcript, and wherein the translation of the first reporter protein mRNA transcript encoded by the first reporter gene is CAP-dependent/initiated and the translation of the second reporter protein mRNA transcript encoded by the second reporter gene is IRES-dependent/initiated; and (b) detecting the amount or activity of the first and second reporter proteins translated from the first and second reporter genes, respectively, wherein a compound that decreases or down-regulates IRES-dependent translation activity of Bmi-1 while leaving CAP-dependent translation activity of Bmi-1 unaffected is identified or validated if: (i) the amount or activity of the first reporter protein detected in the presence of the compound is not altered or not significantly altered relative to the amount or activity of the first reporter protein detected in the absence of the compound or the presence of a negative control, or relative to a previously determined reference range, and (ii) the amount or activity of the second reporter protein detected in the presence of the compound is significantly altered relative to the amount or activity of the second reporter protein detected in the absence of the compound or the presence of a negative control, or relative to a previously determined reference range. In an embodiment, the ratio of the amount or activity of the first reporter protein over the amount of the second reporter protein increases if a compound affects the IRES. In a specific embodiment, the previously determined reference range is the amount or activity of the reporter protein detected in the presence of a negative control (e.g., PBS or DMSO).

In some embodiments, the methods described herein relate to a method for identifying or validating a compound that modulates IRES-dependent translation activity of Bmi-1 while leaving CAP-dependent translation activity of Bmi-1 unaffected, said method comprising: (a) contacting a compound with a cell-free extract and a bicistronic nucleic acid construct expressing a first reporter protein and a second reporter protein, wherein said bicistronic nucleic acid construct comprises, in the following 5' to 3' order, a cap, a promoter, a first reporter gene encoding or coding for a first reporter protein mRNA transcript, a 5'-UTR of Bmi-1 or a fragment thereof comprising the IRES sequence of the 5'-UTR of Bmi-1, an amino terminal fragment of the Bmi-1 ORF, (e.g., the first 3, 6, 9, 12, 15, 18, 21, 24, or more nucleotides of the ORF of Bmi-1), and a second reporter gene encoding or coding for a second reporter protein mRNA transcript, wherein the amino terminal fragment of the Bmi-1 ORF is in frame with the second reporter gene, and wherein the translation of the first reporter protein mRNA transcript encoded by the first reporter gene is CAP-dependent/initiated and the translation of the second reporter protein mRNA transcript encoded by the second reporter gene is IRES-dependent/initiated; and (b) detecting the amount or activity of the first and second reporter proteins translated from the first and second reporter genes, respectively, wherein a compound that modulates IRES-dependent translation activity of Bmi-1 while leaving CAP-dependent translation activity of Bmi-1 unaffected is identified or validated if: (i) the amount or activity of the first reporter protein detected in the presence of the compound is not altered or not significantly altered relative to the amount or activity of the first reporter protein detected in the absence of the compound or the presence of a negative control, or relative to a previously determined reference range, and (ii) the amount or activity of the second reporter protein detected in the presence of the compound is significantly altered relative to the amount or activity of the second reporter protein detected in the absence of the compound or the presence of a negative control, or relative to a previously determined reference range. In a specific embodiment, the previously determined reference range is the amount or activity of the reporter protein detected in the presence of a negative control (e.g., PBS or DMSO). In certain embodiments, the reporter gene lacks an endogenous start codon. In specific embodiments, the nucleic acid construct comprises the 5'-UTR of human Bmi-1 and the first 21 nucleotides of the ORF from the 5' end of human Bmi-1. In another specific embodiment, the nucleic acid construct comprises nucleic acid residues 1 to 505 of the 5'-UTR of human Bmi-1 and the first 21 nucleotides of the ORF from the 5' end of human Bmi-1.

The activity of a compound in the in vitro extract can be determined by assaying the amount or activity of a reporter protein translated from a reporter gene, or alternatively, by quantifying the expression of the reporter gene by, for example, labeling the in vitro translated protein (e.g., with $^{35}$S-labeled methionine), or by immunological methods, such as western blot analysis or immunoprecipitation. Such methods are well-known to one of skill in the art.

Direct Binding Assays

A subset of compounds that modulate UTR-dependent expression of Bmi-1 can be identified by direct binding assays, such as those known to one of skill in the art. Briefly, direct binding assays may be conducted by attaching one or more compounds to solid supports, e.g., polymer beads, with each solid support having substantially one type of compound attached to its surface. The plurality of the solid support is exposed in aqueous solution to a target RNA having a detectable label, forming a dye-labeled target RNA:support-attached compound complex, wherein the target RNA is Bmi-1 RNA transcript or RNA transcript comprising any of the 5'-UTR and 3'-UTR, or the 5'-UTR or the 3'-UTR of Bmi-1 mRNA, or a fragment, mutant or post-transcriptional regulatory element of each thereof. Binding of a target RNA molecule to a particular compound labels the solid support, e.g., bead, comprising the compound, which can be physically separated from other, unlabeled solid supports. Alternatively, the compound and not the target RNA is labeled, and the target RNA is attached to a solid support.

Direct binding screening methods may be conducted by contacting a target RNA having a detectable label with a compound free in solution, in labeled tubes or microtiter wells, or a microarray wherein the target RNA is selected from a Bmi-1 mRNA transcript or RNA transcript comprising any of the 5'-UTR and 3'-UTR, or the 5'-UTR or the 3'-UTR of Bmi-1, or a fragment, mutant or post-transcriptional regulatory element of each thereof. Alternatively, the compound and not the target RNA is labeled.

Binding assays, including direct binding screening methods, can also be used to detect the interaction between compounds and proteins that regulate the post-transcriptional expression of Bmi-1. Briefly, direct binding assays may be conducted by attaching one or more compounds to a solid support, e.g., polymer beads, with each solid support having substantially one type of compound attached to its surface. The plurality of solid supports is exposed in aqueous solution to a target protein having a detectable label, forming a dye-labeled target protein:support-attached compound complex, wherein the target protein is a protein that modulates UTR-mediated expression of Bmi-1. Alternatively, the compound is labeled and the target protein is attached to a solid support. Similar to the screening methods described above with respect to RNA, the interaction between a target protein and a compound can be conducted in solution.

Identification and Validation of Compounds

Using embodiments of the screening methods described herein, Applicants have identified or validated compounds for their effect on UTR-dependent expression of Bmi-1. Further, any compound of interest can be tested for its ability to modulate UTR-dependent expression of Bmi-1 using the screening methods described herein.

In one embodiment, a compound that modulates UTR-dependent expression of Bmi-1 binds directly to any of the 5'-UTR and 3'-UTR, or the 5'-UTR or the 3'-UTR of Bmi-1, or a fragment, mutant or post-transcriptional regulatory element of each thereof. In another embodiment, a compound that modulates UTR-dependent expression of Bmi-1, does not bind directly to any of the 5'-UTR and 3'-UTR, or the 5'-UTR or the 3'-UTR of Bmi-1, or a fragment, mutant or post-transcriptional regulatory element of each thereof. In another embodiment, a compound that modulates UTR-dependent expression of Bmi-1 binds to a protein that modulates UTR-dependent expression of Bmi-1. In yet another embodiment, a compound that modulates UTR-dependent expression of Bmi-1 binds to a nucleotide regulatory sequence of a gene that encodes a protein that modulates UTR-dependent expression of Bmi-1.

In a specific embodiment, a compound is an antisense oligonucleotide, which is a nucleotide sequence complementary to a specific DNA or RNA sequence described herein. Antisense oligonucleotides can be deoxyribonucleotides, ribonucleotides, or a combination of both. Nucleic acid molecules including antisense oligonucleotide molecules, can be provided in a DNA construct and introduced into a cell. In another embodiment, a compound is an interfering RNA (RNAi) or microRNA (miRNA). RNAi comprises dsRNA that inhibits the expression of genes with complementary nucleotide sequences. In one embodiment, the dsRNA is 20-25 residues in length, termed small interfering RNAs (siRNA).

In order to exclude the possibility that a particular compound is functioning solely by modulating the expression of Bmi-1 in a UTR-independent manner, one or more mutations may be introduced into an untranslated region(s) operably linked to a reporter gene and the effect on the expression of the reporter gene in a screening method as described herein can be determined. For example, a nucleic acid construct comprising the 5'-UTR of Bmi-1 may be mutated by deleting a fragment of the 5'-UTR of Bmi-1 or substituting a fragment of the 5'-UTR of Bmi-1 with a fragment of the 5'-UTR of another gene and measuring the expression of the reporter gene in the presence and absence of a compound that has been identified or validated in an instant screening method as described herein. If the deletion of a fragment of the 5'-UTR of Bmi-1 or the substitution of a fragment of the 5'-UTR of Bmi-1 with a fragment of the 5'-UTR of another gene affects the ability of the compound to modulate the expression of the reporter gene, then the fragment of the 5'-UTR that is deleted or substituted plays a role in the regulation of the reporter gene expression and the regulation, at least in part, is in an UTR-dependent manner.

The possibility that a particular compound functions solely by modulating the expression of Bmi-1 in an UTR-independent manner may be also determined by changing the vector utilized as a nucleic acid construct. The UTRs flanked by a reporter gene from the nucleic acid construct in which an effect on reporter gene expression was detected following exposure to a compound may be inserted into a new nucleic acid construct that has, e.g., different transcriptional regulation elements (e.g., a different promoter) and a different selectable marker. The level of reporter gene expression in the presence of a compound described herein can be compared to the level of reporter gene expression in the absence of the compound or in the presence of a control (e.g., PBS or DMSO). If there is no change in the level of expression of the reporter gene in the presence of the compound relative to the absence of the compound or in the presence of a control, then the compound described herein may be functioning in an UTR-independent manner.

The specificity of a particular compound's effect on UTR-dependent expression of Bmi-1 can also be determined. In particular, the effect of a particular compound on the expression of one or more genes (preferably, a plurality of genes) can be determined utilizing methods well known to one of skill in the art or described herein. In one embodiment, the specificity of a particular compound for an untranslated region of Bmi-1 mRNA is determined by (a) contacting the compound of interest with a host cell expressing a reporter protein via a nucleic acid construct comprising a reporter gene encoding said reporter protein operably linked to an UTR of a different gene (i.e., a gene different from Bmi-1 which has an UTR different from said Bmi-1); and (b) detecting the amount or activity of said reporter protein, wherein the compound is specific for the untranslated region of Bmi-1 mRNA if the amount or activity of said reporter protein detected in the presence of the compound is not altered or is not substantially altered relative to a previously determined reference range, or relative to the amount or activity of said reporter protein detected in the absence of the compound or the presence of a negative control (e.g., PBS or DMSO).

In another embodiment, the specificity of a particular compound for an UTR of Bmi-1 mRNA is determined by (a) contacting the compound of interest with a panel of host cells, each host cell in a different well of a container (e.g., a 48- or 96-well plate) and each host cell expressing a reporter protein via a nucleic acid construct comprising a reporter gene operably linked to an UTR of a different gene which has an UTR different from Bmi-1; and (b) detecting the amount or activity of a reporter protein, wherein the compound is specific for the untranslated region of Bmi-1 mRNA if the amount or activity of said reporter protein detected in the presence of the compound is not altered or is not substantially altered relative to a previously determined reference range, or relative to the amount or activity of said reporter protein detected in the absence of the compound or the presence of a negative control (e.g., PBS or DMSO). In accordance with this embodiment, the panel may comprise 5, 7, 10, 15, 20, 25, 50, 75, 100 or more cells.

In another embodiment, the specificity of a particular compound for an UTR of Bmi-1 mRNA is determined by (a)

contacting the compound of interest with a cell-free extract and a nucleic acid construct comprising a reporter gene operably linked to an UTR of a different gene; and (b) detecting the amount or activity of a reporter protein translated from the reporter gene, wherein the compound is specific for the untranslated region of said Bmi-1 mRNA if the amount or activity of said reporter protein detected in the presence of the compound is not altered or is not substantially altered relative to a previously determined reference range, or relative to the amount or activity of said reporter protein detected in the absence of the compound or the presence of a negative control (e.g., PBS or DMSO).

In a specific embodiment, the amount or activity of the reporter protein is detected by the same technique whether a compound or a control is used in a screening method described herein, such as immunological techniques, e.g., flow cytometry, ELISA or Western blot.

The compounds identified or validated in the screening methods described herein that modulate untranslated region-dependent expression of Bmi-1 can be further tested for untranslated region-dependent binding to any of the 5'-UTR and 3'-UTR, or the 5'-UTR or the 3'-UTR of Bmi-1, or a fragment or post-transcriptional regulatory element of each thereof. Furthermore, by assessing the effect of a compound on the expression of Bmi-1, cis-acting elements, i.e., specific nucleotide sequences, that are involved in untranslated region-dependent expression may be identified. The compound can also be tested for binding to proteins and/or molecules involved in post-transcriptional expression of Bmi-1. In one embodiment, the proteins and/or molecules involved in post-transcriptional expression of Bmi-1 bind to cis-acting elements in any of the 5'-UTR and 3'-UTR, or the 5'-UTR or the 3'-UTR of Bmi-1.

RNA Binding Assay

Compounds that modulate untranslated region-dependent expression of Bmi-1 can be tested for binding to any of the 5'-UTR and 3'-UTR, or the 5'-UTR or the 3'-UTR of Bmi-1, or a fragment or post-transcriptional regulatory element of each thereof by any method known in the art.

Subtraction Assay

The element(s) of an untranslated region(s) that is (are) necessary for a compound identified in accordance with the methods described herein to modulate untranslated region-dependent expression of Bmi-1 can be determined utilizing standard mutagenesis techniques well-known to one of skill in the art. One or more mutations (e.g., deletions, additions and/or substitutions) may be introduced into an untranslated region(s) operably linked to a reporter gene and the effect on the expression of the reporter gene in an assay as described herein can be determined. For example, a nucleic acid construct comprising the 5'-UTR of Bmi-1 may be mutated by deleting a fragment or all of the 5'-UTR of Bmi-1 or substituting a fragment of the 5'-UTR of Bmi-1 with a fragment of the 5'-UTR of another gene and measuring the expression of the reporter gene in the presence and absence of a compound that has been identified in an instant screening assay described herein. If the deletion of a fragment of the 5'-UTR of Bmi-1 or the substitution of a fragment of the 5'-UTR of Bmi-1 with a fragment of the 5'-UTR of another gene affects the ability of the compound to modulate the expression of the reporter gene, then the fragment of the 5'-UTR deleted or substituted plays a role in the regulation of the reporter gene expression.

Standard techniques known to those of skill in the art can be used to introduce mutations in the nucleotide sequence of an untranslated region of Bmi-1, including, for example, site-directed mutagenesis and PCR-mediated mutagenesis. In a specific embodiment, less than 75 nucleic acid residue substitutions, less than 50 nucleic acid residue substitutions, less than 45 nucleic acid residue substitutions, less than 40 nucleic acid residue substitutions, less than 35 nucleic acid residue substitutions, less than 30 nucleic acid residue substitutions, less than 25 nucleic acid residue substitutions, less than 20 nucleic acid residue substitutions, less than 15 nucleic acid residue substitutions, less than 10 nucleic acid residue substitutions, or less than 5 nucleic acid residue substitutions are introduced into the nucleotide sequence of an untranslated region of Bmi-1. In another embodiment, less than 10 elements of an untranslated region of Bmi-1, less than 9 elements of an untranslated region of Bmi-1, less than 8 elements of an untranslated region of Bmi-1, less than 7 elements of an untranslated region of Bmi-1, less than 6 elements of an untranslated region of Bmi-1, less than 5 elements of an untranslated region of Bmi-1, less than 4 elements of an untranslated region of Bmi-1, less than 3 elements of an untranslated region of Bmi-1, or less than 2 elements of an untranslated region of Bmi-1 are mutated at one time.

Detecting the Expression and Activity of Proteins Encoded by Bmi-1

Compounds identified or validated in the screening methods described herein that modulate untranslated region-dependent expression may be further tested in various in vitro assays (e.g., cell-free assays) or in vivo assays (e.g., cell-based assays) well-known to one of skill in the art or as described herein to determine the effect of said compounds on the expression of Bmi-1 from which the untranslated regions of the nucleic acid construct are derived. The specificity of a particular compound to affect UTR-dependent expression of one or more other genes can also be determined utilizing assays well-known to one of skill in the art or described herein.

The expression of the gene products of Bmi-1 can be readily detected, e.g., by quantifying the protein and/or RNA encoded by said gene. Many methods standard in the art can be thus employed, including, but not limited to, immunoassays to detect and/or visualize protein expression (e.g., Western blot, immunoprecipitation followed by sodium dodecyl sulfate polyacrylamide gel electrophoresis (SDS-PAGE), immunocytochemistry, etc.) and/or hybridization assays to detect gene expression by detecting and/or visualizing respectively mRNA encoding a gene (e.g., northern assays, dot blots, in situ hybridization, etc.). Such assays are routine and well known in the art. Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1 to 4 hours) at 40° C., adding protein A and/or protein G Sepharose beads to the cell lysate, incubating for about an hour or more at 40° C., washing the beads in lysis buffer and resuspending the beads in SDS/sample buffer. The ability of the antibody of interest to immunoprecipitate a particular antigen can be assessed by, e.g., Western blot analysis. One of skill in the art would be knowledgeable as to the parameters that can be modified to increase the binding of the antibody to an antigen and decrease the background (e.g., pre-clearing the cell lysate with sepharose beads).

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), incubating the membrane with primary antibody (the antibody of interest) diluted in blocking buffer, washing the membrane in washing buffer, incubating the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}P$ or $^{125}I$) diluted in blocking buffer, washing the membrane in wash buffer, and detecting the presence of the antigen. One of skill in the art would be knowledgeable as to the parameters that can be modified to increase the signal detected and to reduce the background noise.

ELISA generally comprises preparing an antigen, coating the well of a 96-well microtiter plate with the antigen, adding the antibody of interest conjugated to a detectable agent such as an enzymatic substrate (e.g., horseradish peroxidase or alkaline phosphatase) to the well and incubating for a period of time, and detecting the presence of the antigen. In ELISA, the antibody of interest does not have to be conjugated to a detectable compound; instead, a second antibody (which recognizes the antibody of interest) conjugated to a detectable agent may be added to the well. Further, instead of coating the well with the antigen, the antibody may be coated to the well. In this case, a second antibody conjugated to a detectable agent may be added following the addition of the antigen of interest to the coated well. One of skill in the art would be knowledgeable as to the parameters that can be modified to increase the signal detected as well as other variations of ELISA known in the art.

In another embodiment, the levels of endogenous Bmi-1 are determined by the Bmi-1 Sandwich ELISA. A Sandwich ELISA measures the amount of antigen, in this case Bmi-1, between two layers of antibodies (i.e. capture and detection antibody). The capture antibody is immobilized in the wells of an ELISA plate and when a cell lysate or other sample is added to the plate, the specific protein of interest (Bmi-1) is bound by this capture antibody. A second antibody, called the detecting antibody, is then added, which binds to the bound protein and helps increase the signal. The antigen to be measured must contain at least two antigenic sites capable of binding to antibody. Either monoclonal or polyclonal antibodies can be used as the capture and detection antibodies in Sandwich ELISA systems. Monoclonal antibodies recognize a single epitope that allows fine detection and quantification of cancer differences in antigen. A polyclonal is often used as the capture antibody to pull down as much of the antigen as possible.

A decreased level of Bmi-1 protein indicates that the compound may be effective to treat cancer. Decreased levels of Bmi-1 protein in conjunction with no change in the levels of Bmi-1 indicate that the compound affects UTR-dependent expression of Bmi-1 protein and not promoter-dependent expression (transcription) of Bmi-1 RNA. Decreased levels of target Bmi-1 protein in conjunction with increased levels of Bmi-1 RNA may indicate that the compound affects UTR-dependent expression of target protein and not promoter-dependent expression of Bmi-1 RNA (i.e., transcriptional regulation via the promoter/enhancer of Bmi-1). Specific examples of cell culture models from patients with cancer may be used. Other cell culture models that may be used include, but are not limited to, 293H cells and RD cell cultures. The in vivo effect of the compound can also be assayed by performing immunofluorescence studies using antibodies against the Bmi-1 protein. Another antibody based separation that can be used to detect the protein of interest is the use of flow cytometry such as by a florescence activated cell sorter ("FACS").

A phenotypic or physiological readout can be used to assess untranslated region-dependent activity of Bmi-1 RNA in the presence and absence of the compound. In one embodiment, a phenotypic or physiological readout can be used to assess untranslated region-dependent activity of Bmi-1 RNA in the presence and absence of the compound. For example, Bmi-1 RNA may be overexpressed in a cell in which said Bmi-1 RNA is endogenously expressed. Where untranslated regions of Bmi-1 regulate the expression of Bmi-1, the in vivo effect of the compound can be assayed by quantifying Bmi-1 transcript or Bmi-1 protein present in cells and/or biological samples obtained from a subject to which the compound was administered.

In addition to measuring the effect of a compound identified in the reporter gene-based assays described herein on the expression of the Bmi-1 gene from which the untranslated regions of the nucleic acid construct were derived, the amount or activity of the protein encoded by Bmi-1 genes can be assessed utilizing techniques well-known to one of skill in the art. For example, the activity of a protein encoded by Bmi-1 can be determined by detecting the levels of endogenous ubiquitinated histone 2A (Ub-H2A) in cells via Western Blot analysis. Normally, Bmi-1 associates with RING1B to form a complex that has E3 ligase activity and ubiquitinates H1stone H2A (Cao et al., Mol. Cell. 2005, 20(6): 845-54; Li et al., J Biol. Chem. 2006, 281(29):20643-9; Buchwald et al., EMBO J. 2006, 25(11): 2465-74). Loss of Bmi-1 will reduce the E3 ligase activity of Ring-1B and will result in a decrease in Ub-H2A protein levels. The activity of a protein encoded by Bmi-1 can also be determined by detecting RNA and protein expression levels of genes involved in the ink4a signal transduction pathway via RT-PCR and Western Blot analysis, respectively. Such genes include, but are not limited to, $p16^{ink4a}$ and $p14^{arf}$.

Secondary Screens of Compounds

Compounds identified or validated to modulate untranslated region-dependent expression of Bmi-1 may be tested for biological activity in further assays and/or animal models as described herein or known to those skilled in the art.

Cytotoxicity Assays

In some embodiments, compounds are tested for cytotoxicity in mammalian, preferably human, cell lines. In certain embodiments, cytotoxicity is assessed in one or more of the following non-limiting examples of cell lines: U937, a human monocyte cell line; primary peripheral blood mononuclear cells (PBMC); a human hepatoblastoma cell line such as Huh7; a human embryonic kidney cell line such as HL60, HEK 293T, HEK 293H and MLPC; and THP-1, monocytic cells; a HeLa cell line; a rhabdomyosarcoma cell line; a fibrosarcoma cell line such as HT1080; a myeloid leukemia cell line such as K562 or KG1; a glioblastoma cell line such as U87-MG or T98G; a neuroblastoma cell line such as MC-IXC, SK-N-MC, SK-N-MC, SK-N-DZ, SH-SY5Y or BE(2)-C. In certain embodiments, cytotoxicity is assessed in stem cells. In other embodiments, cytotoxicity is assessed in various cancer cells. In some embodiments, the ToxLite assay is used to assess cytotoxicity.

Many assays well-known in the art can be used to assess viability of cells (infected or uninfected) or cell lines following exposure to a compound and, thus, determine the cytotoxicity of the compound. For example, cell proliferation can be assayed by measuring Bromodeoxyuridine (BrdU) incorporation, (3H) thymidine incorporation, by direct cell count, or by detecting changes in transcription, translation or activity of known genes such as proto-oncogenes (e.g., fos, myc) or cell cycle markers (Rb, cdc2, cyclin A, D1, D2, D3, E, etc). The levels of such protein and mRNA and activity can be determined by any method well known in the art. For example, protein can be quantitated by known immunodiagnostic methods such as ELISA, Western blotting or immunoprecipitation using antibodies, including commercially available antibodies. The amount of mRNA can be quantitated using methods that are well known and routine in the art, for example, using northern analysis, RNase protection, or polymerase chain reaction in connection with reverse transcription. Cell viability can be assessed by using trypan-blue staining or other cell death or viability markers known in the art. In a specific embodiment, the level of cellular ATP is measured to determined cell viability.

In specific embodiments, cell viability is measured in three-day and seven-day periods using an assay standard in the art, such as the CellTiter-Glo Assay Kit (Promega) which measures levels of intracellular ATP. A reduction in cellular ATP is indicative of a cytotoxic effect. In another specific embodiment, cell viability can be measured in the neutral red uptake assay. In other embodiments, visual observation for morphological changes may include enlargement, granularity, cells with ragged edges, a filmy appearance, rounding, detachment from the surface of the well, or other changes. These changes are given a designation of T (100% toxic), PVH (partially toxic—very heavy—80%), PH (partially toxic—heavy—60%), P (partially toxic-40%), Ps (partially toxic—slight—20%), or 0 (no toxicity—0%), conforming to the degree of cytotoxicity seen. A 50% cell inhibitory (cytotoxic) concentration ($IC_{50}$) is determined by regression analysis of these data.

Compounds can be tested for in vivo toxicity in animal models. For example, animal models, described herein and/or others known in the art, used to test the effects of compounds on cancer can also be used to determine the in vivo toxicity of these compounds. For example, animals are administered a range of concentrations of compounds. Subsequently, the animals are monitored over time for lethality, weight loss or failure to gain weight, and/or levels of serum markers that may be indicative of tissue damage (e.g., creatine phosphokinase level as an indicator of general tissue damage, level of glutamic oxalic acid transaminase or pyruvic acid transaminase as indicators for possible liver damage). These in vivo assays may also be adapted to test the toxicity of various administration mode and/or regimen in addition to dosages.

The toxicity and/or efficacy of a compound identified or validated in accordance with the method described herein can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. A compound identified in accordance with the method described herein that exhibits large therapeutic indices is preferred. While a compound described herein that exhibits toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of a compound identified in accordance with the method described herein for use in humans. The dosage of such agents lies preferably within a range of circulating concentrations that include the $ED_{50}$ with little or no toxicity. The dosage may vary within this range depending upon the dosage form employed and the route of administration utilized. For any agent used in the method described herein, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high-performance liquid chromatography.

Animal Model-Based Screens

Compounds identified in the reporter gene-based screening methods described herein can be tested for biological activity using cancer animal models. These include animals engineered to express Bmi-1 coupled to a functional readout system, such as a transgenic mouse. Such animal model systems include, but are not limited to, rats, mice, chicken, cows, monkeys, pigs, dogs, rabbits, etc. In a specific embodiment, a compound identified in accordance with the methods described herein is tested in a mouse model system. Such model systems are widely used and well-known to the skilled artisan such as the SCID mouse model or transgenic mice.

The Bmi-1 inhibitory activity of a compound described herein can be determined by administering the compound to an animal model and verifying that the compound is effective in reducing the severity of cancer in said animal model. Examples of animal models for cancer in general include, include, but are not limited to, spontaneously occurring tumors of companion animals (see, e.g. Vail & MacEwen, 2000, Cancer Invest 18(8):781-92). Examples of animal models for lung cancer include, but are not limited to, lung cancer animal models described by Zhang & Roth (1994, In-vivo 8(5):755-69) and a transgenic mouse model with disrupted p53 function (see, e.g. Morris et al., 1998, J La State Med Soc 150(4): 179-85). An example of an animal model for breast cancer includes, but is not limited to, a transgenic mouse that over expresses cyclin D1 (see, e.g. Hosokawa et al., 2001, Transgenic Res 10(5):471-8). An example of an animal model for colon cancer includes, but is not limited to, a TCR b and p53 double knockout mouse (see, e.g. Kado et al., 2001, Cancer Res. 61(6):2395-8). Examples of animal models for pancreatic cancer include, but are not limited to, a metastatic model of PancO2 murine pancreatic adenocarcinoma (see, e.g., Wang et al., 2001, Int. J. Pancreatol. 29(1):37-46) and nu-nu mice generated in subcutaneous pancreatic tumors (see, e.g. Ghaneh et al., 2001, Gene Ther. 8(3):199-208). Examples of animal models for non-Hodgkin's lymphoma include, but are not limited to, a severe combined immunodeficiency ("SCID") mouse (see, e.g. Bryant et al., 2000, Lab Irlvest 80(4):553-73) and an IgHmu-HOX11 transgenic mouse (see, e.g. Hough et al., 1998, Proc. Natl. Acad. Sci. USA 95(23):13853-8). An example of an animal model for esophageal cancer includes, but is not limited to, a mouse transgenic for the human papillomavirus type 16 E7 oncogene (see, e.g. Herber et al., 1996, J. Virol. 70(3):1873-81). Examples of animal models for colorectal carcinomas include, but are not limited to, Apc mouse models (see, e.g., Fodde & Smits, 2001, Trends Mol Med 7(8):369 73 and Kuraguchi et al., 2000)

Compositions

Any compound described herein may optionally be in the form of a composition comprising the compound. In certain embodiments provided herein, pharmaceutical compositions comprise an effective amount of a compound for down-regulating Bmi-1 protein expression in an admixture with a pharmaceutically acceptable carrier, excipient, or diluent. The pharmaceutical compositions are suitable for veterinary and/or human administration. Accordingly, the compounds identified or validated in accordance with the method described herein may be used in a method for treating cancer in a subject, e.g., a human subject, in need thereof, comprising administering to a subject, e.g., a human subject, an effective amount of such a pharmaceutical composition. In another embodiment, one or more compounds identified or validated to down-regulate Bmi-1 protein expression may be used in the preparation of a pharmaceutical composition for treating cancer in a human subject in need thereof.

The pharmaceutical compositions provided herein can be in any form that allows for the composition to be administered to a subject, said subject preferably being an animal, including, but not limited to a human, mammal, or non-human animal, such as a cow, horse, sheep, pig, fowl, cat, dog, mouse, rat, rabbit, guinea pig, etc., and is more preferably a mammal, and most preferably a human.

In a specific embodiment and in this context, the term "pharmaceutically acceptable carrier, excipient or diluent" means a carrier, excipient or diluent approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions.

Typical compositions and dosage forms comprise one or more excipients. Suitable excipients are well-known to those skilled in the art of pharmacy, and non limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a patient and the specific active ingredients in the dosage form. The composition or single unit dosage form, if desired, can also contain minor amounts of wetting or emulsifying agents, or pH buffering agents. Further provided herein are anhydrous pharmaceutical compositions and dosage forms comprising one or more compounds described herein. The compositions and single unit dosage forms can take the form of solutions, suspensions, emulsion, tablets, pills, capsules, powders, sustained-release formulations and the like. Compositions provided herein are formulated to be compatible with the intended route of administration. Examples of routes of administration include, but are not limited to, parenteral, e.g., intravenous, intradermal, subcutaneous, oral (e.g., inhalation), intranasal, transdermal (topical), transmucosal, intra-synovial and rectal administration.

Pharmaceutical compositions provided herein that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by pharmaceutical methods well known to those skilled in the art.

Typical oral dosage forms provided herein are prepared by combining a compound in intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro crystalline cellulose, diluents, granulating agents, lubricants, binders, and disintegrating agents.

Because of their ease of administration, tablets and capsules' represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre gelatinized starch, hydroxypropyl methyl cellulose, microcrystalline cellulose, and mixtures thereof. Disintegrants that can be used in pharmaceutical compositions and dosage forms provided herein include, but are not limited to, agar, alginic acid, calcium carbonate, microcrystalline cellulose, croscarmellose sodium, crospovidone, polacrilin potassium, sodium starch glycolate, potato or tapioca starch, pre gelatinized starch, other starches, clays, other algins, other celluloses, gums, and mixtures thereof. Lubricants that can be used in pharmaceutical compositions and dosage forms provided herein include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonSeed oil, sunflower oil, sesame oil, olive oil, corn oil, and soybean oil), zinc stearate, ethyl oleate, ethyl laureate, agar, and mixtures thereof.

A compound described herein can be administered by controlled release means or by delivery devices that are well known to those of ordinary skill in the art. Such dosage forms can be used to provide slow or controlled release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. The use of compounds described herein include use in a single unit dosage form suitable for oral administration such as, but not limited to, tablets, capsules, gelcaps, and caplets that are adapted for controlled release.

Parenteral dosage forms can be administered to patients by various routes including, but not limited to, subcutaneous, intravenous (including bolus injection), intramuscular, and intraarterial. Because their administration typically bypasses a patients natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. Transdermal, topical, and mucosal dosage forms provided herein include, but are not limited to, ophthalmic solutions, sprays, aerosols, creams, lotions, ointments, gels, solutions, emulsions, suspensions, or other forms known to one of skill in the art. Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

In certain specific embodiments, the compositions are in oral, injectable, or transdermal dosage forms. In one specific embodiment, the compositions are in oral dosage forms. In another specific embodiment, the compositions are in the form of injectable dosage forms. In another specific embodiment, the compositions are in the form of transdermal dosage forms.

Pharmaceutical Methods

The methods described herein provide a method for post-transcriptionally modulating the expression of Bmi-1 in a subject, e.g., a human subject, in need thereof, comprising administering an effective amount of a compound described herein to the subject, in which said compound decreases or down-regulates in vitro or in cultured cells the post-transcriptional expression of a nucleic acid construct comprising a reporter gene operably linked to any of the 5'-UTR and 3'-UTR, or the 5'-UTR or the 3'-UTR of Bmi-1, wherein the 5'-UTR is upstream of the reporter gene and the 3'-UTR of Bmi-1 is downstream of the reporter gene. The methods described herein also provide for treating cancer, in a subject, e.g., a human subject, in need thereof, comprising administering an effective amount of a compound to the subject, in which said compound decreases or down-regulates in vitro or in cultured cells the post-transcriptional expression of a nucleic acid construct comprising a reporter gene operably linked to any of the 5'-UTR and 3'-UTR, or the 5'-UTR or the 3'-UTR of Bmi-1, wherein the 5'-UTR of Bmi-1 is upstream of the reporter gene and the 3'-UTR of Bmi-1 is downstream of the reporter gene.

The methods described herein also provide a method of treating cancer in a subject, e.g., a human subject, in need thereof, said method comprising administering to the subject an effective amount of one or more compounds described herein. In specific embodiments, a compound described herein is the only active ingredient administered to treat cancer. In a certain embodiment, a compound described herein is the only active ingredient in a composition.

In some embodiments, a compound described herein decreases or down-regulates Bmi-1 protein expression by 5%, 10%, 15%, 20%, 25%, 35%, 45%, 50%, 55%, 65%, 70%, 75%, 80%, 85%, 90% or 95% relative to a negative control (e.g., PBS or 0.5-1.0% DMSO) as determined by the screening methods described herein or known in the art. In some embodiments, a compound described herein administered to a subject decreases Bmi-1 mRNA stability by about 5%, 10%, 15%, 20%, 25%, 35%, 45%, 50%, 55%, 65%, 70%, 75%, 80%, 85%, 90% or 95% relative to the negative control, as determined by mRNA stability assays (e.g., Northern blot or RT-PCR). In some embodiments, a compound described herein that is administered decreases or down-regulates Bmi-1 protein translation by 5%, 10%, 15%, 20%, 25%, 35%, 45%, 50%, 55%, 65%, 70%, 75%, 80%, 85%, 90% or 95% relative to a negative control as determined by assays known in the art, e.g., Western blotting, ELISA assay, flow cytometry.

In certain embodiments, a compound described herein decreases or down-regulates the amount or activity of a reporter protein or Bmi-1 protein by at least 1.5 fold, 2 fold, 3 fold, 4 fold, 5 fold, 6 fold, 7 fold, 8 fold, 9 fold, or 10 fold greater than the amount of activity of said reporter protein or Bmi-1 protein detected in the absence of the compound or in the presence of a negative control, as determined by an assay described herein or known in the art, e.g., ELISA, western blot, or FACs.

The effective amount of a compound described herein used to decrease or down-regulate the post-transcriptional expression of Bmi-1 depends on a number of factors, including but not limited to the type of cancer, health and age of the patient, and toxicity or side effects. The methods described herein also encompass methods for treating cancer for which no treatment is available. The methods described herein also encompass methods for treating cancer as an alternative to other conventional therapies.

The methods described herein provide a method of treating cancer in a subject in need thereof, said method comprising administering to the subject one or more of the compounds described herein and one or more additional agents. In a specific embodiment, the other therapies are currently being used, have been used or are known to be useful in treating cancer. In another embodiment, one or more compounds described herein are administered to a subject in combination with a supportive therapy, a pain relief therapy, or other therapy that does not have a therapeutic effect on cancer.

In some embodiments, a compound described herein is administered to a subject suffering from cancer. In other embodiments, a compound described herein is administered to a subject predisposed or susceptible to cancer. In some embodiments, a compound described herein or a composition thereof is administered to a subject diagnosed with cancer. Non-limiting examples of the types of cancer are described herein. In an embodiment, the patient has metastatic cancer. In another embodiment, the patient is in remission. In yet another embodiment, the patient has a recurrence of cancer.

In certain embodiments, a compound described herein is administered to a human that is 0 to 6 months old, 6 to 12 months old, 6 to 18 months old, 18 to 36 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In some embodiments, a compound described herein is administered to a human infant. In other embodiments, a compound described herein is administered to a human toddler. In other embodiments, a compound described herein is administered to a human child. In other embodiments, a compound described herein is administered to a human adult. In yet other embodiments, a compound described herein is administered to an elderly human.

In certain embodiments, a compound is administered to a subject who is in an immunocompromised state or immunosuppressed state or at risk for becoming immunocompromised or immunosuppressed. In certain embodiments, a compound is administered to a subject receiving or recovering from immunosuppressive therapy. In certain embodiments, a compound is administered to a subject that has or is at risk of getting cancer, AIDS, or a bacterial infection. In certain embodiments, the subject is, will or has undergone surgery, chemotherapy and/or radiation therapy. In certain embodiments, a compound is administered to a subject that has cystic fibrosis, pulmonary fibrosis or another condition affecting the lungs. In certain embodiments, a compound is administered to a subject that has, will have or had a tissue transplant.

In some embodiments, one or more compounds are administered to a patient who has proven refractory to therapies other than compounds, but are no longer on these therapies. In one embodiment, a cancer refractive to a therapy refers to a cancer in which at least some significant portion of the cancer cells are not killed or in which cell division has not been arrested. The determination of whether the cancer cells are refractive can be made either in vivo or in vitro by any method known in the art for assaying the effect of a therapy on cancer cells, using the art-accepted meanings of "refractory" in such a context. In one embodiment, a refractory patient is a patient refractory to a standard therapy. In another embodiment, a patient with cancer is refractory to a therapy when the tumor or neoplasm has not significantly been eradicated and/or the symptoms have not been significantly alleviated. The determination of whether a patient is refractory can be made either in vivo or in vitro by any method known in the art for assaying the effectiveness of a treatment of cancer, using art-accepted meanings of "refractory" in such a context.

In certain embodiments, the patient to be treated in accordance with the methods described herein are patients already being treated with antibiotics, anti-virals, anti-fungals, or other biological therapy/immunotherapy or anti-cancer therapy. Among these patients are refractory patients, and patients who are too young for conventional therapies. In some embodiments, the subject being administered one or more compounds has not received a therapy prior to the administration of a compound described herein.

In some embodiments, compounds are administered to a patient to prevent the onset of cancer in a patient at risk of developing cancer. In some embodiments, compounds are administered to a patient who is susceptible to adverse reactions to conventional therapies.

In some embodiments, the subject being administered one or more compounds is treatment naïve (i.e., has not received prior therapy). In other embodiments, one or more compounds are administered to a subject who has received a therapy prior to administration of one or more compounds. In some embodiments, the subject administered a compound has experienced adverse side effects to the prior therapy or the prior therapy was discontinued due to unacceptable levels of toxicity to the subject.

In some embodiments, the subject being administered one or more compounds will or has undergone surgery, chemotherapy, antibody therapy, hormonal therapy and/or radiation therapy. In certain embodiments, the patient has undergone surgery to remove a tumor or neoplasm. In certain embodiments, a compound or composition thereof is being administered to a subject that will have, or has had, or is undergoing a tissue or organ transplant.

The amount of a compound or a form or pharmaceutical composition thereof that decreases the amount of Bmi-1 protein by modulating UTR-dependent expression of Bmi-1 that will be effective in the treatment of cancer can be determined by standard clinical techniques. In vitro or in vivo assays may optionally be employed to help identify optimal dosage ranges. The precise dose to be employed will also depend, e.g., on the route of administration, the type of disease to be treated, and the seriousness of the disease to be treated, and should be decided according to the judgment of the practitioner and each patient's or subject's circumstances.

Exemplary doses of a compound or a form or pharmaceutical composition thereof that down-regulates Bmi-1 protein by modulating UTR-dependent expression of Bmi-1 include milligram (mg) or microgram (n) amounts per kilogram (Kg) of subject or sample weight per day such as from about 1 µg per Kg to about 500 mg per Kg per day, from about 1 µg per Kg to about 500 mg per Kg per day, from about 5 µg per Kg to about 100 mg per Kg per day, or from about 10 µg per Kg to about 100 mg per Kg per day. In another embodiment, the dosage is a unit dose of about 0.1 mg, 1 mg, 5 mg, 10 mg, 50 mg, 100 mg, 150 mg, 200 mg, 250 mg, 300 mg, 350 mg, 400 mg, 500 mg, 550 mg, 600 mg, 650 mg, 700 mg, 750 mg, 800 mg or more. In another embodiment, the dosage is a unit dose that ranges from about 0.1 mg to about 1000 mg, from about 1 mg to about 1000 mg, from about 5 mg to about 1000 mg, from about 10 mg to about 500 mg, from about 100 mg to about 500 mg, from about 150 mg to about 500 mg, from about 150 mg to about 1000 mg, from about 250 mg to about 1000 mg, from about 300 mg to about 1000 mg, or from about 500 mg to about 1000 mg.

In certain embodiments, suitable dosage ranges for oral administration are about 0.001 milligram to about 500 milligrams of a compound, per kilogram body weight per day. In specific embodiments for use of the compounds described herein, the oral dose is about 0.01 milligram to about 100 milligrams per kilogram body weight per day, about 0.1 milligram to about 75 milligrams per kilogram body weight per day or about 0.5 milligram to 5 milligrams per kilogram body weight per day. The dosage amounts described herein refer to total amounts administered; that is, if more than one compound is administered, then, in some embodiments, the dosages correspond to the total amount administered. In a specific embodiment, oral compositions contain about 10% to about 95% a compound by weight.

In another embodiment, a subject is administered one or more doses of an effective amount of a compound described herein or a composition thereof, wherein the effective amount may not be the same for each dose.

The methods described herein provide for methods of treating cancer in a subject in need thereof comprising administering to the subject an effective amount of one or more of the compounds or a form or pharmaceutical composition thereof that down-regulate the post-transcriptional expression of Bmi-1 alone or in combination with one or more additional agents, e.g., anti-cancer or immunomodulatory agents. In another embodiment, one or more compounds or a form or pharmaceutical composition thereof that down-regulates the post-transcriptional expression of Bmi-1 alone or in combination with one or more additional agents may be administered to the subject in combination with a supportive therapy, a pain relief therapy, or other therapy that has no effect on cancer.

In some embodiments, one or more compounds or a form thereof that down-regulates the post-transcriptional expression of Bmi-1 and one or more additional agents are administered as the same pharmaceutical composition. In certain embodiments, one or more compounds or a form thereof that down-regulates the post-transcriptional expression of Bmi-1 and one or more additional agents are administered in different pharmaceutical compositions. In certain embodiments, one or more compounds or a form or pharmaceutical composition thereof that down-regulates the post-transcriptional expression of Bmi-1 and one or more additional agents are administered by the same route of administration. In certain embodiments, one or more compounds or a form or pharmaceutical composition thereof that down-regulates the post-transcriptional expression of Bmi-1 and one or more additional agents are administered by different routes of administration.

Additional agents that can be used in a combination product with compounds that down-regulate Bmi-1 protein expression for the treatment of cancer include, but are not limited to, small molecules, synthetic drugs, peptides (including cyclic peptides), polypeptides, proteins, nucleic acids (e.g., DNA and RNA nucleotides including, but not limited to, antisense nucleotide sequences, triple helices, siRNA, RNAi, miRNA and nucleotide sequences encoding biologically active proteins, polypeptides or peptides), antibodies, synthetic or natural inorganic molecules, mimetic agents, and synthetic or natural organic molecules.

In some embodiments, a compound described herein may be used in combination with radiation therapy comprising the use of x-rays, gamma rays and other sources of radiation to destroy cancer stem cells and/or cancer cells. In specific embodiments, the radiation therapy is administered as external beam radiation or teletherapy, wherein the radiation is directed from a remote source. In other embodiments, the radiation therapy is administered as internal therapy or brachytherapy wherein a radioactive source is placed inside the body close to cancer stem cells, cancer cells and/or a tumor mass.

Currently available cancer therapies and their dosages, routes of administration and recommended usage are known in the art and have been described in such literature as the *Physician's Desk Reference* ($60^{th}$ ed., 2006). In accordance with the methods described herein, the dosages and frequency of administration of chemotherapeutic agents are described herein.

In some embodiments, additional agents that can be used in combination with the compounds described herein for the treatment of cancer, include, but are not limited to, agents that decrease or down-regulate the transcription of Bmi-1. In certain embodiments, the agent is specific for the transcriptional promoter/enhancer of Bmi-1. In particular embodiments, the agent is specific for a transcription factor that binds to the translational, post-transcriptional or transcriptional promoter/enhancer of Bmi-1 and that decreases or down-regulates transcription of Bmi-1. In some embodiments, the agent is specific for a transcriptional repressor that binds to the transcriptional promoter/enhancer of Bmi-1 and inhibits transcription, or that binds to a transcription factor of Bmi-1 and inhibits the activity of the transcription factor.

Any compound or therapy which is known to be useful, or which has been used or is currently being used for the treatment of cancer, can be used in combination with the compounds described herein. See, e.g., Gilman et al., Goodman and Gilman's: The Pharmacological Basis of Therapeutics, 10th ed., McGraw-Hill, New York, 2001; The Merck Manual of Diagnosis and Therapy, Berkow, M. D. et al. (eds.), 17th Ed., Merck Sharp & Dohme Research Laboratories, Rahway, N.J., 1999; Cecil Textbook of Medicine, 20th Ed., Bennett and Plum (eds.), W.B. Saunders, Philadelphia, 1996, and Physicians' Desk Reference (61st ed. 1007) for information regarding therapies (e.g., prophylactic or therapeutic agents) which have been or are currently being used for preventing, treating and/or managing cancer.

Types of Cancer

Any type of cancer can be treated in accordance with the methods described herein. In one embodiment, a cancer is characterized by cells that aberrantly express Bmi-1. In another embodiment, a cancer is characterized by cells that overexpress Bmi-1 relative to cells from a cancer-free patient (i.e., a patient with no detectable cancer as determined by conventional techniques, such as MRI, CAT scan etc.) by at least 10%, 25%, 35%, 45%, 55%, 65%, 75%, 85%. 90%, or 95% more, as detected by any method routinely used in the art, or described herein, e.g., in an ELISA.

Non-limiting examples of cancers that can be treated in accordance with the methods described herein include: leukemias, such as but not limited to, acute leukemia, acute lymphocytic leukemia, acute myelocytic leukemias, such as, myeloblastic, promyelocytic, myelomonocytic, monocytic, and erythroleukemia leukemias and myelodysplastic syndrome; chronic leukemias, such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, placancer cell leukemia, solitary placancercytoma and extramedullary placancercytoma; Waldenström's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including but not limited to ductal carcinoma, adenocarcinoma, lobular (cancer cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipidus; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cystic carcinoma, mucoepidermoid carcinoma, adenosquamous carcinoma, sarcoma, melanoma, placancercytoma, verrucous carcinoma, and oat cell (cancer cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma; gallbladder cancers such as adenocarcinoma; cholangiocarcinomas such as but not limited to papillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, prostatic intraepithelial neoplasia, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell carcinoma, adenocarcinoma, hypernephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, *Medicine,* 2d Ed., J.B. Lippincott Co., Philadelphia and Murphy et al., 1997, *Informed Decisions: The Complete Book of Cancer Diagnosis, Treatment, and Recovery*, Viking Penguin, Penguin Books U.S.A., Inc., United States of America).

The compounds are also useful in the treatment, prevention and/or management of a variety of cancers or other abnormal proliferative diseases, including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T cell lymphoma, Burkett's lymphoma, Burkitt's lymphoma or Mantle Cell Lymphoma; hematopoietic tumors of myeloid lineage, including acute and chronic myelogenous leukemias and promyelocytic leukemia; tumors of mesenchymal origin, including fibrosarcoma and rhabdomyosarcoma; other tumors, including melanoma, seminoma, teratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyosarcoma, and osteosarcoma; and other tumors, including melanoma, xeroderma pigmentosum, keratoctanthoma, seminoma, thyroid follicular cancer and teratocarcinoma. In some embodiments, cancers associated with aberrations in apoptosis are treated in accordance with the methods described herein. Such cancers may include, but are not limited to, follicular lymphomas, carcinomas with p53 mutations, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders of the skin, lung, liver, bone, brain, stomach, colon, breast, prostate, bladder, kidney, pancreas, ovary, and/or uterus are treated in accordance with the methods described herein. In other specific embodiments, a sarcoma, or melanoma is treated in accordance with the methods described herein.

In a specific embodiment, the cancer being treated in accordance with the methods described herein is leukemia, lymphoma or myeloma (e.g., multiple myeloma).

Non-limiting examples of leukemias and other blood-borne cancers that can be treated with the methods described herein include acute lymphoblastic leukemia "ALL," acute lymphoblastic B-cell leukemia, acute lymphoblastic T-cell leukemia, acute myeloblastic leukemia "AML," acute promyelocytic leukemia "APL," acute monoblastic leukemia, acute erythroleukemia leukemia, acute megakaryoblastic leukemia, acute myelomonocytic leukemia, acute nonlymphocytic leukemia, acute undifferentiated leukemia, chronic myelocytic leukemia "CML," chronic lymphocytic leukemia "CLL," and hairy cell leukemia.

Non-limiting examples of lymphomas that can be treated in accordance with the methods described herein include Hodgkin's disease, non-Hodgkin's Lymphoma, Multiple myeloma, Waldenström's macroglobulinemia, Heavy chain disease, and Polycythemia vera.

In another embodiment, the cancer being treated in accordance with the methods described herein is a solid tumor. Examples of solid tumors that can be treated in accordance with the methods described herein include, but are not limited to fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma.

The methods described herein are not to be limited in scope by the specific embodiments described herein. Indeed, various modifications of the methods described herein in addition to those described will become apparent to those skilled in the art from the foregoing description and accompanying figures. Such modifications are intended to fall within the scope of the appended claims.

All references cited herein are incorporated herein by reference in their entirety and for all purposes to the same extent as if each individual publication or patent or patent application was specifically and individually indicated to be incorporated by reference in its entirety for all purposes.

EXAMPLES

Example 1

UTR-Mediated Regulation of Bmi-1 Expression

Figure 6A:
FIGS. 6A-6D: Bmi-1 UTR Constructs: Schematic representation of the following Bmi-1-UTR constructs: 6A) pcDNA3.1/Bmi-1 5'+3'-UTR.luc, comprising, in the following order, the human Bmi-1 5'-UTR, the first 21 nucleotides from the 5' end of the ORF of human Bmi-1, the luciferase reporter gene, the last 21 nucleotides from the 3' end of the ORF of human Bmi-1 and the 3'-UTR of human Bmi-1. 6B) pcDNA3.1/Bmi-1 5'-UTR.luc, comprising, in the following order, the 5'-UTR of human Bmi-1, the first 21 nucleotides from the 5' end of the ORF of human Bmi-1, the luciferase reporter gene, and a control UTR from the vector. 6C) pcDNA3.1/Bmi-1 3'-UTR.luc, comprising, in the following order, a control UTR from the vector, the luciferase reporter gene, the last 21 nucleotides from the 3' end of the ORF of human Bmi-1 and the 3'-UTR of human Bmi-1. 6D) pcDNA3.1.luc, comprising, in the following order, a control 5'-UTR from vector, the luciferase reporter gene, and the control 3'-UTR from the vector.
Figure 6B:
Figure 6C:
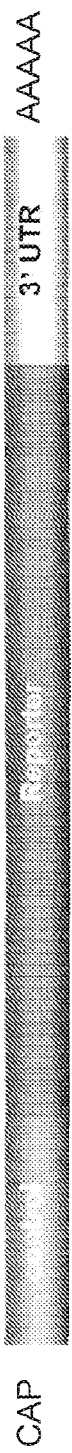
Figure 6D:
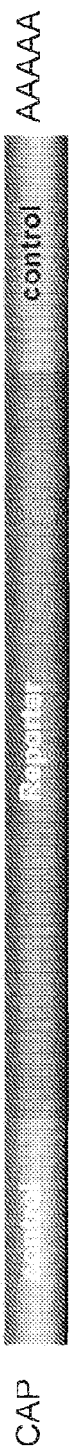

To determine the role of each Bmi-1 UTR in the regulation of protein expression of Bmi-1, the following constructs were generated: (i) pcDNA3.1/Bmi-1 5'-UTR.luc (FIG. 6B): a construct comprising the firefly luciferase gene operably linked and downstream of the 5'-UTR of human Bmi-1 and 21 nucleotides from the 5' end of the ORF of human Bmi-1; (ii) pcDNA3.1/Bmi-1 3'-UTR.luc (FIG. 6C): a construct comprising the firefly luciferase gene operably linked and upstream of 21 nucleotides from the 3' end of the ORF of human Bmi-1 and the 3'-UTR of human Bmi-1; (iii) pcDNA3.1/Bmi-1 5'+3'-UTR.luc (FIG. 6A): a construct comprising the 5'-UTR of human Bmi-1, 21 nucleotides from the 5' end of the ORF of human Bmi-1, the firefly luciferase gene, 21 nucleotides from the 3' end of human Bmi-1 and the 3'-UTR of human Bmi-1, wherein the 5'-UTR of human Bmi-1 and the 21 nucleotides from the 5' end of the ORF of human Bmi-1 are upstream of the luciferase gene, and the 21 nucleotides from the 3' end of human Bmi-1 and the 3'-UTR of human Bmi-1 are downstream of the luciferase gene; and (iv) pcDNA3.1.luc, a construct comprising the luciferase gene flanked by control UTRs on the pcDNA3 vector.

Nucleic Acid Constructs

All DNA constructs were generated using standard procedures (Sambrook, J., Fritsch, E. & Maniatis, T. *Molecular cloning: A laboratory manual* (Cold Spring Harbor Laboratory Press, Cold Spring Harbor, N.Y., 1989)). All PCR reagents were purchased from Invitrogen and the restriction enzymes were bought from New England Boilable.

Generation of Bmi-1 UTRs

The Bmi-1 UTRs were amplified from commercially available full-length cDNA (Origene TrueClone Collection, GenBank Accession No. NM_005180). For cloning the 5'-UTR, a forward primer (5' tttggatcctaacagcaactat-gaaataatcgtagtatgagaggcagag 3'; SEQ ID NO: 3) and a reverse primer (5' tttggatcctaatgagaggcagagatcggggcgagac 3'; SEQ ID NO: 4) were synthesized (Qiagen) and used in a PCR reaction. For easy subcloning, a BamHI site (ggatcc) was added to the end of these two primers. The forward primer also contained a TAA stop codon that was in-frame with the renilla luciferase start codon once inserted to the p2luc vector at the BgIII and BamHI site. The final PCR product included the 5'-UTR, the Bmi-1 ATG, and the first seven amino acids of the ORF.

The Bmi-1 3'-UTR was also amplified from Origene's full-length cDNA TrueClone with a forward primer (5' tttctc-gagtcatcagcaacttcttctggttgatac 3'; SEQ ID NO: 5) and a reverse primer (5' tttctcgagctaaatgaatatcctttttattggatt 3'; SEQ ID NO: 6). XhoI sites were added to both sides of the 3'-UTR during PCR. The final PCR product included the last seven amino acids of the Bmi-1 ORF and its "tga" stop codon, in addition to the 3'-UTR sequence.

Both the 5'-UTR and 3'-UTR of Bmi-1 were subsequently verified by DNA sequencing after they were cloned into the pCR4Blunt-TOPO vector (Invitrogen).

Preparation of the Nucleic Acid Constructs

A high-level expression vector, pcDNA3.1/hygro (Invitrogen Corp., Carlsbad, Calif.) was used for preparing the constructs. All DNA constructs were generated using standard procedures (Sambrook, J., Fritsch, E. & Maniatis, T. *Molecular cloning: A laboratory manual* (Cold Spring Harbor Laboratory Press, Cold Spring Harbor, N.Y., 1989)).

pcDNA3.1/Bmi-1 5'-UTR.luc (FIG. 6B) was constructed by blunt-end ligating Sal I/PmI I fragment from p2luc/Bmi-1 5'-UTR with EcoR V treated pcDNA3.1Hygro vector. Briefly, the Bmi-1 5'-UTR and firefly luciferase gene were isolated from p2luc/Bmi-1 5'-UTR using Sal I and PmI I digestion, followed by filling in with T4 DNA polymerase. The pcDNA3.1 vector was treated with EcoR V followed by dephosphorylation with Alkaline Phosphatase (New England Biolabs). The treated insert was then cloned into the vector by blunt-end ligation with T4 ligase (NEB).

pcDNA3.1/Bmi-1 5'+3'-UTR.luc (FIG. 6A) was constructed as follows: the 1.7 Kb PCR product of the Bmi-1 3'-UTR was inserted into pCR2.1-TOPO for sequence verification, and was then removed at the Xho I sites mentioned above and inserted in to pcDNA3.1/Bmi-1 5'-UTR.luc at the Xho I site within the pcDNA vector's multiple cloning site. Subsequently, site-directed mutagenesis was used to remove the extra bases on the original vector between the end of the firefly luciferase gene and the 3'-UTR insert. The mutagenesis reaction was also used to remove the original firefly luciferase stop codon "TAA," causing the new stop codon to be now in-frame "TGA" of the Bmi-1 ORF. The site directed mutagenesis primer is: 5'ggcggaaagtccaaattgtcatcag-caacttcttctgg 3'.

pcDNA3.1/Bmi-1 3'-UTR.luc (FIG. 6C) was constructed by removing the Bmi-1 5'-UTR sequence from pcDNA3.1/Bmi-1 5'+3'-UTR.luc at the flanking BamHI sites, followed by self-ligating the remaining vector at the BamHI cuts.

pcDNA3.1.luc was constructed by ligating BamH I/Not I fragment (firefly luciferase gene open reading frame) from plasmid p2luc with BamH I/Not I treated pcDNA3.1 vector.

Cell Culture

Human embryonic kidney 293 cells and fibrosarcoma HT1080 cells, purchased from ATCC, were maintained in DMEM (Gibco BRL, Invitrogen) containing 1 g/L glucose, supplemented with 10% fetal bovine serum, penicillin (50 IU/mL), and streptomycin (50 ug/mL). Multiple lineage progenitor cells (MLPC) were purchased from BioE, Inc and cultured in MSCBM medium (Cambrex). Cells were cultured at 37° C. in a humidified atmosphere containing 5% $CO_2$.

Reporter Gene Assay: Transient Transfections of Monocistronic Vectors

Human embryonic kidney 293 cells were seeded in a 96-well plate. After 4 hours, pcDNA3.1/Bmi-1 UTR.luc or control construct were co-transected with pcDNA3.1/GFP using FuGENE-6 reagent (Roche). Briefly, 293 cells were seeded in a black 96-well plate at 20,000 cells per well and incubated overnight at 37 C. 30 ng of pcDNA/GFP construct (gift from Virology group at PTC) was co-transfected with 30 ng Bmi-1 UTRs containing constructs using FuGENE-6 reagent (Roche). 0.2 µL FuGENE-6 was diluted in 5 up DMEM containing 10% FBS (Invitrogen). DNAs were mixed together and added to the diluted FuGENE-6 mix. After 15 minutes at room temperature, 5 up of the transfection mix was added to each well. After 48 hours, GFP activity was measured as fluorescence using a View-Lux plate reader (Perkin-Elmer). 100 up prepared Steady-Lite HTS substrate (Perkin-Elmer) was then added to each well. After 2 minutes on an orbital shaker, luciferase activity was read on TopCount plate reader (Perkin-Elmer) using 1 second counts. To test the role of each Bmi-1 UTR in regulation of protein expression, the Bmi-1 UTRs-containing reporter vectors were co-transfected with a GFP expressing vector, which was used to normalize the transfection efficiency.

Results

Figure 7:
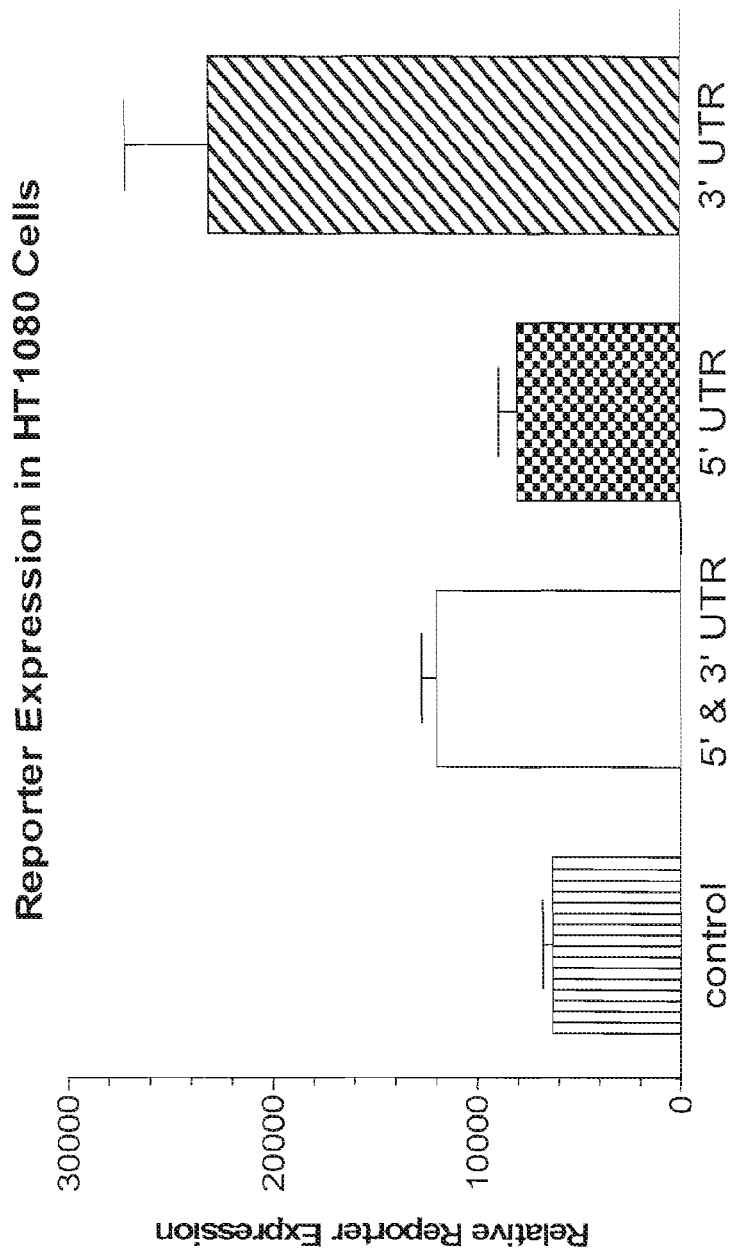
FIG. 7: UTR-Mediated Regulation of Bmi-1 Expression: Bar graph showing the effect of various human Bmi-1 UTR sequences in controlling reporter luciferase expression. Reporter gene expression by HT1080 cells transfected with the following nucleic acid constructs was assessed by measuring luciferase activity (y-axis): pcDNA3.1.luc, a construct comprising the luciferase gene flanked by control UTRs that were derived from the vector (lane 1); the pcDNA3.1/Bmi-1 5'+3'-UTR.luc construct (lane 2); the PcDNA3.1/Bmi-1 5'-UTR.luc construct (lane 3); and the pcDNA3.1/Bmi-1 3'-UTR.luc construct (lane 4).

As shown in FIG. 7, the Bmi-1 3'-UTR increased expression of luciferase by more than 2 fold whereas the Bmi-1

5'-UTR maintained the expression level of the reporter gene as compared to the control vector pcDNA3.1.luc. However, in the presence of both the 5'-UTR and 3'-UTR of Bmi-1, the luciferase expression was significantly lower than in the presence of the Bmi-1 3'-UTR alone. These data suggest that the Bmi-1 3'-UTR enhances Bmi-1 gene expression and the Bmi-1 5'-UTR regulates the stimulating effect of the Bmi-1 3'-UTR.

Example 2

IRES Activity in the 5' UTR of Bmi-1

To determine the presence of an IRES (Internal Ribosome Entry Site) in the 5'-UTR of Bmi-1, the Bmi-1 5'-UTR sequence was cloned into a bicistronic luciferase reporter vector p2luc, a construct widely used to test for IRES activity. In this vector, expression of the first reporter, renilla luciferase, is driven by cap-dependent translation, while the translation of second reporter, firefly luciferase, only occurs if there is IRES activity between the two reporter genes.

Preparation of Nucleic Acid Constructs

All DNA constructs were generated using standard procedures (Sambrook, J., Fritsch, E. & Maniatis, T. *Molecular cloning: A laboratory manual* (Cold Spring Harbor Laboratory Press, Cold Spring Harbor, N.Y., 1989). All PCR reagents were purchased from Invitrogen and the restriction enzymes were bought from New England BioLab.

Figure 8A:
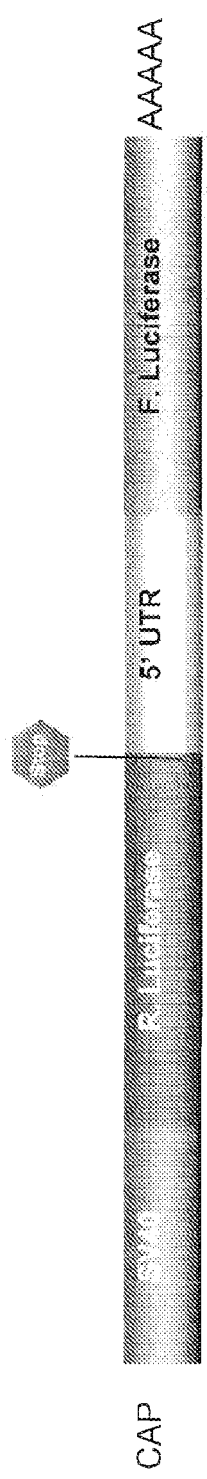
FIGS. 8A-8B: Biscistronic Reporter Constructs containing Bmi-1 5'-UTR: Schematic representation of the following biscistronic reporter constructs containing human Bmi-1 5'-UTR: 8A) p2luc/Bmi-1 5'-UTR, comprising, in the following order, the SV40 promoter, the renilla luciferase gene, the 5' UTR of a human Bmi-1 gene, the first 21 nucleotides from the 5' end of the ORF of human Bmi-1, and the firefly luciferase gene. 8B) p2luc/Bmi-1 5'-UTR-reverse, comprising, in the following order, the SV40 promoter, the renilla luciferase gene, the 5' UTR of human Bmi-1, the first 21 nucleotides from the 5' end of the ORF of human Bmi-1, in the reverse orientation, and the firefly luciferase gene.
Figure 8B:
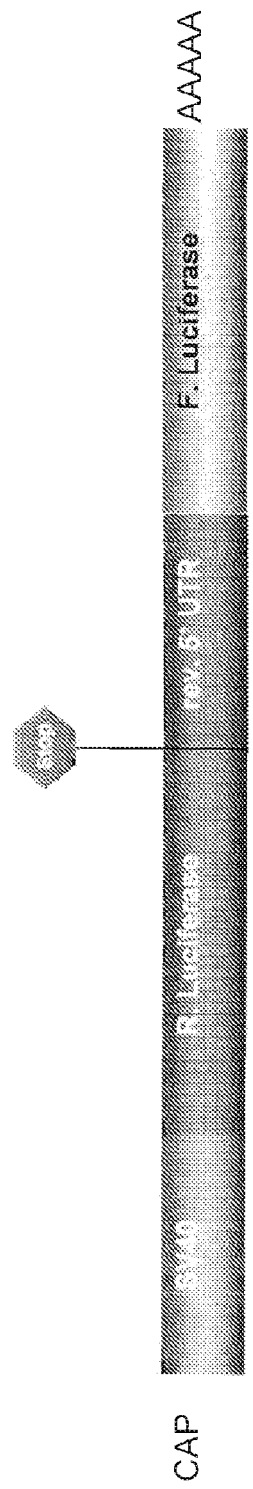

To determine whether the Bmi-1 5'-UTR contains an IRES, the following DNA constructs were made: i) p2luc/Bmi-1 5'-UTR (FIG. 8A), a bicistronic construct comprising the human Bmi-1 5'-UTR, 21 nucleotides from the 5' end of the ORF of human Bmi-1, the *Renilla* luciferase reporter gene, and the Firefly luciferase reporter gene, wherein the 5'-UTR of human Bmi-1 and the 21 nucleotides from the 5' end of the human Bmi-1 ORF are between the *Renilla* luciferase reporter gene and the Firefly luciferase reporter gene; 2) p2luc/Bmi-1 5'-UTR-reverse (FIG. 8B), a control bicistronic construct similar to p2luc/Bmi-1 5'-UTR but with the 5'-UTR in the reverse order; 3) NP-2luc/Bmi-1 5'-UTR, a promoterless control bicistronic vector that is similar to p2luc/Bmi-1 5'-UTR, but without the CMV promoter; and 4) a control bistronic vector p2luc/HCV-IRES that has the HCV IRES between the two luciferase reporters instead of the Bmi-1 5'-UTR.

Briefly, the Bmi-1 5'-UTR was isolated from the pCR4Blunt vector by using BamH I digestion, then inserted into p2luc vector between the two reporter genes at BgI II and BamH I sites. This resulted in generation of the first two constructs p2luc/Bmi-1 5'-UTR and p2luc/Bmi-1 5'-UTR-reverse by determining the orientation of the insert Bmi-1 5'-UTR. The third promoterless construct NP-Bmi-1 5'-UTR was generated by removing the CMV promoter in p2luc/Bmi-1 5'-UTR with Hind III and Kpn I digestion, followed by blunt end ligation.

Reporter Gene Assay: DNA Transient Transfection

DNA transient transfection was performed using FuGENE-6 reagent as per manufacturer's instruction (Roche). Briefly, human embryonic kidney 293 cells were seeded in 6-well plates at a density of $2.5\times10^5$ cells/well and incubated overnight at 37° C. Cells were transfected with a mixture of 6 μl FuGENE-6+2 μg of p2luc/Bmi-1 5'-UTR or control constructs. After 48 hours, media was aspirated, and cells were lysed by adding 500 μL of lysis buffer (5× passive lysis buffer diluted in dH2O, Promega). Lysate was diluted 1:100 in PBS and 20 up was transferred/well in a 96-well plate. *Renilla* and Firefly luciferase reporter activity was measured using 100 up each of Dual Luciferase Reporter Assay reagents (Promega), prepared as per manufacturer's instructions. Luminescence output was read on a TopCount plate reader (Perkin-Elmer) using 1 second counts.

When testing the promoterless vector NP-2luc/Bmi-1 5'-UTR, a reporter vector pcDNA/GFP was added to each transfection as an internal control of transfection efficiency. 293T cells were seeded in a black 96-well plate at 20,000 cells/well and incubated overnight at 37 C. 30 ng of pcDNA/GFP construct was cotransfected with 30 ng Bmi-1 UTR containing constructs using FuGENE-6 reagent (Roche). Briefly, 0.2 up FuGENE-6 was diluted in 5 up DMEM containing 10% FBS (Invitrogen). DNAs were mixed together and added to the diluted FuGENE-6 mix. After 15 minutes at room temperature, 5 up of the transfection mix was added to the cells in each well. After 48 hours, GFP activity was measured as fluorescence using a View-Lux plate reader (Perkin-Elmer). Media was then aspirated and cells lysed using 20 up prepared passive lysis buffer (5× passive lysis buffer diluted in dH2O, Promega). 10 up of lysate was read using 100 up each of Dual Luciferase Reporter Assay reagents (Promega), prepared as per manufacturer's instructions. Luminescence output was read on a View-Lux plate reader using 5 second counts (Perkin-Elmer).

In Vitro Translation

Plasmid DNA p2luc/Bmi-1 5'-UTR and control vectors were linearized using digestion enzyme Hpa I (New England Biolabs). A transcription reaction was carried out using mMessage mMachine T7 Kit (Ambion), as per manufacturer's instructions. mRNA was resolved on an agarose gel and purified using a Nuc-Away column (Ambion) and 2 μL of RNAse inhibitors (Promega) were added per 40 μL reaction. 250 ng mRNA was used per 50 μL in vitro translation reaction in Rabbit Reticulocyte Lysate System (Promega), as per suggested protocol. After 90 minute incubation at 30° C., 30 μL of each reaction was transferred to a 96-well plate and *Renilla* and Firefly luciferase activity was measured using 30 μL/well of prepared LARII and Stop and Glo reagents (Promega, Dual Luciferase Reporter Assay).

Results

Figure 9:
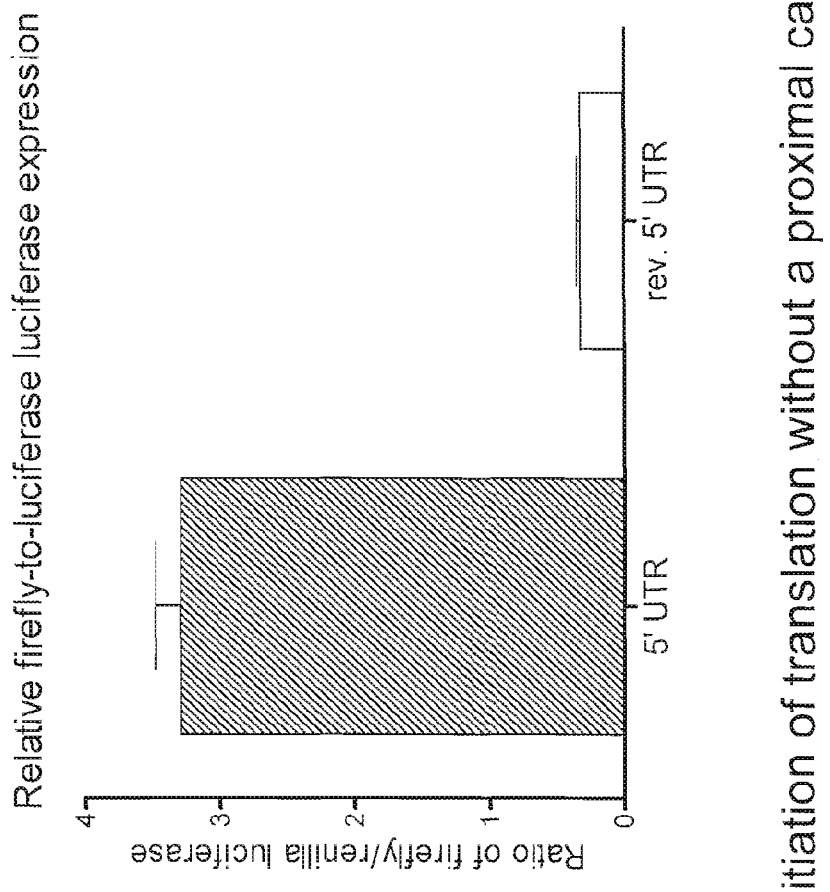
FIG. 9: Cap-independent translation mediated by human Bmi-1 5'-UTR. Bar graph showing the effect of the orientation of human Bmi-1 5'-UTR sequences in controlling cap-independent expression. The ratio of firefly luciferase to renilla luciferase activity (y-axis) by HT1080 cells transfected with the following nucleic acid constructs was measured: p2luc/Bmi-1 5'-UTR (lane 1) and p2luc/Bmi-1 5'-UTR-reverse (lane 2).

Transfection of both plasmids, p2luc/13 ml-1 5'-UTR and p2luc/Bmi-1 5'-UTR-reverse, resulted in strong and similar levels of *Renilla* Luciferase expression (FIG. 9). However, only the vector containing the correct orientation of the Bmi-1 5'-UTR sequence expressed strong Firefly luciferase activity. This experiment thus indicates potential IRES activity in Bmi-1 5'-UTR.

To rule out the possibility that the 5'-UTR has cryptic promoter activity, a promoterless vector NP-2luc/Bmi-1 5'-UTR was generated. Transfection with this plasmid resulted in almost complete loss of the expression of both *Renilla* luciferase and Firefly luciferase activity, compared to transfection with the wild type vector that has the CMV promoter. In this study, a GFP-expressing vector was transfected as an internal control of transfection efficiency. There was no difference in GFP expression between the two transfections. These results indicate that there is no cryptic promoter in the Bmi-1 5'-UTR.

Figure 10A:
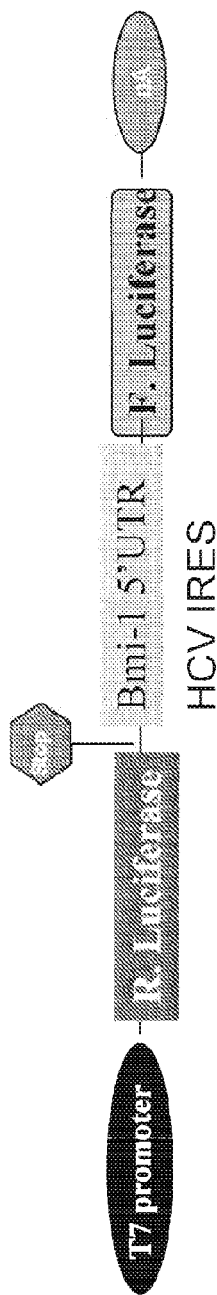
FIGS. 10A-10B: In Vitro Translation of Bicistronic Bmi-1 5'-UTR. 10A) Schematic representation of the following constructs: (1) p2luc/Bmi-1 5'-UTR, comprising, in the following order, a T7 promoter, renilla luciferase gene, 5'-UTR of Bmi-1, firefly luciferase gene, and poly A tail, and (2) p2luc/HCV-IRES, comprising, in the following order, a T7 promoter, renilla luciferase gene, HCV IRES (Tsukiyama-Kohara et al., J. Virol. 1992, 66(3):1476-83), firefly luciferase gene, and poly A tail. 10B) Bar graph showing the affect of in vitro translation of the following constructs in rabbit reticulacyte lysate (RRL) extracts as measured by firefly luciferase activity: p2luc/Bmi-1 5'-UTR (lane 1); and p2luc/HCV-IRES, (lane 2).
Figure 10B:
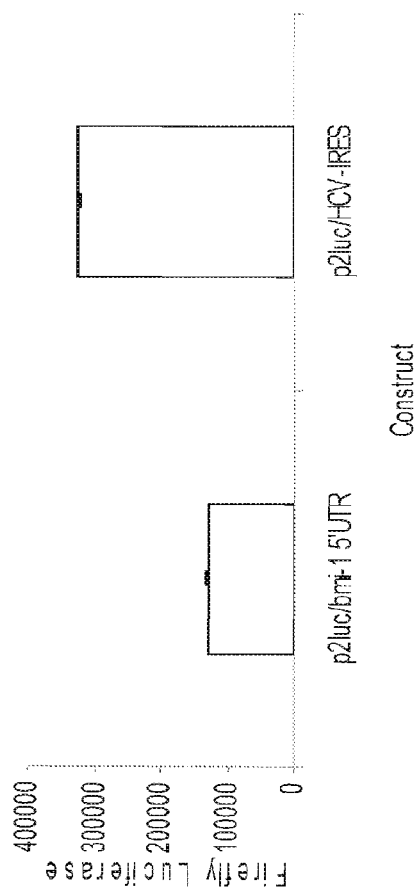

In the in vitro translation assay, bicistronic plasmids were linearized and transcribed in vitro with T7 promoter. The synthesized mRNA was then resolved on and excised from agarose gel for further purification. Thus, there was no possibility that a cryptic promoter and cryptic splice acceptor would be involved. As shown in FIG. 10, transcript mRNA from the p2luc/Bmi-1 5'-UTR vector demonstrated significant expression level of the second cistronic reporter gene Firefly luciferase. This in vitro translation assay further supports the presence of an IRES in the Bmi-1 5'-UTR.

Example 3

Identification of Compounds that Inhibit Bmi-1 Expression Post-Transcriptionally As shown in the following example, compounds that decrease or down-regulate the expression of Bmi-1 protein have been identified and have the potential to treat cancer. Human embryonic kidney (293H) cell lines expressing the firefly luciferase (fLuc) reporter gene flanked by the 5'-UTR and 3'-UTR of Bmi-1 mRNA were constructed and used to identify and validate compounds able to specifically decrease, down-regulate, or reduce expression of a reporter gene via nucleic acid constructs comprising at least the 5'-UTR and 3'-UTR of Bmi-1, as well as decrease, down-regulate, or reduce expression of endogenous Bmi-1 protein.
Preparation of the Nucleic Acid Constructs Comprising the UTRs of Bmi-1

A high-level expression vector, pcDNA™3.1/Hygro (Invitrogen Corp., Carlsbad, Calif.) was used for preparing the constructs comprising the luciferase gene flanked by any of the Bmi-1 5'-UTR and 3'-UTR, or the Bmi-1 5'-UTR or the Bmi-1 3'-UTR of Bmi-1 mRNA. In a pcDNA™3.1/Hygro vector, the UTRs and restriction sites associated with cloning, expressing, or cloning and expressing a gene of interest or a reporter gene were removed or replaced. For each construct containing 5'-UTR sequences, the 5'-UTR sequences with the first 21 nucleotides of Bmi-1 ORF were cloned into the vector using the appropriate restriction sites so that the first 21 nucleotides were in frame with the luciferase reporter gene.
Preparation of the Stable Cell-Line Stable 293H cell lines containing the firefly luciferase (fLuc) gene flanked by Bmi-1 5'-UTR and 3'-UTR were cultured in DMEM medium supplemented with 10% FBS and 200 ug/mL hygromycin in Fisher T175 flasks. The cells were passaged every 4 days at 1:10 dilution. Cultures were kept in a 37° C. and 5% $CO_2$ incubator. The cells were scaled-up over a three day period before performing the assay. Two confluent T175 flasks were split into twenty T175 flasks (1:10 dilution). Cells were harvested from each confluent flask by removing all of the media and adding 4 mL of warmed trypsin to dislodge the cells. After the cells were dislodged, 16 mL of selective media was added for a final volume of 20 mL. The cells were expanded by adding 2 mL of the harvested cells into ten new T175 flasks plus 25 mL of selective media. The twenty new flasks are placed into the 37° C., 5% $CO_2$ incubator. On the day the assay was performed, the media was removed from the flasks and 3 mL of warmed trypsin was added to dislodge the cells. After the cells were dislodged, 10 mL of nonselective media was to the flask. This was repeated for all twenty flasks and combined into one flask. 100 μL of the above cell culture plus 100 μL of Trypan Blue stain was counted on a hemocytometer. Cells were plated in the presence of 2 μL of a compound to be tested (at final concentration of 7.5 μM with 0.5% DMSO).
Preparation of Standard Plates Standard 96-well clear Matrix Screen Mates plates were used. 459 μL of 100% DMSO was added to make a 100 mM solution. A fresh 30 mL 10% DMSO stock solution was made by adding 3 mL of 100% DMSO to 27 mL of water. The 10% DMSO was used to make serial dilutions of a Puromycin stock solution so that the DMSO concentration remained at 10%.

Using standard techniques known to one skilled in the art, Puromycin was serially diluted to provide 10 mM Stock in 10% DMSO (by diluting 100 μL of 100 mM Stock with 900 μL water), 1 mM Stock in 10% DMSO (by diluting 500 μL of 10 mM Stock with 4.5 mL 10% DMSO), 400 μM Stock in 10% DMSO (by diluting 1.6 mL of 1 mM Stock with 2.4 mL 10% DMSO, 20 μM was the final amount used in assay), 200 μM Stock in 10% DMSO (by diluting 1 mL of 400 μM Stock with 1 mL 10% DMSO, 10 μM was the final amount used in assay), 100 μM Stock in 10% DMSO (by diluting 1 mL of 200 μM Stock with 1 mL 10% DMSO, 5 μM was the final amount used in assay), 50 μM Stock in 10% DMSO (by diluting 1 mL of 100 μM Stock with 1 mL 10% DMSO, 2.5 μM was the final amount used in assay), 25 μM Stock in 10% DMSO (by diluting 1 mL of 50 μM Stock with 1 mL 10% DMSO, 1.25 μM was the final amount used in assay), 12.5 μM Stock in 10% DMSO (by diluting 1 mL of 25 μM Stock with 1 mL 10% DMSO, 0.625 μM was the final amount used in assay), 6.25 μM Stock in 10% DMSO (by diluting 1 mL of 12.5 μM Stock with 1 mL 10% DMSO, 0.312 μM was the final amount used in assay), 3.125 μM Stock in 10% DMSO (by diluting 1 mL of 6.25 μM Stock with 1 mL 10% DMSO, 0.156 μM was the final amount used in assay) and 1.56 μM Stock in 10% DMSO (by diluting 1 mL of 3.125 μM Stock with 1 mL 10% DMSO, 0.078 μM was the final amount used in assay).
Firefly Luciferase Substrate Preparation The firefly luciferase substrate used was Luc Lite Plus Packard #6016969. Luciferase activity was immediately assayed using a ViewLux Imaging system (Perkin Elmer).
Cytotoxicity Assay To evaluate cytotoxicity of the compounds in the 293H cell lines, the CellTiter-Glo® assay (Promega) is utilized. CellTiter-Glo® determines the number of viable cells in culture based on quantification of the ATP present, which signals the presence of metabolically active cells. A reduction in cellular ATP is indicative of a cytotoxic or cytostatic effect. Doxorubicin, a known cytotoxic compound, is used to address the sensitivity of the tested cell line. For relatively sensitive cell lines, such as U937 (a human monocyte cell line), the $CC_{50}$ of doxorubicin ranges from 4 to 10 nM. For cell lines exhibiting an intermediate level of sensitivity to compound treatment such as human Huh7 cells (a human hepatoblastoma cell line), the $CC_{50}$ of doxorubicin ranges from 70 to 300 nM.
Bmi-1 Sandwich ELISA
Cell Seeding and Compound Treatment (Day 1):

HT-1080 cells were seeded at 5000 cells/well (50 μL) in 96-well tissue culture plates. After the cells become adherent (3-4 hours), 2× diluted stocks of compounds in 50 μL DMEM containing 1% DMSO (final DMSO concentration was 0.5%) were added and the plates were incubated at 37° C. under 5% $CO_2$ for 40-48 hours
ELISA Plate First Antibody Preparation (Day 2):

The First Antibody (Millipore Mouse, monoclonal to mouse Bmi-1, clone F6, catalog #05-637) diluted to 2 μg/mL in PBS was added (100 μL) to each well of a Nunc MaxiSorp 96-well ELISA plate. The plate was covered with a plate seal and allowed to stand overnight.
Cell Lysate Preparation (Day 3):

Fresh 1× Lysis buffer was prepared on the day of the assay as follows: 1 mM EDTA, 150 mM NaCl, 0.5% Triton-X 100, 10 mM NaF, 20 mM B-Glycerophosphate, 1 mM DTT (in PBS, pH 7.2-7.4) and 1×HALT protease inhibitor cocktail (Pierce #78410).

1× Lysis Buffer (40 μL) was added to each well and the plate was shaken for 5-10 minutes on an orbital shaker to allow cell lysis, then Diluent (1% BSA in PBS in 0.5% NP40) (100 μL) was added to each well.

The Bmi-1 standard curve was prepared in Diluent at the following concentrations of protein: 8000, 4000, 2000, 1000, 500, 250, 125, 0 pg/mL The Bmi-1 Recombinant Protein Standard (Novus Biologicals PCGF4 Recombinant Protein (P01), catalog #H00000648-P01) used in the standard curve was stored at −80° C., and on first thaw, diluted to 10 μg/μL in Blocking Buffer (1% BSA in PBS; BSA: Fisher Scientific Catalog #1600-100) before being aliquoted and refrozen at −80° C. Aliquots can be kept at 4° C. and reused after first thaw, but only for 1-2 weeks. The Bmi-1 Recombinant Protein Standard contains a GST and thus will show up on western blots around 70 Kda.

ELISA Assay (Day 3):

The prepared ELISA plate was washed 3× with Wash Buffer (0.05% Tween-20 in PBS). The final wash was removed from the plate and the plate was blotted dry on paper towels. Blocking Buffer (300 μL) (1% BSA in PBS) was added per well. The plate was covered with a plate seal and incubated at room temperature for 1 hour. The blocked plate was washed 3× with Wash Buffer, the final wash was removed and the plate was blotted dry on paper towels. The previously prepared samples and standards were added (at 100 μL/well) and the plate was covered with a plate seal and incubated at 4° C. overnight.

ELISA Assay (Day 4):

The prepared ELISA plate was removed from 4° C., incubated at room temperature for 30 minutes, then washed and blotted dry as previously described for Day 3. The Second Antibody (Cell Signaling Rabbit anti-Bmi-1, Cat #2830) diluted to 1:600 in Blocking Buffer was added (100 up) to each well, except as needed for background control wells. The plate was covered with a plate seal and incubated for 1.5 hrs at room temperature.

The ELISA plate was washed and blotted dry as previously described. The Third Antibody (Cell Signaling HRP conjugated anti-rabbit IgG (CellSignaling, Cat#: 7074) diluted to 1:300 in Blocking Buffer was added (100 μL) to each well, except as needed for background control wells. The plate was incubated for 1 hr at room temperature.

The plate was washed and blotted dry as previously described, then prepared TMB substrate (TMB substrate kit, Pierce catalog #34021) (prepared by mixing kit reagents 1:1) (100 μL) was added per well. The plate was incubated for 20-30 minutes at room temperature in the dark, then Stop Solution (2 M sulfuric acid in water) (50 up) was added per well. The plates were read at OD450 (experimental) and OD570 (reference).

Results

The clone selected for high throughput screening was stable and maintained a high level of luciferase expression. Northern blot analysis confirmed that the clone F8 cells contained the integrated and intact target gene sequence, including the open reading frame of the luciferase reporter flanked with Bmi-1 5' and 3' UTRs. Prior to use, experimental conditions were optimized, including cell number, incubation time, DMSO concentration and substrate volume.

In this screen, the data were analyzed as a normal distribution, apparent from graphical and statistical analysis of skewness and kurtosis, yielding a mean inhibition of −4% with a standard deviation of 22.3%. Hits were then reported at the 99.73% confidence level, representing a selection of 3 standard deviations from the mean, or a hit lower limit of observed inhibition equal to 62.9%. These selection criteria resulted in a hit rate of approximately 0.5%, which is in line with current industry standards for high throughput screening processes.

The results for the compounds shown in Table 1 demonstrate that compounds identified using a high throughput screening method described herein down-regulate the post-transcriptional expression of Bmi-1.

TABLE 1

ELISA $EC_{50}$ (μM) and luciferase $EC_{50}$ (μM)

| Compound | ELISA | luciferase |
|---|---|---|
| 1 | 0.41 | 0.53 |
| 2 | 0.66 | 0.91 |
| 3 | >3 | 17.6 |
| 4 | 0.32 | 0.54 |
| 5 | 0.71 | 0.80 |
| 6 | 1.7 | 2.6 |
| 7 | 0.36 | 0.75 |
| 8 | 0.39 | 3.8 |
| 9 | 1.09 | 0.94 |

Various patent, patent applications, and publications are cited herein, the disclosures of which are incorporated by reference in their entireties.

What is claimed is:

1. A method for identifying or validating a small molecule compound that modulates the translation of a nucleic acid construct comprising the steps of:
   (a) contacting the compound with a host cell containing the nucleic acid construct, wherein the nucleic acid construct comprises the following operably linked polynucleotides in 5' to 3' order; 5' untranslated region (5'-UTR) transcript of human Bmi-1 defined by SEQ ID NO: 1, the first 21 nucleotides from the 5' end of the open reading frame (ORF) of human Bmi-1, a reporter mRNA transcript, a transcript of the last 21 nucleotides from the 3' end of the ORF of human Bmi-1, and a 3' untranslated region (3'-UTR) transcript of human Bmi-1 defined by SEQ ID NO: 2, wherein the host cell is engineered to stably express a reporter protein translated from the nucleic acid construct; and
   (b) detecting the amount or activity of the reporter protein translated from the nucleic acid construct,
   wherein a compound that modulates the translation of the nucleic acid construct is identified or validated if the amount or activity of the reporter protein detected in the presence of the compound is altered relative to a previously determined reference range, or relative to the amount or activity of the reporter protein detected in the absence of the compound or the presence of a negative control.

2. The method of claim 1, wherein the compound that down-regulates translation of the nucleic acid construct is identified or validated if the amount or activity of said reporter protein detected in the presence of the compound is down-regulated or reduced relative to a previously determined reference range, or relative to the amount or activity of said reporter protein detected in the absence of said compound or the presence of a negative control.

3. A method for identifying or validating a small molecule compound that down-regulates translation of a nucleic acid transcript comprising the steps of:
   (a) contacting the compound with a host cell containing the nucleic acid construct, wherein the nucleic acid construct comprises the following operably linked polynucleotides in 5' to 3' order: a 5' untranslated region (5'-UTR) transcript of human Bmi-1 defined by SEQ ID NO: 1, the first 21 nucleotides from the 5' end of the open reading frame (ORF) of human Bmi-1, a reporter mRNA transcript, a transcript of the last 21 nucleotides from the 3' end of the ORF of human Bmi-1, and a 3' untranslated region (3'-UTR) transcript of human Bmi-1 defined by SEQ ID NO: 2, wherein the host cell is engineered to stably express a reporter protein translated from the nucleic acid construct; and
   (b) detecting the amount or activity of the reporter protein translated from the nucleic acid construct,
   wherein a compound that down-regulates translation of Bmi-1 is identified or validated if the amount or activity of the reporter protein detected in the presence of the compound is decreased when compared to the absence of the compound or a positive control compound selected from N-(2,6-dibromo-4-methoxyphenyl)-4-(2-methylimidazo[1,2-a]pyrimidin-3-yl)thiazol-2-amine, N-(2,6-dichloro-4-methoxyphenyl)-4-(2-methylimidazo[1,2-a]pyrimidin-3-yl)thiazol-2-amine, N-(2,6-difluoro-4-methoxyphenyl)-4-(2-methylimidazo[1,2-a]pyrimidin-3-yl)thiazol-2-amine, N-(2,6-dibromo-4-methylphenyl)-4-(2-methylimidazo[1,2-a]pyrimidin-3-yl)thiazol-2-amine, 4-(2-methylimidazo[1,2-a]pyrimidin-3-yl)-N-(2,4,6-tribromophenyl)thiazol-2-amine, N-(2,6-dibromo-4-(2-methoxyethoxy)phenyl)-4-(2-methylimidazo[1,2-a]pyrimidin-3-yl)thiazol-2-amine, 4-(6-chloroimidazo[1,2-a]pyridine-3-yl)-N-(2,6-dibromo-4-methoxyphenyl)thiazol-2-amine, 4-(6-chloroimidazo[1,2-a]pyridine-3-yl)-N-(2,6-dibromo-4-methylphenyl)thiazol-2-amine or 4-(6-chloroimidazo[1,2-a]pyridine-3-yl)-N-(2,6-dichloro-4-methoxyphenyl)thiazol-2-amine.

* * * * *

SEQUENCE LISTING

<160> NUMBER OF SEQ ID NOS: 8

<210> SEQ ID NO 1
<211> LENGTH: 505
<212> TYPE: RNA
<213> ORGANISM: Homo sapiens
<220> FEATURE:
<221> NAME/KEY: misc_feature
<223> OTHER INFORMATION: 5'-UTR of Human Bmi-1

<400> SEQUENCE: 1

```
cagcaacuau gaaauaaucg uaguaugaga ggcagagauc ggggcgagac aaugggaug      60 ugggcgcggg agcccoguuc cggcuuagca gcaccuccca gccccgcaga auaaaaccga   120
ucgcgccccc uccgcgcgcg cccucccccg agugcggagc gggaggaggc ggcggcggcc   180
gaggaggagg aggaggaggc cccggaggag gaggcguugg aggucgaggc ggaggcggag   240
gaggaggagg ccgaggcgcc ggaggaggcc gaggcgccgg agcaggagga ggccggccgg   300
```

| | |
|---|---|
| aggcggcaug agacgagcgu ggcggccgcg gcugcucggg gccgcgcugg uugcccauug | 360 |
| acagcggcgu cugcagcucg cuucaagaug gccgcuuggc ucgcauucau uuucugcuga | 420 |
| acgacuuuua acuuucauug ucuuuccgc ccgcuucgau cgccucgcgc cggcugcucu | 480 |
| uuccgggauu uuuuaucaag cagaa | 505 |

<210> SEQ ID NO 2
<211> LENGTH: 1771
<212> TYPE: RNA
<213> ORGANISM: Homo sapiens
<220> FEATURE:
<221> NAME/KEY: misc_feature
<223> OTHER INFORMATION: 3'-UTR of Human Bmi-1

<400> SEQUENCE: 2

| | |
|---|---|
| gguugauacc ugagacuguu aaggaaaaaa auuuuaaacc ccugauuuau auagauaucu | 60 |
| ucaugccauu acagcuuucu agaugcuaau acaugugacu aucgccaauu ugcuuucuu | 120 |
| uuguagugac auuaaauuug gcuauaaaag auggacuaca uguugauacuc cuauggacgu | 180 |
| uaauugaaaa gaaagauugu uguuauaaag aauugguuuc uggaaagca ggcaagacuu | 240 |
| uuucucugug uuaggaaaga ugggaaaugg uuucuguaac cauuguuugg auuuggaagu | 300 |
| acucugcagu ggacauaagc auugggccau aguuuguuaa ucuaacuaa cgccuacauu | 360 |
| acauucuccu ugaucguucu uguauuacg cguuuugug aaccuguaga aaacaagugc | 420 |
| uuuuuaucuu gaauucaac caacggaaag aauaugcaua gaauaaugca uucuauguag | 480 |
| ccaugucacu ugaauaaacg auuucuugca uauuuagcca uuuugauucc uguuugauuu | 540 |
| auacuucucu guugcuacgc aaaaccgauc aaagaaaagu gaacuucagu uuuacaaucu | 600 |
| guaugccuaa aagcgggguac uaccguuuau uuuacugacu guuuaaaug auucgcuuuu | 660 |
| guaagaauca gauggcauua ugcuuguugu acaaugccau auuggauauau gacauaacag | 720 |
| gaaacaguau uguaugauau auuuauaaau gcuauaaaga aauauugugu uucaugcauu | 780 |
| cagaaaugau uguuaaaauu cucccaacug guucgaccuu ugcagauacc cauaaccuau | 840 |
| guugagccuu gcuuaccagc aaagaauauu uuuaaugugg auaucuaauu cuaaagucug | 900 |
| uuccauuaga agcaauuggc acaucuuucu uacuuuaua uacuuuucuc caguaauaca | 960 |
| uguuuacuuu aaaaauuguu gcagugaaga aaaaccuuua acugaaaau auggaaaccg | 1020 |
| ucuuaauuuu ccauggcua ugauggaauu aauauuguau uuuaaaaaug cauauugauc | 1080 |
| acuauaauuc uaaacaauu uuuuaaauaa accagcaggu ugcuaaaaga aggcauuuua | 1140 |
| ucuaaaguua uuuuaauagg ugguauagca guaauuuaa auuuaagagu ugcuuuuaca | 1200 |
| guuaacaaug gaauaugccu ucucugcuau gucugaaaau agaagcuauu uauuaugagc | 1260 |
| uucuacaggu auuuuuaaau agagcaagca uguugaauuu aaaauaugaa uaccccacc | 1320 |
| caacaauuuu caguuuauuu uuugcuuugg ucgaacuugg ugugguuca ucacccauca | 1380 |
| guuauuugug agggguguuua uucuauauga auauuguuuc auguuuguau gggaaaauug | 1440 |
| uagcuaaaca uuucauuguc cccagucugc aaaagaagca caauucuauu gcuuugcuuu | 1500 |
| gcuuauagc auuaaaucau uacuuuuaca uauauugcug uuacuucgc uuucuuuaaa | 1560 |
| aauauaguaa aggauguuuu augaagucac aagauacaua uauuuuauu uugaccuaaa | 1620 |
| uuuguacagu cccauuguaa guguuguuuc uaauauaga uguaaaauga aauucauuu | 1680 |
| guaauuggaa aaaauccaau aaaaaggaua uucauuuaga aaaaaaaaaa aaaaaaaaaa | 1740 |
| aaaaaaaaaa aaaaaaaaaa aaaaaaaaaa a | 1771 |

```
<210> SEQ ID NO 3
<211> LENGTH: 49
<212> TYPE: DNA
<213> ORGANISM: Artificial Sequence
<220> FEATURE:
<223> OTHER INFORMATION: Forward primer used for cloning the Bmi-1 5'-
      UTR

<400> SEQUENCE: 3
tttggatcct aacagcaact atgaaataat cgtagtatga gaggcagag            49

<210> SEQ ID NO 4
<211> LENGTH: 37
<212> TYPE: DNA
<213> ORGANISM: Artificial Sequence
<220> FEATURE:
<223> OTHER INFORMATION: Reverse primer used for cloning the Bmi-1 5'-
      UTR

<400> SEQUENCE: 4
tttggatcct aatgagaggc agagatcggg gcgagac                         37

<210> SEQ ID NO 5
<211> LENGTH: 36
<212> TYPE: DNA
<213> ORGANISM: Artificial Sequence
<220> FEATURE:
<223> OTHER INFORMATION: Forward primer used for cloning the Bmi-1 3'-
      UTR

<400> SEQUENCE: 5
tttctcgagt catcagcaac ttcttctggt tgatac                          36

<210> SEQ ID NO 6
<211> LENGTH: 36
<212> TYPE: DNA
<213> ORGANISM: Artificial Sequence
<220> FEATURE:
<223> OTHER INFORMATION: Reverse primer used for cloning the Bmi-1 3'-
      UTR

<400> SEQUENCE: 6
tttctcgagc taaatgaata ccttttttat tggatt                          36

<210> SEQ ID NO 7
<211> LENGTH: 471
<212> TYPE: DNA
<213> ORGANISM: Mus musculus
<220> FEATURE:
<221> NAME/KEY: misc_feature
<223> OTHER INFORMATION: 5'-UTR of Mouse Bmi-1

<400> SEQUENCE: 7
ataatcgtag tattaaaggc agagatcggg agagacaatg gggaggttgg cgagggagcc   60
ccgcgcaggc ttagcaacac ctcccggccc gcagaataa tacggctcgg ccccctctgcg   120 cgccctcccc cgagcgcggc cgggaggcgg cggctgcgcc gaggaggagg agaggccccg   180
aggaggcggc ggcggaggcc gcgcggaggc ggaggaggcc gcgcgggagg aggaggccgc   240
agcgcgcgag caggaggccg gcgggggagc ggcatgagcg gagcgcggcg gccgtggctg   300
ctctcggccg cgctcggtgc ccattgacag cggcggcggc ggctcgctcc aagatggccg   360
cttggctcgc attcatttta tgctgaacga ctttttaactt tcattgtctt ttccgcccgc   420
tcagatcgcc tcgcgccggc cgctctttcc gggatctttt atcaagcaga a            471

<210> SEQ ID NO 8
```

<211> LENGTH: 1742
<212> TYPE: DNA
<213> ORGANISM: Mus musculus
<220> FEATURE:
<221> NAME/KEY: misc_feature
<223> OTHER INFORMATION: 3'-UTR of Mouse Bmi-1

<400> SEQUENCE: 8

```
taggactgtt aaggaaaaga tttttcaacc ccctgattta gttaccttca ttcattacag     60
ctttatagat gcttaataca tgtgactgtc gtccagtttg cttcctttttg tagtgacttt   120
aaatttggcc ataaatgatg gactagatgt gatacttcat atggatgtta agtggaaaga   180
ttgattcttt ctctaaagaa ttggattctg agaaggattc tgtgttagga agatgtgaa    240
atgatttctg tgaccactgt ttggatctgg aaatgttcta cagtgggtag acattgggcc   300
atagtttgtt aatctcaatt aatgcctaca ttacattctc tttgattgtt cttgttatta   360
tgctgttctg tgaacctgta gaaacaagt gcttttatc ttgaaattca gcaaatggaa     420
agaataagca tagaatactg cattctgtgc agccacgtca ctgtgaataa caatttcttg   480
catatttagc catttaatt cctgtttgat ttttacttct ctgttgctac acaaaatgat    540
caaaggaaac ttgttttaca atctgtatgc ctaaaaagcg ggtactaccg tttattttac   600
tgacttgttg aaatgattca cttttgtaag aatcagatgg cattatgctt gttgtacaat   660
gccatattgg tatatgacat aacaggaaac agtattgtat gatatattta taaatactat   720
gaaaatattg tgtttcatgc attcaaaaac agttgtaaac ttctccaaat gggttcgacc   780
tttgcggata tcacagtgca cccaatgctg aggcttacca ccagcacaga atttgtttta   840
atgttgataa ccagtttcaa attcttttcc acttagaagc aaatggcaga tcttcatagt   900
tctggctttt ctccaataag actttcaaaa ttaatattgc agtaaagaaa aattttaacc   960
aaggcaaata tagtgtttaa ttttccattg gttaaaatag aattaatgtt tttaaattct  1020
gtttatcagt ggaattctaa aatagatttt aaagtcaacc agctaattgc tgaagtaaag  1080
cattttatct acaattttat tttagtgtat gtggcacaag tgtaatttca aatttaagag  1140
ttgttttcat agttaaagga atctgccttc actgtaacgt ctggaaacag aaacaatttg  1200
ttatgatttc tacagggatt tttaatagag caaacatgtt gaatttaaaa tatgaatgac  1260
ccctccaagt ctcagttttg ctttggtcga acttagcgtg tgtttatcag ccatcagtta  1320
tttgtgagga tgttaattcc gtatgaatat tgtttcatgt ttgtatggga aactgtagct  1380
aagcatttca ttgtctgcag tctgcagaag aagcacaatt gtattgcttt gtcttgcttg  1440
tagccattaa atcattactt ttacacacat tgctgttaac ttctgctttc tttaaagatt  1500
tagtaaattg atgtttatg aaggccacaa gatacatata tttttatttt gacctaaatt   1560
tgtacagtcc cattgtgtgt gtgtcatttc taattataga tgtaaaatta aatttcattt  1620
ttaattggaa aattcaataa aaagatattc atttagaaaa tactatgctc tttaattaaa  1680
attttgctat gaaaagcaca gtgtgcagaa gttttgggaa accctgtagt ggattgtaag  1740
ag                                                                 1742
```